(12) United States Patent
Basilico et al.

(10) Patent No.: US 7,294,706 B2
(45) Date of Patent: Nov. 13, 2007

(54) IDENTIFICATION OF RECEPTOR AND HEPARIN BINDING SITES IN FGF4 BY STRUCTURE-BASED MUTAGENESIS

(75) Inventors: Claudio Basilico, New York, NY (US); Moosa Mohammadi, New York, NY (US)

(73) Assignee: New York University, New York, NY (US)

( * ) Notice: Subject to any disclaimer, the term of this patent is extended or adjusted under 35 U.S.C. 154(b) by 530 days.

(21) Appl. No.: 10/771,238

(22) Filed: Feb. 2, 2004

(65) Prior Publication Data

US 2004/0229249 A1 Nov. 18, 2004

Related U.S. Application Data

(63) Continuation of application No. PCT/US02/24274, filed on Aug. 1, 2004.

(60) Provisional application No. 60/309,431, filed on Aug. 1, 2001.

(51) Int. Cl.
*A61K 38/27* (2006.01)
*C12N 5/08* (2006.01)

(52) U.S. Cl. ........................ 530/399; 435/336

(58) Field of Classification Search ............... 435/336; 530/399
See application file for complete search history.

(56) References Cited

U.S. PATENT DOCUMENTS 5,989,866 A 11/1999 Deisher et al.

FOREIGN PATENT DOCUMENTS

WO WO 98/39436 * 9/1998

OTHER PUBLICATIONS

Bowie et al., Deciphering the Message in Protein Sequences: Tolerance to Amino Acid Substitutions. Science. 1990. vol. 247, pp. 1306-1310.*
Wells, J.A., Additivity of Mutational Effects in Proteins. Biochemistry. 1990. vol. 29, No. 37, pp. 8509-8517.*
Paola Bellosta, et al., "Cleavage of K-FGF Produces a Truncated Molecule with Increased Biological Activity and Receptor Binding Affinity", The Journal of Cell Biology, col. 121, No. 3, May 1992, pp. 705-713.
Alexander N. Potnikov, et al., "Structural Basis for FGF Receptor Dimerization and Activation", Cell, vol. 98, Sep. 1999, pp. 641-650.
Alexander N. Potnikov, et al., "Crystal Structures of Two FGF-FGFR Complexes Reveal the Derminants of Ligand-Receptor Specificity", Cell, vol. 101, May 2000, pp. 413-424.

* cited by examiner

*Primary Examiner*—Karen Cochrane Carlson
*Assistant Examiner*—Suzanne M. Noakes
(74) *Attorney, Agent, or Firm*—Darby & Darby

(57) ABSTRACT

The present invention provides methods and compositions that may be used to modulate binding of a fibroblast growth factor (FGF) polypeptide to an FGF receptor (FGFR). In preferred embodiments, the methods and compositions of the invention modulate binding of a particular FGF polypeptide, the FGF4 polypeptide, to its receptor. The invention provides, in particular, variant FGF polypeptides that have at least one amino acid residue substitutions, insertion or deletion which alters the polypeptdies' binding affinity for an FGFR. The invention also provides models for the three-dimensional structure of a dimerized complex of FGF-FGFR-heparin. Using these models, key amino acid residues are identified and novel compounds (including novel variants of FGF and FGFR) can be identified which modulate FGF binding to its receptor. Such new compounds are therefore useful, e.g., as agonist and antagonist for FGF signaling and for bioactivities associated therewith.

2 Claims, 17 Drawing Sheets

Figure 2A

Residues that Interact with D2

Figure 1:
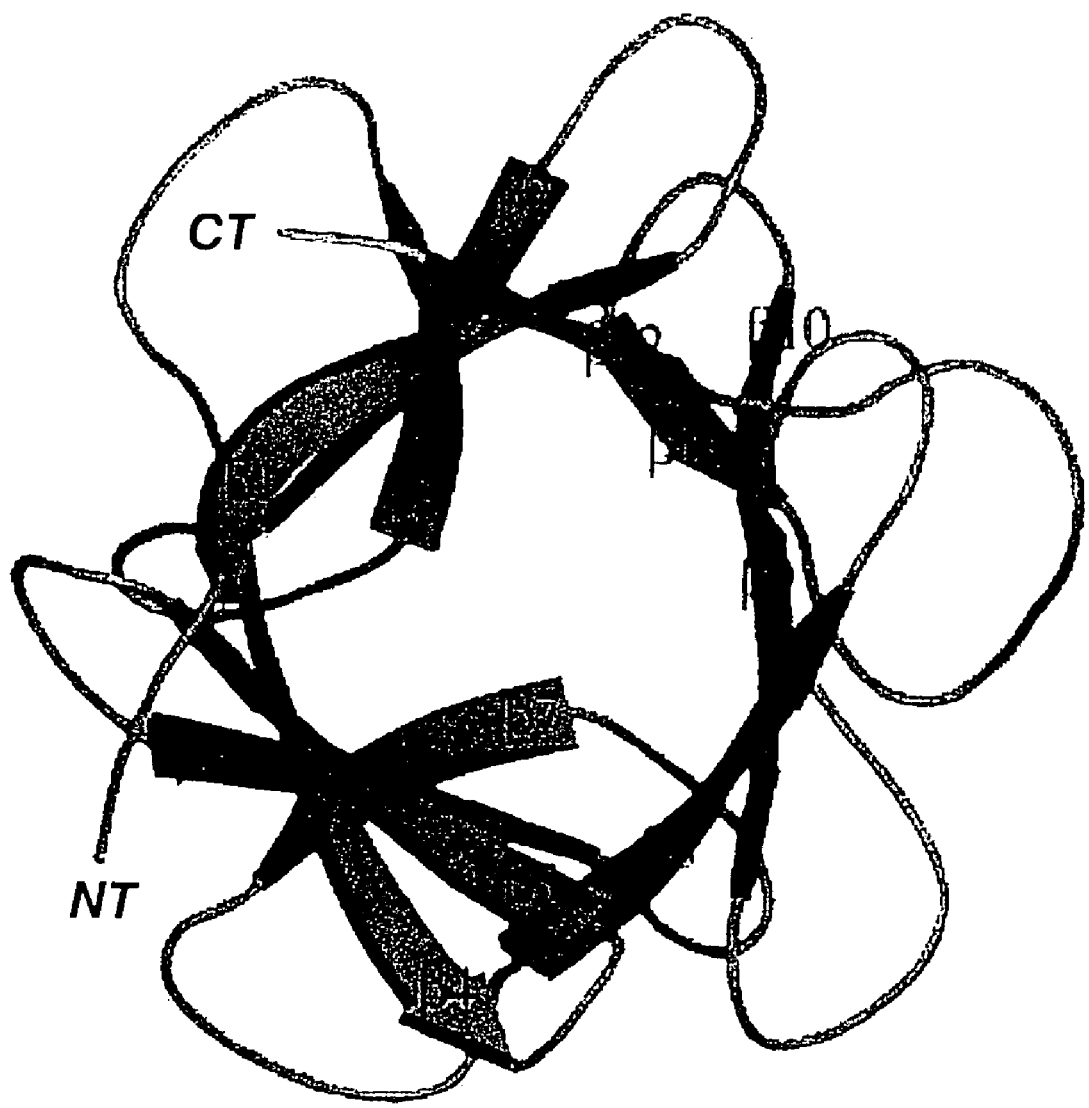

```
FGF4  MSGPGTAAVALLPAVLLALLAPWAGRGGAAAPTAPNGTLEAELERRWESLVALSLARLPVAAQPKEAAVQ
FGF6  MALGQKLFITMSRGAGR.QGT.WALVFL.ILVGMVV.SPAGTRANNTLID.RGWGT.LSRSR.GLAG.I.GV
FGF1                                                   M.EGEITTFTALTEKF
FGF2                                                   M.AGSITTLPALPEDG
```

```
         →1            →2         →3           →4         →5          →6
          *                                     *
FGF4 71  SGAGDYLLGIKRLRRLYCNVGGFHLQALPDGRIGGAHADT-RDSLLELSPVERGVVSIFGVASRFFVAMSS
FGF6 73  NWESG..V...Q.......V......S.TEEN-.Y.....I.T.........R.AL....N.
FGF1 17  N--LPPGNY.KPKL...SN.-.HF.RI...TVD.TRDRSDQHIQ.Q..AESV.E.Y.KSTETGQYL..DT
FGF2 17  GSGAFPPGHF..KN.-...F.RIH......VD.VREKSD.HIK.Q.QAE.......K..CANRYL..KE
```

```
         →7                    →8                →9        →10    →11        →12
          *                    **                 *         *      *         ** *         *  **
FGF4 142 KGKLYGSPFFTDECTFKEILLPNNYNAYESYKYPG--MFIALSKNGKTKKGNRVSPIMKVTHFLPRL
FGF6 144 ..R..AT.S.QE..K.R.T......F.Q..........DL.Q.-.TY.....Y.RV.R.SK....T....I
FGF1 85  D.L...QTPNE..L.R.EE.H....T.I.K.HAEKNW.VG.K...SC.R.P.THYGQ.AIL...LPVSSD
FGF2 88  D.R.LA.KCV......F.F.RES...T.R.R..TS--WYV..KRT.QY.L.SKTGGQ.AIL...MSAKS
```

Residues that Interact with D2

Figure 2B

Figure 2C

Amino Acid Residues that Constitute the
Conventional "Low" and "High" Affinity Heparin Binding Sites

```
FGF4  MSGPGTAAVALLPAVLLALLAPWAGRGGAAAPTAPNGTLEAELERRWESLVALSLARLPVAAQPKEAAVQ
FGF6  MALGQKLFITMSRGAGR.QGT.WALVFL.ILVGMVV.SPAGTRANNTLLD.RGWGT.LSRSR.GLAG.I.GV
FGF1                                                   M.EGEITTFTALTEKF
FGF2                                                   M.AGSITTLPALPEDG
```

⟨1⟩  ⟨2⟩  ⟨3⟩  ⟨4⟩  ⟨5⟩  ⟨6⟩

```
FGF4  71  SGAGDYLLGIKRLRRLYCNVGIGFHLQALPDGRIGGAHADT-RDSLLELSPVERGVVSIFGVASRFFVAMSS
FGF6  73  NWESG..V...Q...........V......S.T.EEN-.Y....I.T......R.AL....N.
FGF1  17  N---LPPGNY.KPKL...SN.-.HF.RI....TVD.TRDRSDQHIQ.Q..AESV.E.Y.KSTETGQYL..DT
FGF2  17  GSGAFPPGHF.DPK...KN.-..F.RIH......VD.VREKSD.HIK.Q.QAE.........K..CANRYL..KE
```

⟨7⟩  ⟨8⟩  ⟨9⟩  ⟨10⟩  ⟨11⟩  ⟨12⟩

```
FGF4  142 KGRLYGSPFFTDECTFKEILPNNYNAYESYKYPG--MFIALSKNGKTKGNRVSPTMKVTHFLPRL
FGF6  144 ..R..AT.S.QE..K.R.T..............DL.Q.--TY....Y.RV.R.SK..I.T......I
FGF1  85  D.L...QTPNE..L.L.R.EE.H..T.I.K.HAEKNW.VG.K...SC.R.P.THYGQ.AIL...LPVSSD
FGF2  88  D.R.LA.KCV....F.F.R.ES....T.R.R..TS--WYV..KRT.QY.L.SKTG.GQ.AIL...MSAKS
```

FGF4 Amino Acid Residues that Localize to the Periphery of the "High" Affinity Heparin Binding Site

Figure 2D

```
FGF4    MSGPGTAAVALLPAVLLALLAPWAGRGGAAAPTAPNGTLEAELERRWESIVALSLARLPVAAQPKEAAVQ
FGF6    MALGQKLFITMSRGAGR.QGT.WALVFL.ILVGMVV.SPAGTRANNTLLD.RGWGT.LSRSR.GLAG.I.GV
FGF1                                                            M.EGEITTFTALTEKF
FGF2                                                            M.AGSITTLPALPEDG
```

→1      →2     →3      →4     →5      →6

```
FGF4  71  SGAGDYLLGIKRLRRLYCNVGIGFHLQALPDGRIGGAHADT-RDSLLELSPVERGVVSIEGVASRFFVAMSS
FGF6  73  NWESG..V....Q..........V....S.T.EEN-.Y....IIT.........R.AL....N.
FGF1  17  N--LPPGNY.KPKL...SN.-.HF.RI....TVD.TRDRSDQHIQ.Q..AESV.E.Y.KSTETGQYL..DT
FGF2  17  GSGAFPPGHF..DPK....KN.-..F.RIH....VD.VREKSD.HIK.Q.QAE........K..CANRYL..KE
```

→7     →8     →9     →10    →11     →12

```
FGF4 142  KGKLYGSPFFTDECTFKEILLPNNYNAYESYKYPG--MFIALSKNGKTKKGNRVSPTMKVTHFLPRL
FGF6 144  ..R..AT.SQE..K.R.T.........DL.Q..--TY....Y.RV.R.SK...I.T......I
FGF1  85  D.L....QTPNE...L.L.R.EE.H..T.I.K.HAEKNW.VG.K...SC.R.P.THYGQ.AIL...LPVSSD
FGF2  88  D.R.LA.KCV.....F.F.R.ES....T.R.R...TS--WYV..KRT.QY.L.SKTG.GQ.AIL...MSAKS
```

FGFR Residues that Interact with the
βC'- βE Loop in the FGFR1 D3 Domain

Figure 2E

```
FGF4    MSGPGTAAVALLPAVLLALLAPWAGRGGAAAPTAPNGTLEAELERRWESLVALSLARLPVAAQPKEAAVQ
FGF6    MALGQKLFITMSRGAGR.QGT.WALVFL.ILVGMVV.SPAGTRANNTLLD.RGWGT.LSRSR.GLAG.I.GV
FGF1                                                            M.EGEITTFTALTEKF
FGF2                                                            M.AGSITTLPALPEDG
```

[arrows labeled 1  2  3  4  5  6]

```
FGF4    71   SGAGDYLLGIKRLRRLYCNVGIGFHLQALPDGRIGGAHADT-RDSLLELSPVERGVVSIFGVASRFFVAMSS
FGF6    73   NWESG..V...Q........V......S.T.EEN-.Y....I.T.........R.AL......N.
FGF1    17   N---LPPGNY.KPKL...SN.-.HF.RI....TVD.TRDRSDQHIQ.Q..AESV.E.Y.KSTETGQYL..DT
FGF2    17   GSGAFPPGHF.DPK....KN.-...F.RIH....VD.VREKSD.HIK.Q.QAE........K..CANRYL..KE
```

[arrows labeled 7  8  9  10  11  12]

```
FGF4    142  KGKLYGSPFFTDECTFKEILPNNYAYESYKYPG--MFIALSKNGKTKKGNRVSPTMKVTHFLPRL
FGF6    144  ..R..AT.S.QE..K.R.T.........DL.Q.--TY....Y.RV.R.SK..I.T.......I
FGF1    85   D.L....QTPNE...L.L.REE.H...T.I.K.HAEKNW.VG.K...SC.R.P.THYGQ.AIL...IPVSSD
FGF2    88   D.R.LA.KCV.....F.F.RES......T.R.R..TS--WYV..KRT.QY.L.SKTG.GQ.AIL..MSAKS
```

Residues that Interact with FGFR1 Linker Region

Figure 2F

```
FGF4  MSGPGTAAVALLPAVLLALLAPWAGRGGAAAPTAPNGTLEAELERRWESLVALSLARLPVAAQPKEAAVQ
FGF6  MALGQKLFITMSRGAGR.QGT.WALVFL.ILVGMVV.SPAGTRANNTLLD.RGWGT.LSRSR.GLAG.I.GV
FGF1                                                              M.EGEITTFTALTEKF
FGF2                                                              M.AGSITTLPALPEDG
```

1           2           3           4           5           6

```
FGF4    SGAGDYLLG KRLRRL CNVG  GFH LQALPDGRIGGA ADT-RDSLL  SPVERG VSI GVASRF VAMSS
FGF6 71 NWESG..V. ...Q.. ....  ... .V......S.T EEN-.Y...  ..R.AL .... ...R.AL ....N.
FGF1 73 N--LPPGNY. KPKL.. .SN-  .HF .RI....TVD.TRDRSDQHIQ.Q. .AESV E.Y. KSTETGQYL..DT
FGF2 17 GSGAFPPGHF ..DPK. .KN-  ..F .RIH....VD.VREKSD.HIK.Q.QAE... ..K.. CANRYL..KE
        17
```

7           8           9          10          11          12

```
FGF4     KGKLYGSPF TDECTFK HI LPNN  NAYESYKYPG--MFIALSKNGKTKKGNRVSPTMKVTHF LPRL
FGF6 142 ..R..AT.S QE..K.R T...  .....DL.Q.--TY.....Y.RV.R.SK...IT...    .I..
FGF1 144 D.L..QTPNE ..L.CR EE .HT .IK.HAEKNW..VG.K...SC.R.P.THYGQ.AIL... IPVSSD
FGF2  85 D.R.LA.KCV ...F.  FR .ES ...T.R.R..TS--WYV..KRT.QY.L.SKTG.GQ.AIL .MSAKS
      88
```

Primary Binding Site

Figure 7B

```
                   MSGPGTAAVALLPAVLLALLAPWAGRGGAAAPTAPNGTLEAELERRWESLVAISLARLPVAAQPKEAAVQ
FGF4
FGF6               MALGQKLFITMSRGAGR.QGT.WALVFL.ILVGMVV.SPAGTRANNTLLD.RGWGT.LSRSR.GLAG.I.GV
FGF1                                                                     M.EGEITTFTALTEKF
FGF2                                                                     M.AGSITTLPALPEDG 1          2         3         4          5         6
                  ↑          ↑         ↑         ↑          ↑         ↑
                  *          *         *                    *
FGF4    71   SGAGDYLLGIKRLRRLYCNVGIGFHLQALPDGRIGGAHADT-RDSLLELSPVERGVVSIFGVASRFFVAMSS
FGF6    73   NWESG..V....Q..............V........S.T.EEN-.Y.....I.T........R.AL......N.
FGF1    17   N---LPPGNY.KPKL....SN.-.HF.RI.....TVD.TRDRSDQHIQ.Q..AESV.E.Y.KSTETGQYL..DT
FGF2    17   GSGAFPPPGHF.DPK.....KN.-..F.RIH.....VD.VREKSD.HIK.Q.QAE.........K..CANRYL..KE 7          8         9         10        11        12
                  ↑          ↑         ↑         ↑         ↑         ↑
                  *         ** *       *          *           **  *  *   *
FGF4   142   KGKLYGSPFFTDECTFKEILNNYNAYESYKYPG--MFIALSKNGKTKKGNRVSRMKVTHFLPRL
FGF6   144   ..R..AT.S.QE...K.R.T.............DL.Q.-.TY.....Y..RV.R.SK...I.T....I
FGF1    85   D.L.....QTPNE...L.L.R.EE.H..T.I.K.HAEKNW.VG.K...SC.R.P.THYGQ.AIL...LPVSSD
FGF2    88   D.R.LA.KCV.....F.F.R.ES....T.R.R..TS--WYV..KRT.QY.L.SKTG.GQ.AIL...MSAKS
```

Secondary Binding Site

Figure 8B

```
FGF4  MSGPGTAAVALLPAVLLALLAPWAGRGGAAAPTAPNGTLEAELERRWESLVALSLARLPVAAQPKEAAVQ
FGF6  MALGQKLFITMSRGAGR.QGT.WALVFL.ILVGMVV.SPAGTRANNTLLD.RGWGT.LSRSR.GLAG.I.GV
FGF1                                                     M.EGEITTFTALTEKF
FGF2                                                     M.AGSITTLPALPEDG
```

```
         ⇧1              ⇧2          ⇧3         ⇧4          ⇧5         ⇧6
FGF4  71  SGAGDYLLGIKRLRRLYCNVGIGFHLQALPDGRIGGAHADT-RDSLLELSPVERGVVSIFGVASRFFVAMSS
FGF6  73  NWESG.V....Q......................V......S.T.EEN-.Y......I.T.......R.AL..N.
FGF1  17  N--LPPGNY.KPKL............HF.RI......TVD.TRDRSDQHIQ.Q..AESV.E.Y.KSTETGQYL..DT
FGF2  17  GSGAFPPGHF....DPK....KN.-..F.RIH.....VD.VREKSD.HIK.Q.QAE.......K..CANRYL..KE

⇧7         ⇧8             ⇧9          ⇧10          ⇧11            ⇧12
              *           **                *              *        *    ** *
FGF4 142  KGKLYGSPFFTDECTFKEILLPNNYNAYESYKYPG--MFIALSKNGKTKKGNRVSPTMKVTHFLPRL.......I
FGF6 144  ...R..AT.S.QE..K.R.T...........DL.Q.-.TY....AY..RV.R.SK....ITE............
FGF1  85  D.L....QTPNE..L.L.R.EE.H..T.I.K.HAEKNW.VG.K...SC.R.P.THYGQ.AIL....LPVSSD
FGF2  88  D.R..LA.KCV....F.F.R.ES....T.R.R..TS--WYV..KRT.QYL.SKTG.GQ.AIL...MSAKS
```

Heparin Binding Site

Figure 9B

SEQUENCE LISTING

<160> NUMBER OF SEQ ID NOS: 23

<210> SEQ ID NO 1
<211> LENGTH: 39
<212> TYPE: DNA
<213> ORGANISM: Artificial sequence
<220> FEATURE:
<223> OTHER INFORMATION: mutant oligo primer

<400> SEQUENCE: 1
aagcggctgc ggcggctcgc atgcaacgtg ggcatcggc                                   39

<210> SEQ ID NO 2
<211> LENGTH: 32
<212> TYPE: DNA
<213> ORGANISM: Artificial sequence
<220> FEATURE:
<223> OTHER INFORMATION: mutant oligo primer

<400> SEQUENCE: 2
gcgtggtgag catcgccggc gtggccagcc gg                                          32

<210> SEQ ID NO 3
<211> LENGTH: 37
<212> TYPE: DNA
<213> ORGANISM: Artificial Sequence
<220> FEATURE:
<223> OTHER INFORMATION: mutant oligo primer

<400> SEQUENCE: 3
ctatggctcg cccttcgcga ccgatgagtg cacgttc                                     37

<210> SEQ ID NO 4
<211> LENGTH: 36
<212> TYPE: DNA
<213> ORGANISM: Artificial sequence
<220> FEATURE:
<223> OTHER INFORMATION: mutant oligo primer

<400> SEQUENCE: 4
gatgagtgca cgttcaaggc cattctcctt cccaac                                      36

<210> SEQ ID NO 5
<211> LENGTH: 33
<212> TYPE: DNA
<213> ORGANISM: Artificial Sequence
<220> FEATURE:
<223> OTHER INFORMATION: mutant oligo primer

<400> SEQUENCE: 5
ctccttccca acaacgcgaa cgcgtacgag tcc                                         33

<210> SEQ ID NO 6
<211> LENGTH: 38
<212> TYPE: DNA
<213> ORGANISM: Artificial sequence
<220> FEATURE:
<223> OTHER INFORMATION: mutant oligo primer

<400> SEQUENCE: 6
ccatgaaggt cacccacttc gccctaggc tgtgaccc                                     38

<210> SEQ ID NO 7
<211> LENGTH: 34

```
<212> TYPE: DNA
<213> ORGANISM: Artificial sequence
<220> FEATURE:
<223> OTHER INFORMATION: mutant oligo primer

<400> SEQUENCE: 7
cccacttcct ccccgcgctg tgaccttcca gagg                              34

<210> SEQ ID NO 8
<211> LENGTH: 33
<212> TYPE: DNA
<213> ORGANISM: Artificial Sequence
<220> FEATURE:
<223> OTHER INFORMATION: mutant oligo primer

<400> SEQUENCE: 8
cggcggctct actgcgccgt gggcatcggc ttc                               33

<210> SEQ ID NO 9
<211> LENGTH: 33
<212> TYPE: DNA
<213> ORGANISM: Artificial Sequence
<220> FEATURE:
<223> OTHER INFORMATION: mutant oligo primer

<400> SEQUENCE: 9
gtgtcgccca ccatggcggt cacccacttc ctc                               33

<210> SEQ ID NO 10
<211> LENGTH: 36
<212> TYPE: DNA
<213> ORGANISM: Artificial Sequence
<220> FEATURE:
<223> OTHER INFORMATION: mutant oligo primer

<400> SEQUENCE: 10
gccctgagcg cgaatgggaa gaccgcgaag gggaac                            36

<210> SEQ ID NO 11
<211> LENGTH: 33
<212> TYPE: DNA
<213> ORGANISM: Artificial Sequence
<220> FEATURE:
<223> OTHER INFORMATION: mutant oligo primer

<400> SEQUENCE: 11
gcgctccccg acggcgccat cggcggcgcg cac                               33

<210> SEQ ID NO 12
<211> LENGTH: 33
<212> TYPE: DNA
<213> ORGANISM: Artificial Sequence
<220> FEATURE:
<223> OTHER INFORMATION: mutant oligo primer

<400> SEQUENCE: 12
atgagcagca agggcgcgct ctatggctcg ccc                               33

<210> SEQ ID NO 13
<211> LENGTH: 36
<212> TYPE: DNA
<213> ORGANISM: Artificial Sequence
<220> FEATURE:
<223> OTHER INFORMATION: mutant oligo primer

<400> SEQUENCE: 13
```

-continued

```
gccctgagcg cgaatgggaa gaccgcgaag gggaac                         36
```

<210> SEQ ID NO 14
<211> LENGTH: 33
<212> TYPE: DNA
<213> ORGANISM: Artificial Sequence
<220> FEATURE:
<223> OTHER INFORMATION: mutant oligo primer

<400> SEQUENCE: 14

```
cgcgacagcc tgctggcgct ctcgcccgtg gag                            33
```

<210> SEQ ID NO 15
<211> LENGTH: 32
<212> TYPE: DNA
<213> ORGANISM: Artificial Sequence
<220> FEATURE:
<223> OTHER INFORMATION: mutant oligo primer

<400> SEQUENCE: 15

```
ttcaaggaga ttctcgctcc caacaactac aa                             32
```

<210> SEQ ID NO 16
<211> LENGTH: 31
<212> TYPE: DNA
<213> ORGANISM: Artificial Sequence
<220> FEATURE:
<223> OTHER INFORMATION: mutant oligo primer

<400> SEQUENCE: 16

```
accatgaagg tcaccgcctt cctcccaggc t                              31
```

<210> SEQ ID NO 17
<211> LENGTH: 31
<212> TYPE: DNA
<213> ORGANISM: Artificial Sequence
<220> FEATURE:
<223> OTHER INFORMATION: mutant oligo primer

<400> SEQUENCE: 17

```
ggagattctc cttgccaaca actacaacgc c                              31
```

<210> SEQ ID NO 18
<211> LENGTH: 33
<212> TYPE: DNA
<213> ORGANISM: Artificial Sequence
<220> FEATURE:
<223> OTHER INFORMATION: mutant oligo primer

<400> SEQUENCE: 18

```
gggaaccgag tgtcggccac catgaaggtc acc                            33
```

<210> SEQ ID NO 19
<211> LENGTH: 39
<212> TYPE: DNA
<213> ORGANISM: Artificial sequence
<220> FEATURE:
<223> OTHER INFORMATION: mutant oligo primer

<400> SEQUENCE: 19

```
gggaaccgag tgtcgccgcc atgaaggtca cccacttcc                      39
```

<210> SEQ ID NO 20
<211> LENGTH: 206
<212> TYPE: PRT
<213> ORGANISM: homo sapiens

<400> SEQUENCE: 20

```
Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
                20                  25                  30

Thr Ala Pro Asn Gly Thr Leu Glu Ala Glu Leu Glu Arg Arg Trp Glu
                35                  40                  45

Ser Leu Val Ala Leu Ser Leu Ala Arg Leu Pro Val Ala Ala Gln Pro
50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
                100                 105                 110

Asp Ser Leu Leu Glu Leu Ser Pro Val Glu Arg Gly Val Val Ser Ile
                115                 120                 125

Phe Gly Val Ala Ser Arg Phe Phe Val Ala Met Ser Ser Lys Gly Lys
            130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
                180                 185                 190

Val Ser Pro Thr Met Lys Val Thr His Phe Leu Pro Arg Leu
                195                 200                 205
```

<210> SEQ ID NO 21
<211> LENGTH: 208
<212> TYPE: PRT
<213> ORGANISM: homo sapiens

<400> SEQUENCE: 21

```
Met Ala Leu Gly Gln Lys Leu Phe Ile Thr Met Ser Arg Gly Ala Gly
1               5                   10                  15

Arg Leu Gln Gly Thr Leu Trp Ala Leu Val Phe Leu Gly Ile Leu Val
                20                  25                  30

Gly Met Val Val Pro Ser Pro Ala Gly Thr Arg Ala Asn Asn Thr Leu
                35                  40                  45

Leu Asp Ser Arg Gly Trp Gly Thr Leu Leu Ser Arg Ser Arg Ala Gly
50                  55                  60

Leu Ala Gly Glu Ile Ala Gly Val Asn Trp Glu Ser Gly Tyr Leu Val
65                  70                  75                  80

Gly Ile Lys Arg Gln Arg Arg Leu Tyr Cys Asn Val Gly Ile Gly Phe
                85                  90                  95

His Leu Gln Val Leu Pro Asp Gly Arg Ile Ser Gly Thr His Glu Glu
                100                 105                 110

Asn Arg Tyr Ser Leu Leu Glu Ile Ser Thr Val Glu Arg Gly Val Val
                115                 120                 125

Ser Ile Phe Gly Val Arg Ser Ala Leu Phe Val Ala Met Asn Ser Lys
                130                 135                 140

Gly Arg Leu Tyr Ala Thr Pro Ser Phe Gln Glu Glu Cys Lys Phe Arg
145                 150                 155                 160
```

```
Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
            180                 185                 190

Ser Lys Val Ser Pro Ile Met Thr Val Thr His Phe Leu Pro Arg Ile
        195                 200                 205

<210> SEQ ID NO 22
<211> LENGTH: 155
<212> TYPE: PRT
<213> ORGANISM: homo sapiens

<400> SEQUENCE: 22

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 23
<211> LENGTH: 155
<212> TYPE: PRT
<213> ORGANISM: homo sapiens

<400> SEQUENCE: 23

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Arg His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125
```

```
Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145             150                 155
```

IDENTIFICATION OF RECEPTOR AND HEPARIN BINDING SITES IN FGF4 BY STRUCTURE-BASED MUTAGENESIS

This application is a continuation of PCT/US02/24274 filed Aug. 1, 2002 and claims priority under 35 U.S.C. 119 (e) from Provisional Application No. 60/309,431, filed Aug. 1, 2001, incorporated herein by reference in its entirety.

This invention as made with Government support under Grant Nos. DE13686 and CA42568 awarded by the National Institutes of Health. The United States Government may have certain rights to this invention pursuant to the terms of those grants.

1. FIELD OF THE INVENTION

The present invention relates to a class of proteins known as fibroblast growth factor (FGF) proteins or FGF ligands. The invention also relates to receptors, known as fibroblast growth factor receptors (FGFRs), that recognize and specifically bind to FGF proteins. The invention further relates to a particular FGF polypeptide, referred to as FGF4. The methods and compositions of the invention relate to novel methods and compositions, including novel polypeptides and other compounds, that modulate FGF binding to its receptor and may be used, e.g., as agonists or antagonists to modulate FGF receptor activity and/or biological activities that are associated with FGF.

2. BACKGROUND OF THE INVENTION

The fibroblast growth factor (FGF) family of proteins comprises at least 22 polypeptides, referred to as FGF1-FGF22, with diverse biological activities. For reviews, see, McKeehan et al., *Prog. Nucleic Acid Res. Mol. Biol.* 1998, 59:135-176; Nishimura et al., *Biochim Biophys. Acta.* 2000, 1492:203-206; Yamashita et al., *Biochem. Biophys. Res. Commun.* 2000, 277:494-498. For example, FGF polypeptides modulate the proliferation and differentiation of a variety of cells of mesenchymal and neuro-ectodermal origin (Basilico & Moscatelli, *Adv. Cancer Res.* 1992, 59:115-165). FGF polypeptides also play critical roles during embryonic processes such as mesoderm induction, post-implantation blastocyst development, and limb and lung development (Goldfarb, *Cytokine Growth Factor Rev.* 1996, 7:311-325; Xu et al., *Cell Tissue Res.* 1999, 296:33-43). Increased FGF signaling leads to a variety of human skeletal disorders, including dwarfism and craniosynostosis syndromes (McIntosh et al., *Cell Struct. Funct.* 2000, 25:85-96; Naski & Ornitz, *Front. Biosci.* 1998, 3:D781-D794; Wilkie, *Hum. Mol. Genet.* 1997, 6:1647-1656). In adult organisms FGFs are thought to be involved in physiological angiogenesis and wound healing as well as in pathological angiogenesis such as in tumor neovascularization and diabetic retinopathy (Basilico & Moscatelli, *Adv. Cancer Res.* 1992, 59:115-165).

The diverse effects of FGFs are mediated by at least four receptor tyrosine kinases, which are referred to collectively as the FGF receptor (FGFR) polypeptides and are known individually as FGFR1-FGFR4. The FGFR polypeptides comprise an extracellular domain, a single transmembrane helix and a cytoplasmic portion. The extracellular domain binds to the FGF polypeptide ligand, and may be subdivided into at least three distinct three immunoglobulin (Ig)-like domains, known as D1-D3, with each domain being connected by a "linker" polypeptide sequence. Ligand binding and specificity resides in the D2 and D3 domains and the short D2-D3 linker (Plotnikov et al., *Cell* 1999, 98:641-650; Plotnikov et al., *Cell* 2000, 101:413-424; Stauber et al., *Proc. Natl. Acad. Sci. U.S.A.* 2000, 97:49-54).

FGFR dimerization is prerequisite for FGF signaling and requires heparin or heparan sulfate proteoglycans (HSPG) (Ornitz, *Bioessays* 2000, 22:108-112; Schlessinger, *Cell* 2000, 103:211-225). The recent crystal structure of a ternary FGF2-FGFR1-heparin complex has provided a mechanistic view of the process by which heparin aids FGF polypeptides to induce FGFR dimerization (Schlessinger et al., *Mol. Cell* 2000, 6:743-750). According to this "two end" model, heparin interacts via its non-reducing end with the heparin binding sites of FGF and FGFR and promotes the formation of a ternary 1:1:1 FGF:FGFR:heparin complex. A second ternary 1:1:1 FGF:FGFR:heparin complex is then recruited to the first ternary complex via interactions of FGFR, FGF and heparin in one ternary complex with the FGFR in the adjoining ternary complex.

A fundamentally different model for FGFR dimerization has emerged from the recent crystal structure of a dimeric FGF1-FGFR2-heparin ternary complex (Pellegrini et al., *Nature* 2000, 407:1029-1034). In this structure, a single heparin molecule links two FGF ligands into a dimer that bridges between two receptor chains. The asymmetric heparin binding involves contacts with both FGF molecules but only one receptor chain. There is essentially no protein-protein interface between the two 1:1 FGF-FGFR complexes in the dimer.

With the exception of FGF1, which is the universal ligand for all FGFRs, most FGF polypeptides exhibit specific, albeit promiscuous, patterns of receptor binding affinity (Ornitz et al., *J. Biol. Chem.* 1996, 271:15292-15297). Comparison of the crystal structures of FGF1-FGFR1, FGF2-FGFR1 and FGF2-FGFR2 complexes defined a general binding interface for FGF-FGFR complexes involving contacts made by FGF to D2 and to the D2-D3 linker (Plotnikov et al., *Cell* 2000, 101:413-424). It has also been shown that specificity is achieved through interactions of the FGF N-terminal (i.e., the amino acid sequence immediately preceding the FGF polypeptide's β-trefoil core domain) and central regions with FGFR D3. These structures have also provided a molecular basis for how alternative splicing in FGFR modulates specificity. In both FGF2-FGFR1 and FGF2-FGFR2 structures, FGF2 makes specific contacts with the βC'-βE loop in D3, which is subject to alternative splicing. Consequently, FGF2 discriminates between the IIIc and IIIb variants of FGFRs. In contrast, FGF1 does not interact with the βC'-βE loop and therefore can bind all FGFRs irrespective of alternative splicing in D3 (Plotnikov et al., *Cell* 2000, 101:413-424).

FGF4 shares about 30% sequence identity with the prototypical members of the FGF family, FGF1 and FGF2 (Delli Bovi et al., *Cell* 1987, 50:729-737). FGF4, unlike FGF1 and FGF2, has a classical signal peptidp and thus is efficiently secreted from cells (Bellosta et al., *J. Cell Biol.* 1993, 121:705-713). Most receptor binding studies indicate that FGF4 binds and activates the IIIc splice forms of FGFR1-3 to comparable levels, but it shows little activity towards the IIIb splice forms of FGFR1-3 as well as towards FGFR4 (Ornitz et al., *J. Biol. Chem.* 1996, 271:15292-15297; Vainikka et al., *EMBO J.* 1993, 11:4273-4280). As for FGF1 and FGF2, heparin greatly augments the biological activity of FGF4 on cells lacking endogenous cell surface HSPG (Mansukhani et al., *Proc. Natl. Acad. Sci. U.S.A.* 1992, 89:3305-3309). However, employing selectively O-desulfated heparins, Guimond et al. (*J. Biol. Chem.* 1993, 268:23906-23914) have shown that both 2-O-and 6-O- desulfated heparin were able to support the mitogenic activity of FGF4, while neither of these heparins could support the biological activity of FGF1 and FGF2. It has therefore been suggested the sulfation motifs in heparin required for FGF4 activity may differ from those required for FGF1 and FGF2 actions (Guimond et al., supra; Ishihara, *Glycobiology* 1994, 4:817-824).

In summary, the exact interactions that stabilize complexes of the FGF4 polypeptide with its receptor and/or heparin remain poorly understood. Yet, given the range of biological disorders associated with FGF signaling, there is an urgent need to identify and characterize these interactions. There exist, moreover, a need to identify compounds that modulate binding of FGF4 to either an FGF receptor or heparin, including mutant or variant forms of the FGF4 polypeptide that have altered binding affinities, as well as other compounds that may be agonists or antagonists of FGF4 binding and/or activity.

3. SUMMARY OF THE INVENTION

The present invention provides mutant FGF4 polypeptides, wherein at least one amino acid residue in the primary binding site, the secondary binding site or the heparin binding site is different from the wild-type FGF4 molecule.

In preferred embodiments, the invention provides the following mutant FGF4 polypeptides, each containing the substitution at the indicated residue with alanine: tyrosine at amino acid residue 87; phenylalanine at amino acid residue 129; phenylalanine at amino acid residue 151; glutamic acid at amino acid residue 159; phenylalanine at amino acid residue 166; leucine at amino acid residue 203; arginine at amino acid residue 205; asparagine at amino acid residue 89; lysine at amino acid residue 198; asparagine at amino acid residue 89; lysine at amino acid residue 183; lysine at amino acid residue 188; lysine at amino acid residue 183; arginine at amino acid residue 103; lysine at amino acid residue 144; and arginine at amino acid residue 103.

In another preferred embodiment, the invention provides a mutant FGF4 polypeptide containing two alanine substitutions at lysine residue 144 and arginine residue 103.

The invention further provides a crystal of FGF4, the crystal belonging to the orthorhombic space group P212121 and having unit cell dimensions a=40.37, b=53.3 and c=56.23.

Figure 2A:
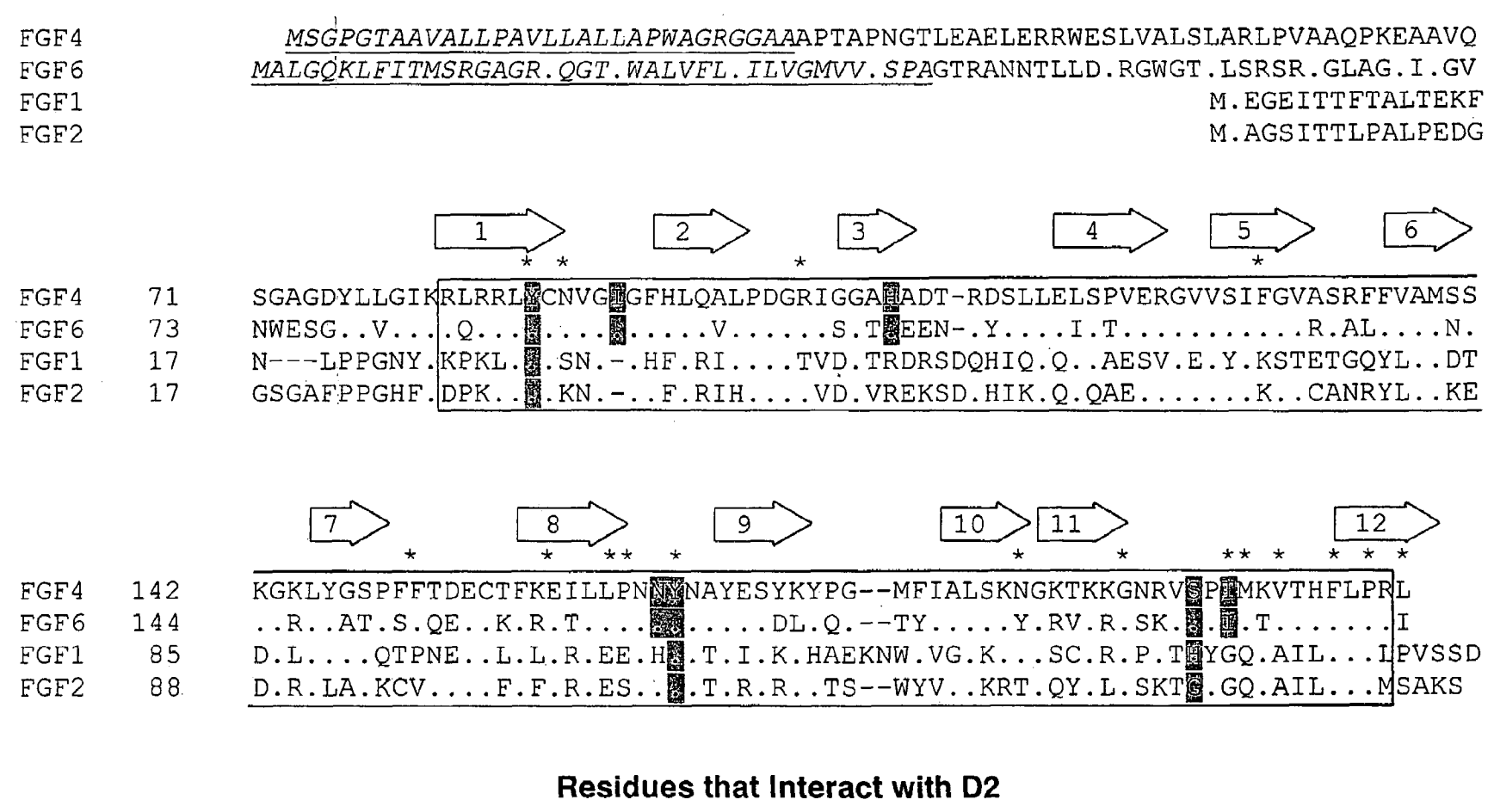
Figure 2C:
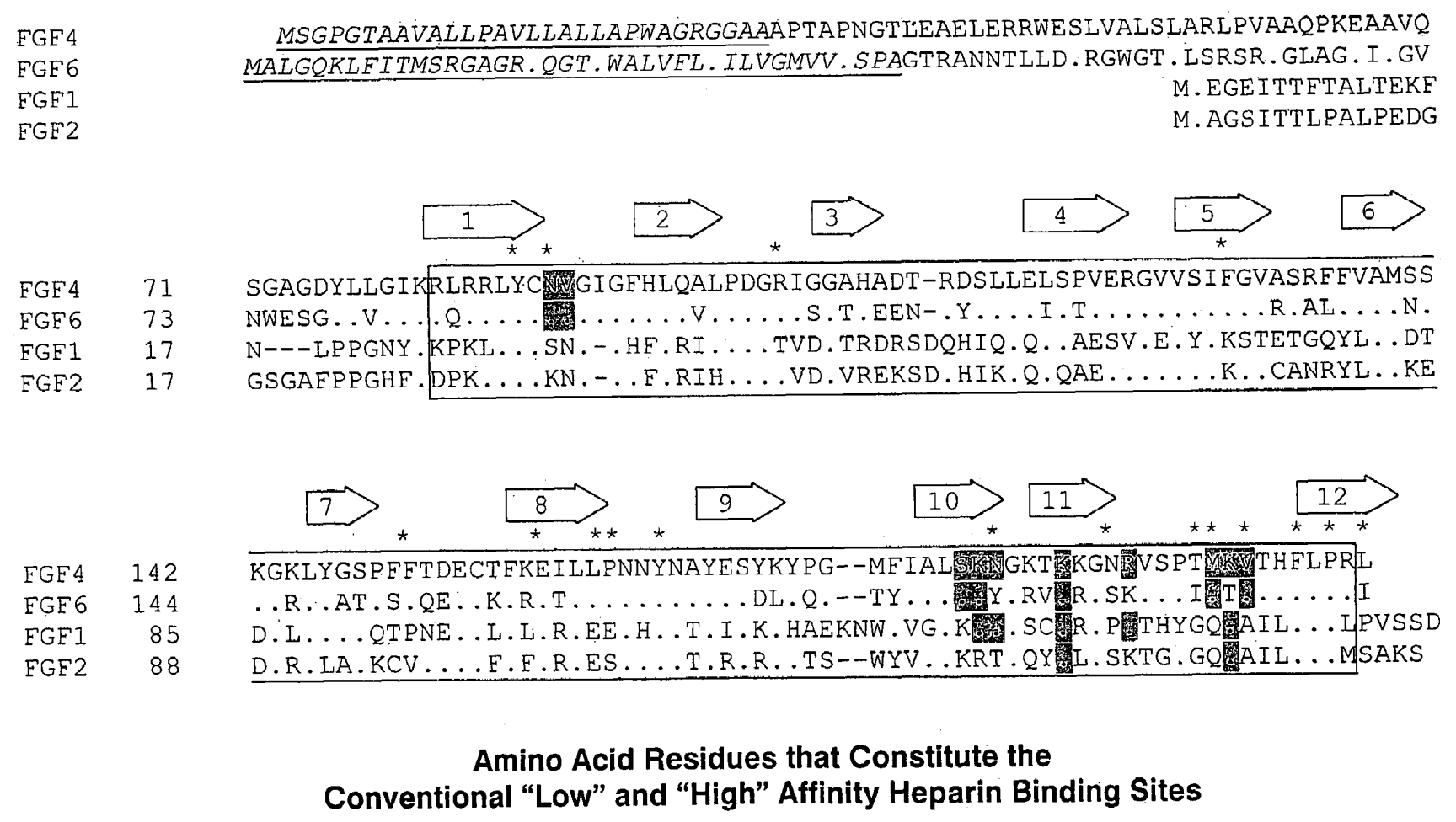

In a preferred embodiment, the crystal comprises an FGF4 polypeptide having the amino acid sequence depicted in FIG. 2 (top line).

The present invention also provides a method for producing mutant FGF4 polypeptides, and methods of testing mutant FGF4 polypeptides for increased or decreased binding and/or activity.

Crystalline forms of FGF4 are also provided by the present invention.

4. BRIEF DESCRIPTION OF THE DRAWINGS

FIG. 1 is a ribbon diagram illustrating the tertiary structure for an FGF4 polypeptide whose amino acid sequence is set forth in FIG. 2, below. The secondary structure assignments were assigned using the program PRODCHECK (Laskowski et al., *J. Appl. Cryst.* 1993, 26:283-291), and the figure created using the programs Molscript (Kraulis, *J. Appl. Crystallogr.* 1991, 24:946-950) and Raster3D (Merritt & Bacon, *Methods Enzymol.* 1997, 277:505-524). β-strands are labeled according to conventional strand nomenclature for FGF1 and FGF2 (see, Faham, *Curr. Opin. Struct. Biol.* 1998, 8:578-586). NT and CT denote the amino- and carbyoxy-termini, respectfully.

FIG. 2A-F provides a structure based sequence alignment of the FGF4 polypeptide amino acid sequence (top line) whose structure is illustrated in FIG. 1A, and related human FGF polypeptides FGF6, FGF1 and FGF2. The alignment was generated using the program CLUSTALW (Stauber et al., *Proc. Natl. Acad. Sci. U.S.A.* 2000, 97:49-54). The location and length of the β-strands and α-helices of the proteins' structures are indicated on top of the alignment, and the box indicates boundaries of the β-trefoil core region or domain. Periods in the aligned sequences indicated amino acid residues that are identical to the amino acid residue of FGF4 at that position of the alignment, whereas dashes represent gaps introduced to optimize the alignment. Residues with the β-trefoil core region are labeled to indicate the region of FGFR1 with which they interact: residues that interact with D2 are shaded (2B), residues that interact with the FGFR1 linker region (2F), residues that interact with the D3 domain of FGFR1 (2A), and FGFR residues that interact with the βC'-βE loop in the FGFR1 D3 domain are also shaded (2E). Also, amino acid residues that constitute the conventional "low" and "high" affinity heparin binding sites (2C) and FGF4 amino acid residues that localize to the periphery of the "high" affinity heparin binding site (and may, therefore interact with heparin-2D) are also indicated. A star indicates those amino acid residues that are tested in the Examples, infra, by site-directed mutagenesis.

Figure 3:
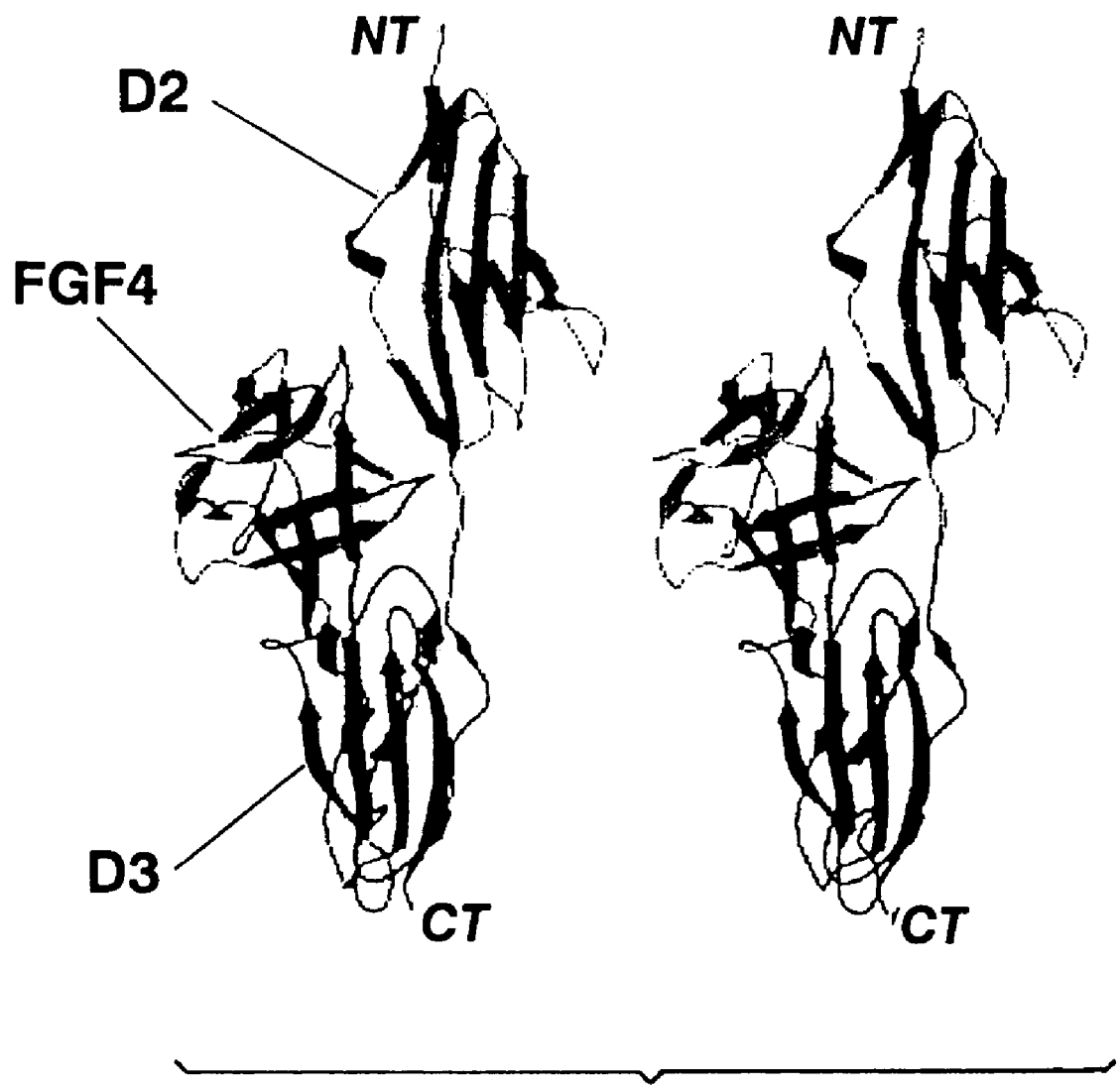

FIG. 3 provides a representative model (generated using the Molscript and Raster3D programs) for the three-dimensional structure of an FGF4-FGFR1 complex generated by superimposition of Cα traces within the β-trefoil of a structure for unbound FGF4 onto corresponding Cα traces of FGF2 in a structure for an FGF2-FGFR1 complex (see the Examples, infra). FGF4, D2 of FGFR1, D3 of FGFR1, and the D2-D3 are labeled. NT and CT denote the amino- and carboxy-termini, respectfully.

Figure 4:
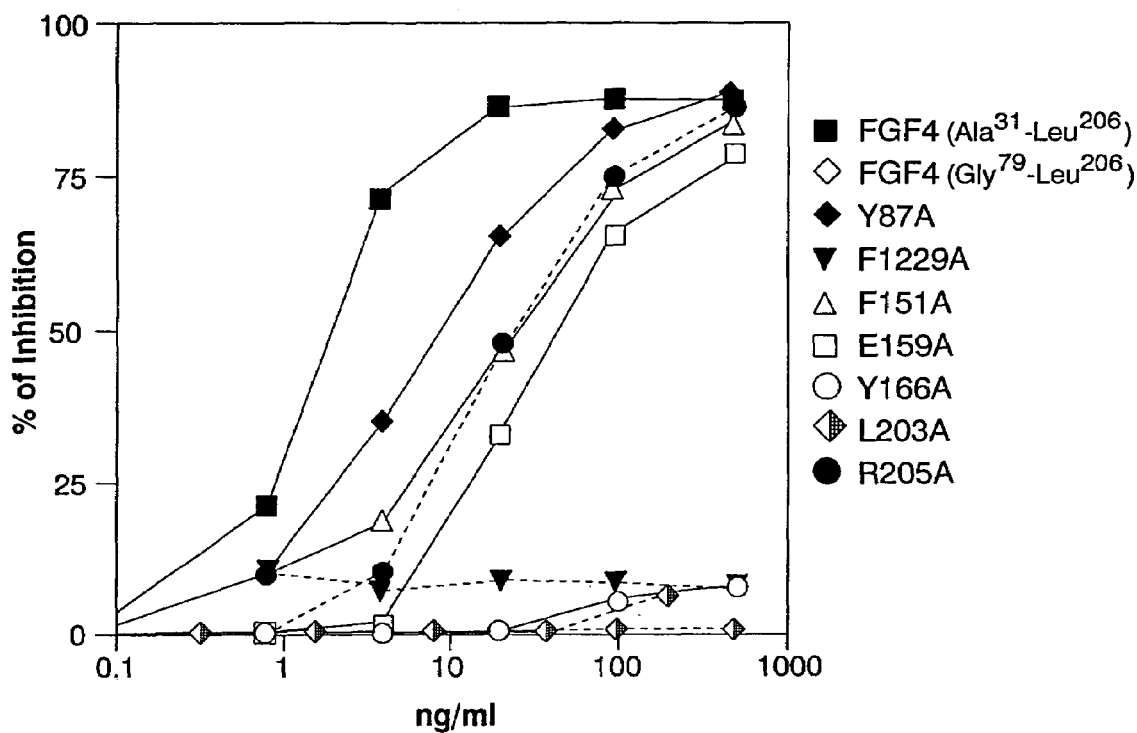

FIG. 4 shows a plot comparing the binding affinities of various FGF4 mutants twoards FGFP2 Data are expressed as percent inhibition of wild-type FGF4 binding to FGFR2 by the indicated amount of unlabeled mutant FGF4.

Figure 5A:
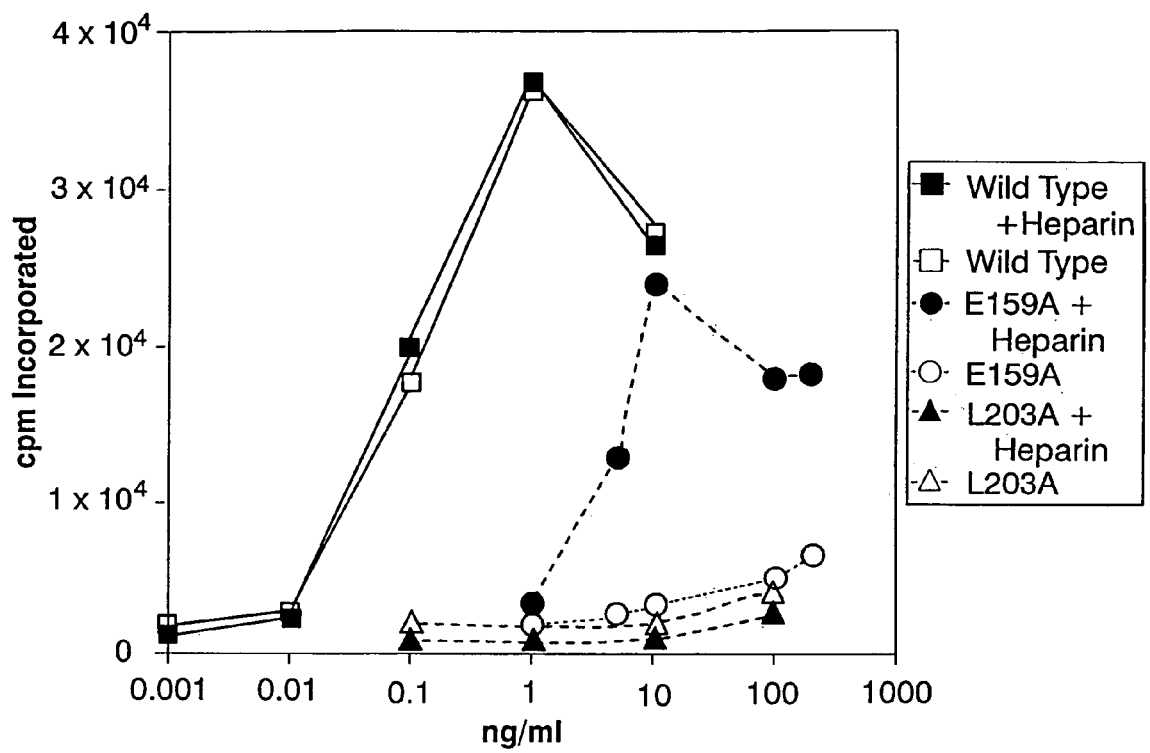
Figure 5B:
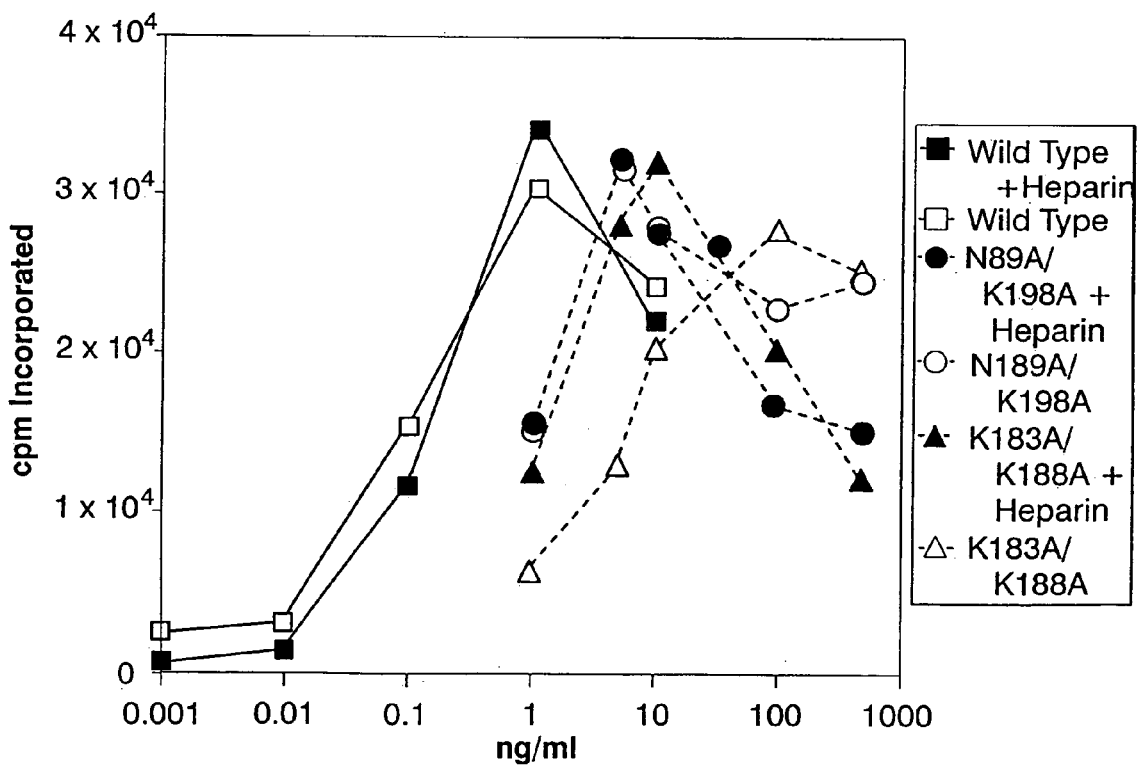

FIGS. 5A-B show plots illustrating the differential effect of heparin on stimulation of DNA synthesis in NIH 3T3 cells by different mutant FGF4 polypeptides that are described in the Examples, infra. FIG. 5A plots data from a representative experiments using the E159A and L203A mutants. FIG. 5B plots data from representative experiments using the K183A/K188A and the N89A/K198A double mutants.

Figure 6:
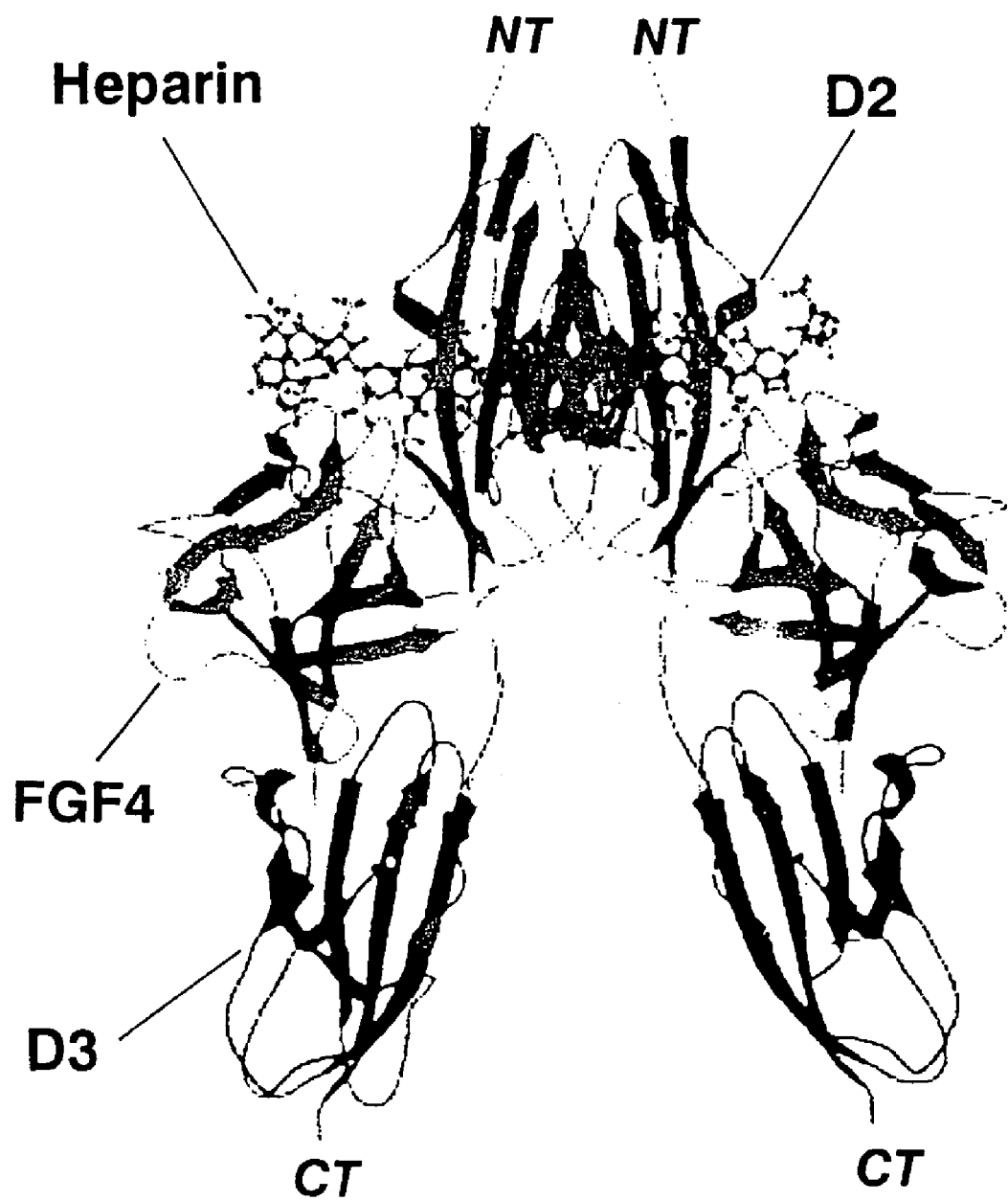

FIG. 6 provides a representative model (generated using the Molscript and Raster3D programs) for a dimeric complex of FGF4-FGFR1-heparin. The model was created by superimposition of the Cα traces for two FGF4 structures onto Cα traces of the two FGF2 molecules in a ternary structure for FGF2-FGFR1-heparin (see, the Examples, infra). NT and CT denote the amino- and carboxy-termini, respectively, of the FGFR1 polypeptide. The FGF4, FGFR1, D2 and D3 domains are labeled. Heparin oligosaccharides are rendered in ball-and-stick.

Figure 7A:
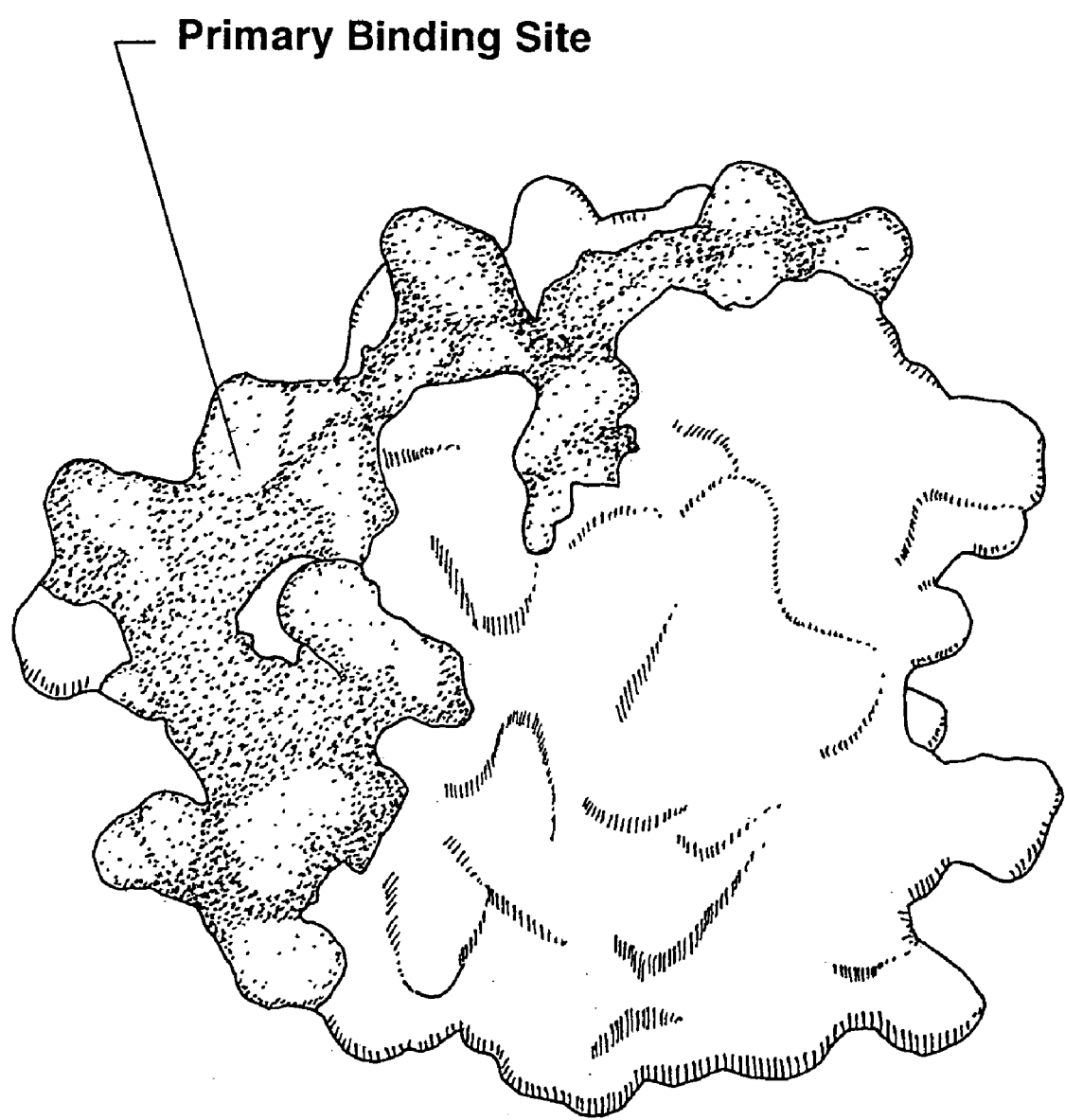

FIG. 7A-B shows the primary binding site, i.e., the surface through which FGF4 binds to FGFR in the context of the FGF4-FGFR-heparin dimer. The shaded region in the three-dimensional model (7A), and in the amino acid sequence (7B) depicts the primary binding sites. The primary binding sites in the amino acid sequences are also shown for FGF6 (SEQ ID NO:21) and FGF1 (SEQ ID NO:22) in 7B.

Figure 8A:
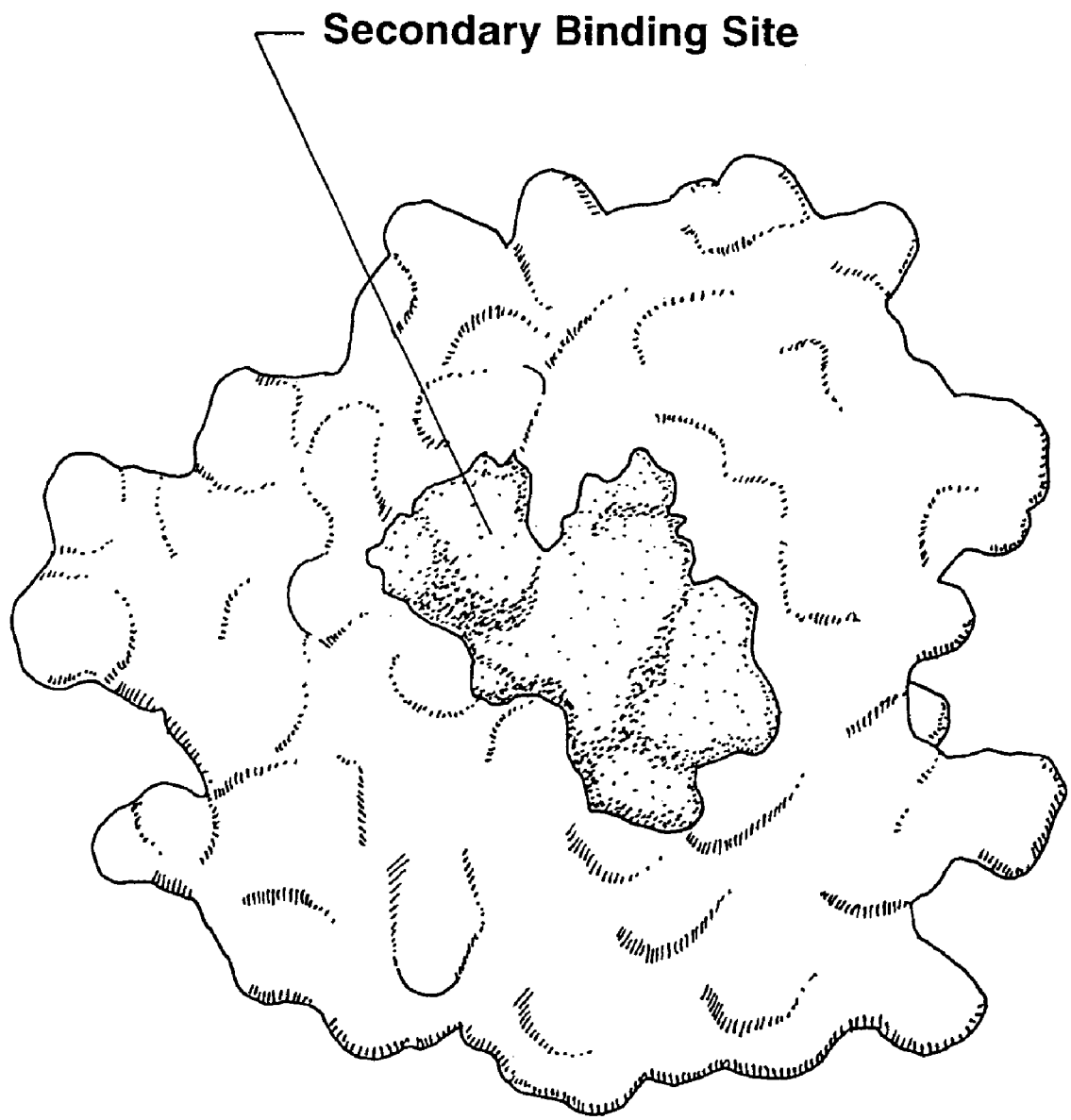

FIG. 8A-B shows the secondary binding site, i.e., the surface which binds to a second FGFR molecule in the context of the FGF4-FGFR-heparin dimer. The secondary binding site is depicted as shaded in both the three-dimensional model (8A), and the amino acid sequence (8B). The secondary binding sites in the amino acid sequences are also shown for FGF6 (SEQ ID NO:21) and FGF1 (SEQ ID NO:22) in 8B.

Figure 9A:
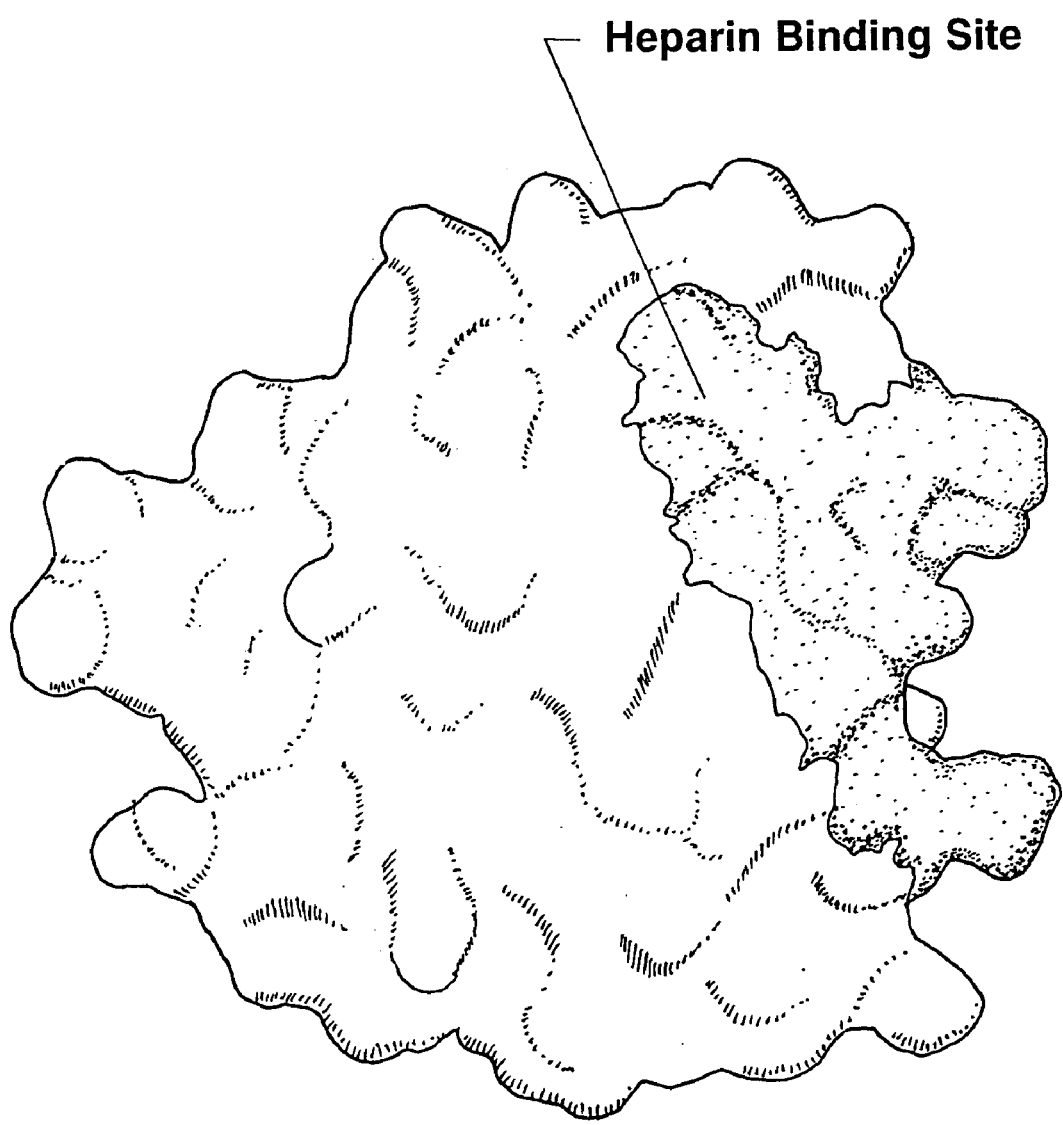

FIG. 9A-B shows the heparin binding site, i.e., the surface which binds to heparin in the context of the FGF4-FGFR-heparin dimer. The primary binding site is depicted as shaded in both the three-dimensional model (9A), and the amino acid sequence (9B). The heparmn binding sites in the amino acid sequences are also shown for FGF6 (SEQ ID NO:21) and FGF1 (SEQ ID NO:22) in 9B.

5. DETAILED DESCRIPTION OF THE INVENTION

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

5.1 General Definitions

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifrigation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

A "sample" as used herein refers to a biological material which can be tested, e.g., for the presence of an FGF polypeptide or FGF nucleic acid or, alternatively, for the presence of an FGFR polypeptide or nucleic acid (e.g., to identify cells that specifically express either FGF or FGFR). Such samples can be obtained from any source, including tissue, blood and blood cells, and cell culture.

Non-human animals include, without limitation, laboratory animals such as mice, rats, rabbits, hamsters, guinea pigs, etc.; domestic animals such as dogs and cats; and farm animals such as sheep, goats, pigs, horses, and cows.

In preferred embodiments, the terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "molecule" means any distinct or distinguishable structural unit of matter comprising one or more atoms, and includes, for example, polypeptides and polynucleotides.

The term "therapeutically effective dose" refers to that amount of a compound or compositions that is sufficient to result in a desired activity.

The phrase "pharmaceutically acceptable" refers to molecular entities and compositions that are physiologically tolerable and do not typically produce an allergic or similar adverse reaction (for example, gastric upset, dizziness and the like) when administered to an individual. Preferably, and particularly where a vaccine is used in humans, the term "pharmaceutically acceptable" may mean approved by a regulatory agency (for example, the U.S. Food and Drug Administration) or listed in a generally recognized pharmacopeia for use in animals (for example, the U.S. Pharmacopeia).

The term "carrier" refers to a diluent, adjuvant, excipient, or vehicle with which a compound is administered. Sterile water or aqueous saline solutions and aqueous dextrose and glycerol solutions are preferably employed as carriers, particularly for injectable solutions. Exemplary suitable pharmaceutical carriers are described in "Remington's Pharmaceutical Sciences" by E. W. Martin.

5.2 Molecular Biology Definitions

In accordance with the present invention, there may be employed conventional molecular biology, microbiology and recombinant DNA techniques within the skill of the art. Such techniques are explained fully in the literature. See, for example, Sambrook, Fitsch & Maniatis, *Molecular Cloning: A Laboratory Manual*, Second Edition (1989) Cold Spring Harbor Laboratory Press, Cold Spring Harbor, N.Y. (referred to herein as "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins, eds. 1984); *Animal Cell Culture* (R. I. Freshney, ed. 1986); *Immobilized Cells and Enzymes* (IRL Press, 1986); B. E. Perbal, *A Practical Guide to Molecular Cloning* (1984); F. M. Ausubel et al. (eds.), *Current Protocols in Molecular Biology*, John Wiley & Sons, Inc. (1994).

The term "polymer" means any substance or compound that is composed of two or more building blocks ('mers') that are repetitively linked together. For example, a "dimer" is a compound in which two building blocks have been joined togther; a "trimer" is a compound in which three building blocks have been joined together; etc.

The term "polynucleotide" or "nucleic acid molecule" as used herein refers to a polymeric molecule having a backbone that supports bases capable of hydrogen bonding to typical polynucleotides, wherein the polymer backbone presents the bases in a manner to permit such hydrogen bonding in a specific fashion between the polymeric molecule and a typical polynucleotide (e.g., single-stranded DNA). Such bases are typically inosine, adenosine, guanosine, cytosine, uracil and thymidine. Polymeric molecules include "double stranded" and "single stranded" DNA and RNA, as well as backbone modifications thereof (for example, methylphosphonate linkages).

Thus, a "polynucleotide" or "nucleic acid" sequence is a series of nucleotide bases (also called "nucleotides"), generally in DNA and RNA, and means any chain of two or more nucleotides. A nucleotide sequence frequently carries genetic information, including the information used by cellular machinery to make proteins and enzymes. The terms include genomic DNA, cDNA, RNA, any synthetic and genetically manipulated polynucleotide, and both sense and antisense polynucleotides. This includes single- and double-stranded molecules; i.e., DNA-DNA, DNA-RNA, and RNA-RNA hybrids as well as "protein nucleic acids" (PNA) formed by conjugating bases to an amino acid backbone. This also includes nucleic acids containing modified bases, for example, thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.) and alkylators to name a few. The polynucleotides may be derivatized by formation of a methyl or ethyl phosphotriester or an alkyl phosphoramidite linkage. Furthermore, the polynucleotides herein may also be modified with a label capable of providing a detectable signal, either directly or indirectly. Exemplary labels include radioisotopes, fluorescent molecules, biotin and the like. Other non-limiting examples of modification which may be made are provided, below, in the description of the present invention.

A "polypeptide" is a chain of chemical building blocks called amino acids that are linked together by chemical bonds called "peptide bonds". The term "protein" refers to polypeptides that contain the amino acid residues encoded by a gene or by a nucleic acid molecule (e.g., an mRNA or a cDNA) transcribed from that gene either directly or indirectly. Optionally, a protein may lack certain amino acid residues that are encoded by a gene or by an mRNA. For example, a gene or mRNA molecule may encode a sequence of amino acid residues on the N-terminus of a protein (i.e., a signal sequence) that is cleaved from, and therefore may not be part of, the final protein. A protein or polypeptide, including an enzyme, may be a "native" or "wild-type", meaning that it occurs in nature; or it may be a "mutant", "variant" or "modified", meaning that it has been made, altered, derived, or is in some way different or changed from a native protein or from another mutant. See Appendix A for the three letter and one letter abbreviations for 20 amino acids.

A "ligand" is, broadly speaking, any molecule that binds to another molecule. In preferred embodiments, the ligand is either a soluble molecule or the smaller of the two molecules or both. The other molecule is referred to as a "receptor". In preferred embodiments, both a ligand and its receptor are molecules (preferably proteins or polypeptides) produced by cells. Preferably, a ligand is a soluble molecule and the receptor is an integral membrane protein (i.e., a protein expressed on the surface of a cell). In a particularly preferred embodiment of the invention the ligand is a fibroblast growth factor (FGF) and the receptor is a fibroblast growth factor receptor (FGFR).

The binding of a ligand to its receptor is frequently a step of signal transduction with a cell. For example, in preferred embodiments where a ligand is an FGF polypeptide and a receptor is an FGFR polypeptide, the binding of FGF to the FGFR polypeptide may lead to activation of a tyrosine kinase activity within the FGFR polypeptide. Activation of the tyrosine kinase activity may, in turn, initiate other activities associated with FGF signaling, including but not limited to mitogenesis and angiogenesis. Other exemplary ligand-receptor interactions include, but are not limited to, binding of a hormone to a hormone receptor (for example, the binding of estrogen to the estrogen receptor) and the binding of a neurotransmitter to a receptor on the surface of a neuron.

"Amplification" of a polynucleotide, as used herein, denotes the use of polymerase chain reaction (PCR) to increase the concentration of a particular DNA sequence within a mixture of DNA sequences. For a description of PCR see Saiki et al., *Science* 1988, 239:487.

"Chemical sequencing" of DNA denotes methods such as that of Maxam and Gilbert (Maxam-Gilbert sequencing; see Maxam & Gilbert, *Proc. Natl. Acad. Sci. U.S.A.* 1977, 74:560), in which DNA is cleaved using individual base-specific reactions.

"Enzymatic sequencing" of DNA denotes methods such as that of Sanger (Sanger et al., *Proc. Natl. Acad. Sci. U.S.A.* 1977, 74:5463) and variations thereof well known in the art, in a single-stranded DNA is copied and randomly terminated using DNA polymerase.

A "gene" is a sequence of nucleotides which code for a functional "gene product". Generally, a gene product is a functional protein. However, a gene product can also be another type of molecule in a cell, such as an RNA (e.g., a tRNA or a rRNA). For the purposes of the present invention, a gene product also refers to an mRNA sequence which may be found in a cell. For example, measuring gene expression levels according to the invention may correspond to measuring mRNA levels. A gene may also comprise regulatory (i.e., non-coding) sequences as well as coding sequences. Exemplary regulatory sequences include promoter sequences, which determine, for example, the conditions under which the gene is expressed. The transcribed region of the gene may also include untranslated regions including introns, a 5'-untranslated region (5'-UTR) and a 3'-untranslated region (3'-UTR).

A "coding sequence" or a sequence "encoding" an expression product, such as an RNA, polypeptide, protein or enzyme, is a nucleotide sequence that, when expressed, results in the production of that RNA, polypeptide, protein or enzyme; i.e., the nucleotide sequence "encodes" that RNA or it encodes the amino acid sequence for that polypeptide, protein or enzyme.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently found, for example, by mapping with nuclease S1), as well as protein binding domains (consensus sequences) responsible for the binding of RNA polymerase.

A coding sequence is "under the control of" or is "operatively associated with" transcriptional and translational control sequences in a cell when RNA polymerase transcribes the coding sequence into RNA, which is then trans-RNA spliced (if it contains introns) and, if the sequence encodes a protein, is translated into that protein.

The term "express" and "expression" means allowing or causing the information in a gene or DNA sequence to become manifest, for example producing RNA (such as rRNA or mRNA) or a protein by activating the cellular functions involved in transcription and translation of a corresponding gene or DNA sequence. A DNA sequence is expressed by a cell to form an "expression product" such as an RNA (e.g., a mRNA or a rRNA) or a protein. The expression product itself, e.g., the resulting RNA or protein, may also be said to be "expressed" by the cell.

The term "transfection" means the introduction of a foreign nucleic acid into a eukaryotic cell. The term "transformation" means the introduction of a "foreign" (i.e., extrinsic or extracellular) gene, DNA or RNA sequence into a prokaryotic host cell so that the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell or cells of a different genus or species.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence. Vectors may include plasmids, phages, viruses, etc. and are discussed in greater detail below.

A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A large number of vectors, including plasmid and fungal vectors, have been described for replication and/or expression in a variety of eukaryotic and prokaryotic hosts. The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal).

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells such as Sf9, Hi5 or S2 cells and *Baculovirus* vectors, *Drosophila* cells (Schneider cells) and expression systems, and mammalian host cells and vectors.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, a gene encoding a protein of interest, e.g., an FGF4 gene, is heterologous to the vector DNA in which it is inserted for cloning or expression, and it is heterologous to a host cell containing such a vector, in which it is expressed, e.g., a CHO cell. with a different gene that the one it is operatively associated with in nature.

The terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence. The term "variant" may also be used to indicate a modified or altered gene, DNA sequence, RNA, enzyme, cell, etc.; i.e., any kind of mutant. For example, the present invention relates to altered or "chimeric" RNA molecules that comprise an rRNA sequence that is altered by inserting a heterologous RNA sequence that is not naturally part of that sequence or is not naturally located at the position of that rRNA sequence. Such chimeric RNA sequences, as well as DNA and genes that encode them, are also referred to herein as "mutant" sequences.

"Sequence-conservative variants" of a polynucleotide sequence are those in which a change of one or more nucleotides in a given codon position results in no alteration in the amino acid encoded at that position.

"Function-conservative variants" of a polypeptide or polynucleotide are those in which a given amino acid residue in the polypeptide, or the amino acid residue encoded by a codon of the polynucleotide, has been changed or altered without altering the overall conformation and function of the polypeptide. For example, function-conservative variants may include, but are not limited to, replacement of an amino acid with one having similar properties (for example, polarity, hydrogen bonding potential, acidic, basic, hydrophobic, aromatic and the like). Amino acid residues with similar properties are well known in the art. For example, the amino acid residues arginine, histidine and lysine are hydrophilic, basic amino acid residues and may therefore be interchangeable. Similar, the amino acid residue isoleucine, which is a hydrophobic amino acid residue, may be replaced with leucine, methionine or valine. Such changes are expected to have little or no effect on the apparent molecular weight or isoelectric point of the polypeptide. Amino acid residues other than those indicated as conserved may also differ in a protein or enzyme so that the percent protein or amino acid sequence similarity (e.g., percent identity or homology) between any two proteins of similar function may vary and may be, for example, from 70% to 99% as determined according to an alignment scheme such as the Cluster Method, wherein similarity is based on the MEGALIGN algorithm. "Function-conservative variants" of a given polypeptide also include polypeptides that have at least 60% amino acid sequence identity to the given polypeptide as determined, e.g., by the BLAST or FASTA algorithms. Preferably, function-conservative variants of a given polypeptide have at least 75%, more preferably at least 85% and still more preferably at least 90% amino acid sequence identity to the given polypeptide and, preferably, also have the same or substantially similar properties (e.g., of molecular weight and/or isoelectric point) or functions (e.g., biological functions or activities) as the native or parent polypeptide to which it is compared.

Thus, for example, in particular embodiments wherein the polypeptides are FGFR polypeptides, function-conservative variants may not only have between at least 75% and at least 90% amino acid sequence identity to a given FGFR, but preferably also have similar properties, such as conserved domains (e.g., as in a D1, D2 or D3 domain, described supra) and/or similar biological function or activities, such as a tyrosine kinase activity and/or the ability to stimulate activities associated with FGF signaling (e.g., mitogenesis or angiogenesis).

Similarly, in embodiments wherein a polypeptide is an FGF ligand, function-conservative variants may not only have between at least 75% and at least 90% amino acid sequence identity to a given FGF, but preferably also have similar properties. For example, a function-conservative variant of an FGF ligand preferably binds to the same FGF receptor as the FGF ligand. (preferably, but not necessarily with the same or a similar affinity; e.g., preferably with at least 50% of the binding affinity, more preferably with at least 70% of the binding affinity, and still more preferably with at least 80% or at least 90% of the binding affinity). Preferably, by binding to the FGFR polypeptide, a function-conservative variant will also stimulate a same biological function or activity that is associated with binding of the FGF ligand to the receptor, including any of the functions or activities described, supra, for an FGF receptor.

The term "homologous", in all its grammatical forms and spelling variations, refers to the relationship between two proteins that possess a "common evolutionary origin", including proteins from superfamilies (e.g., the immunoglobulin superfamily) in the same species of organism, as well as homologous proteins from different species of organism (for example, myosin light chain polypeptide, etc.; see, Reeck et al., Cell 1987, 50:667). Homologous proteins of the invention therefore include various FGF proteins and polypeptides derived from the same species of organism (i.e., the FGF family of polypeptides, including FGF1-FGF22), and also FGF proteins and polypeptides derived from different species of organisms. Similarly, homologous proteins of the invention also include various FGFR proteins and polypeptides derived from the same species (i.e., the FGFR family, including FGFR1-4) or from different species of organisms.

Such proteins (and their encoding nucleic acids) have sequence homology, as reflected by their sequence similarity, whether in terms of percent identity or by the presence of specific residues or motifs and conserved positions. For instance, referring agin to particular embodiments where homologous polypeptides are FGF and/or FGFR polypeptides, homologous polypeptides in either the same or in closely related species of organisms (for example, between mammals such as mice and humans) typically share greater than 50% sequence identity, more preferably share at least about 60 to 65% sequence identity, and still more preferably share at least about 75% to 80% sequence identity. Homologous polypeptides between closely related species of organisms may also be cross reactive in both species of organisms. For example, an FGF from one species of organism may bind to and/or activate an FGF receptor polypeptide from a different species of organism and, moreover, an FGF receptor from a first species of organism may stimulate a activity associated with FGF signalling (e.g., mitogenesis or angiogenesis) in a cell from a different species of organism (for example, when the heterologous FGFR polypeptide is recombinantly expressed in that cell).

The term "sequence similarity", in all its grammatical forms, refers to the degree of identity or correspondence between nucleic acid or amino acid sequences that may or may not share a common evolutionary origin (see, Reeck et al., *Cell* 1987, 50:667). However, in common usage and in the instant application, the term "homologous", particularly when modified with an adverb such as "highly", may refer to sequence similarity and may or may not relate to a common evolutionary origin.

In specific embodiments, two nucleic acid sequences are "substantially homologous" or "substantially similar" when at least about 80%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 80% of the amino acid residues are identical, or when greater than about 90% of the amino acid residues are similar (i.e., are functionally identical). Preferably the similar or homologous polypeptide sequences are identified by alignment using, for example, the GCG (Genetics Computer Group, Program Manual for the GCG Package, Version 7, Madison Wis.) pileup program, or using any of the programs and algorithms described above (e.g., BLAST, FASTA, CLUSTAL, etc.).

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin or a fluorescent dye (for example, Cy3 or Cy5) has been covalently conjugated. In one embodiment, a labeled oligonucleotide can be used as a probe to detect the presence of a nucleic acid. In another embodiment, oligonucleotides (one or both of which may be labeled) can be used as PCR primers; e.g. for cloning full length or a fragment of either an FGF or an FGFR nucleic acid, or to detect the presence of nucleic acids encoding either an FGF or an FGFR polypeptide. In a further embodiment, an oligonucleotide of the invention can form a triple helix with a an FGF or an FGFR DNA or RNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

5.3 X-ray Crystallography Definitions

The present invention also uses techniques of conventional X-ray crystallography. These techniques are well known and are within the routine skill of the art. Such techniques are described more fully in the literature. See, for example, Cantor & Schimmel, *Biophysical Chemistry* 1980 (Vols. I-III) W. H. Freeman and Company (particularly Chapters 1-13 in Vol. I, and Chapter 13 in Vol. II).

The term "crystal" refers, generally, to any ordered (or at least partially ordered) three-dimensional array of molecules. Preferably, the ordering of molecules within a crystal is at least sufficient to produce a sharp X-ray diffraction pattern so that the molecules' three-dimensional structure may be determined.

The molecules in a crystal may be of any type, and it will be understood that a crystal may contain molecules of only one type or may comprise a plurality of different types of molecules. In preferred embodiments, crystals of the present invention comprise at least one biomolecule, such as a protein, or a fragment thereof. Crystals of the invention may even comprise a complex or assembly of two or more proteins or other biomolecules. For example, a crystal may comprise two different proteins, such as a receptor and a ligand, or a crystal may comprise two more molecules of the same protein bound together, e.g., to form a dimer or other multimer complex. Typically, crystals that contain biological molecules such as proteins will contain other molecules as well, such molecules of solvent (e.g., water molecules) and/or salt. Other molecules such as drugs, drug candidates or compounds that bind to the protein may also be present in a crystal.

It will be understood by a skilled artisan that crystals of the invention comprises a "unit cell", or basic parallelepiped shaped block defined by vectors denoted a, b and c. The entire volume of a crystal may be constructed by the regular assembly of such blocks or "lattices". A crystal is also defined by the overall symmetry of elements (i.e., molecules) within the cell, which is referred to as the "space group." Thus, a crystal's space group is defined by symmetry relations within the molecules making up the unit cell. The "asymmetric unit" is the smallest possible unit from which the crystal structure may be generated by making use of the symmetric relations defining the space group.

The term "structure coordinates" or "structure" refers to mathematical coordinates that define the position of atoms in a molecule or in an assembly of molecules in three-dimensional space (for example, within the asymmetric unit of a crystal). Structure coordinates may be computed or otherwise determined using any information related to the three dimensional arrangement of atoms in a molecule. However, in preferred embodiments of the invention a structure is derived from equations that are related to patterns obtained on diffraction of a monochromatic beam of X-rays by the atoms (which, in such embodiments, may also be referred to as "scattering centers") in a crystal. Typically, such diffraction data is used to calculate an "electron density" map of the crystal's asymmetric unit, and these maps are used, in turn, to establish positions of the individual atoms.

"Heavy atom derivatization" refers to a method of producing chemically modified forms of a crystal (typically a crystal of a protein or other biopolymer), in which the crystal may be soaked in a solution containing heavy metal atom salts or organometallic compounds that can diffuse through the crystal and bind to the surface of the protein or biopolymer. The location(s) of one or more heavy meatl atoms in the crystal may then be determined by X-ray diffraction analysis of the soaked crystal, and this information may be used to facilitate construction of the three-dimension structure of the protein or other molecules contained in the crystal.

"Molecular replacement" refers to a method wherein a preliminary structure coordinates are generated for molecules in a crystal whose structure coordinates are not known. Generally, molecular replacement involves orienting and/or positioning another, preferably similar molecule (such as a homologous protein) whose structure coordinates are known. Phases for an X-ray diffraction pattern may then be determined for the preliminary structure, and these phases can then be combined with actual X-ray diffraction intensities that are observed for the crystal whose structure coordinates are not known, to determine its structure.

5.4 Detailed Description of Invention

The present invention relates to a particular FGF ligand, known in the art as FGF4 and described in the Examples, infra. Such FGF polypeptides generally comprise the amino acid sequence set forth in FIG. 2, or a similar (i.e., homologous or highly-homologous) amino acid sequence. In other preferred embodiments, the methods and compositions of the invention relate to certain variants of the FGF4 polypeptide, hereinafter alternatively referred to as FGF4 mutants or mutant polypeptides. Preferred variants of the FGF4 polypeptide are ones having altered binding affinities either for heparin, for an FGF receptor (e.g., FGFR1) or for both FGFR and heparin. For instance, the Examples, infra, describe several specific variants of FGF4 having one or more amino acid residue substitutions, insertions or deletions that alter the polypeptides' binding affinities for heparin and/or for an FGFR (in particular, for FGFR1). These variant FGF4 polypeptides are therefore considered part of the present invention.

The Examples also provide a description of model three-dimensional structures that describe the binding of FGF4 to an FGF receptor and to heparin. Using these models, a skilled artisan may readily identify amino acid residues of either FGF or FGFR that may be modified to produce molecules with greater or lower binding affinities that wild-type FGF4 and FGFR. These molecules are useful agonist and antagonist for FGF ligand-receptor binding and/or for bioactivities associated therewith. Accordingly, the compositions and methods of the invention include screening methods that identify such molecules, preferably using the models of the present invention and/or by modifying key amino acid residues identified in the Examples, below.

The present invention identifies three regions or domains, hereinafter referred to as (1) the primary binding site, which is the surface through which one FGF4 molecule binds to one FGFR molecule and forms a complex, (2) the secondary binding site, which is the surface which binds to a second FGFR molecule in the context of an FGF4: FGFR-heparin dimer and (3) the heparin binding site, which binds heparin. The primary binding site for the FGF4 polypeptide involves amino acid residue numbers (from FIG. 2) 80-82, 84, 87, 92, 95, 108, 117, 119-124, 126, 129, 136, 151, 159, 161, 165-167 and 203-205. The heparin binding site involves amino acid residue numbers 89, 90, 182-184, 186, 189, 192 and 197-199. The secondary binding site involves amino acid residue numbers 162, 163, 195, 196 and 201. These regions are shown in FIG. 6. Mutation in at least one of the amino acids in these regions may lead to the production of either antagonists or agonists. Such polypeptides can be tested for their ability to stimulate DNA synthesis, in the presence or in the absence of heparin, and/or for their ability to bind to receptors on CHO cells, as described below. Non-limiting examples of mutant FGF4 polypeptides produced pursuant to the present invention are shown in Table 2.

The identification of the three major domains or binding sites of FGF4 that are important for receptor binding and receptor activation could lead to the rational design of mutated FGF4 forms with altered biological activity or function. Such mutant forms of FGF4 could possess 1) higher receptor binding affinity and therefore higher biological potency, 2) the ability to bind to the receptor without inducing receptor dimerization, therefore acting as FGF receptor antagonists, or 3) the ability to interact with different forms of heparin or heparin sulfate proteoglycans, therefore possibly modifying its spectrum of action in a biological context.

This could be accomplished by mutating selected amino acids in the primary binding site, and the secondary binding site, respectively to amino acids which would make stronger bonds with the corresponding receptor region and thus create new FGF4s with higher biological activity. An example of such mutations culd be changing F129 to Y or I, R205 to M or L in the primary binding site domain A, or H201 to L in the secondary binding site. On the other hand, by mutating amino acids in the secondary binding site (the dimerization domain) to Alanine or other amino acids it should be possible to create mutants FGF4 poly-peptides which bind the receptor as a monomer, but are incapable of promoting receptor dimerization, and thus behave as FGF4 receptor antagonists. Furthermore, mutations of the amino acids making up the heparin binding domain would result in lower or higher heparin binding activity. Mutations in this domain could be combined with mutations in the primary binding site to produce a more active FGF4, or they could be combined with mutations in the secondary binding site to produce a better antagonist, since it is known that heparin (that binds to both receptor and FGF ligand) contributes to the formation of stable, active FGF4/FGFR dimers.

Alternatively, one could search databases of chemical or peptide libraries well known to those of ordinary skill in the art, to identify small molecules (peptides) which could bind to the primary or secondary binding sites of FGF4, and thus would inhibit binding of the FGF4 ligand to its receptors.

A further application of the findings presented herein is the screening of the above mentioned databases for molecules which mimic the structure of the primary or secondary binding sites of FGF4. Such molecules would be expected to bind to FGF4 receptors, but would be unable to activate signaling through the receptor. They would however compete with the binding of FGF4 to its receptor, or with its ability to induce receptor dimerization, and thus would act as FGFR antagonists.

FGF4 mutant polypeptides for use in the present invention can be produced as described below, e.g., by site-directed mutagenesis of the nucleic acid encoding FGF4. subdloned in an expression vector and purified as described below. Antagonists can be used to treat patients suffering from FGF4-mediated illnesses such as bladder cancer. Agonists can be employed when using FGF4 for its angiogenic or wound healing properties. The nucleic acid encoding FGF4 can be obtained as described in U.S. Pat. Nos. 5,750,659 and 5,459,250. Either full length FGF4 or truncated FGF4 may be used.

6. EXAMPLES

The present invention is also described by means of particular examples. However, the use of such examples anywhere in the specification is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the fill scope of equivalents to which the claims are entitled.

To explore the structural determinants of FGF4 involved in receptor and heparin binding, the crystal structure of FGF4 was determined, as described here, at 1.8 Å resolution. As expected, FGF4 adopts a β-trefoil fold similar to other FGFs. Superimposition of FGF4 structure onto FGF2 bound to FGFR1 and heparin allows the identification of receptor and heparin binding sites in FGF4. Mutation of several key FGF4 residues, observed to interact with FGFR1 in the model described here, produces variant FGF4 ligands that have reduced receptor binding affinities and extremely low mitogenic potential. Significantly, the observed interactions between FGF4 and FGFR1 D3 provide a potential basis for preferential affinity of FGF4 towards IIIc splice variants of FGFR1-3. Moreover, the presented modeling studies along with mutational data suggest a two step model for FGF-FGFR binding that involves initial formation of a crucial FGF-D2 interface stabilized by heparin binding followed by secondary FGF-D3 interactions.

6.1 Materials and Methods

Protein expression and purification of FGF4. DNA fragments generated by polymerase chain reaction (PCR) of human FGF4 cDNA (encoding residues Gly79 to Leu206) were subcloned into the pET-15b bacterial expression vector using NcoI and XhoI cloning sites. The resulting construct (FGF4-pET15b) was transformed into the BL21 (DE3) bacteria and FGF4 expression was induced with 1 mM Isopropyl-1-thio-β-D-galactopyranoside for 5 hours. The bacteria were then centrifuged and subsequently lysed in a 25 mM Na/K phosphate buffer (pH 7.5) containing 300 mM NaCl using a French Cell Press. The N-terminal truncated FGF4 (Gly$^{79}$-Leu$^{206}$) was found primarily in the insoluble fraction and was extracted in 25 mM Na/K phosphate buffer (pH 7.5) containing 1 M NaCl at 4° C. overnight. Following centrifugation, soluble FGF4 was diluted 5 times with 25 mM Na/K phosphate buffer (pH 7.5) and loaded onto a Source S column (Pharmacia). Bound FGF4 was eluted by a linear gradient of NaCl to 1 M in a 25 mM Na/K phosphate buffer (pH 7.5). Matrix-assisted laser desorption ionization mass spectrometry of the purified FGF4 gave a molecular mass of 14,244 daltons (Da) (calculated mass 14,409 Da). The mass difference was due to the cleavage of the initiation methionine and a point mutation (Ser182Gly) resulting from PCR. This mutation had no effect on FGF4 biological activity.

Crystallization and data collection. Crystals of FGF4 were grown by vapor diffusion at 20° C. using the hanging drop method. Briefly, 2 µl of protein solution (2 mg/ml in 25 mM HEPES-NaOH buffer (pH 7.5) containing 150 mM NaCl) were mixed with an equal volume of the crystallization buffer (30% Polyethylene glycol 8000, 0.2 M ammonium sulfate). FGF4 crystals thus obtained belong to the orthorhombic space group $P2_12_12_1$ with unit cell dimensions a=40.37 Å, b=53.3 Å, and c=56.23 Å. There is one molecule of FGF4 in the asymmetric unit with a solvent content of approximately 43%. Diffraction data were collected from a flash-frozen (in a dry nitrogen stream using mother liquor containing 10% glycerol as cryo-protectant) crystal on an R-Axis IV image plate detector at Beamline X4-A at the National Synchrotron Light Source, Brookhaven National Laboratory. Data were processed using DENZO and SCALEPACK (see, Otwinowski & Minor, *Methods Enzymol.* 1997, 276:307-326).

Structure determination and refinement. A molecular replacement solution was found for one copy of FGF4 in the asymmetric unit using the program AmoRe (Navaza, *Acta Crystallogr. Sect. A* 1994, 50:157-163) and the structure of FGF2 (Protein Data Bank entry 2FGF; see also, Zhang et al., *Proc. Natl. Acad. Sci. U.S.A.* 1991, 88:3446-3450) as the search model. Simulated annealing and positional/B-factor refinement were performed using CNS (Bruenger et al, *Acta Crystallogr. Sect. D* 1998, 54:905-921). Bulk solvent and anisotropic B-factor corrections were applied. Model building into $2F_o-F_c$ and $F_o-F_c$ electron density maps was performed with the program O (Jones et al., *Acta Crystallogr. Sect. A* 1991, 47:110-119). The atomic model contains residues 79 to 206 of FGF4, 3 sulfate ions, and 96 water molecules. The average B-factor is 10.5 Å$^2$ for the FGF4 molecule, 40.5 Å$^2$ for the sulfate ions, and 17.5 Å$^2$ for the water molecules.

Production of mutant FGF4 proteins. Alanine substitutions were introduced into the N-terminal truncated FGF4 (Gly$^{79}$-Leu$^{206}$) by PCR site-directed mutagenesis (Quik Change™, Stratagene) with the FGF4-pET15b expression plasmid (see above for description) as the template and the following mutant oligos as primers:

```
Y87A:      5'-AAGCGGCTGCGGCGGCTCGCATGCAACGTGGGCATCGGC-3'

F129A:     5'-GCGTGGTGAGCATCGCCGGCGTGGCCAGCCGG-3'

F151A:     5'-CTATGGCTCGCCCTTCGCGACCGATGAGTGCACGTTC-3'

E159A:     5'-GATGAGTGCACGTTCAAGGCCATTCTCCTTCCCAAC-3'

Y166A:     5'-CTCCTTCCCAACAACGCGAACGCGTACGAGTCC-3'

L203:      5'-CCATGAAGGTCACCCACTTCGCCCCTAGGCTGTGACCC-3'

R205A:     5'-CCCACTTCCTCCCCGCGCTGTGACCTTCCAGAGG-3'

N89A:      5'-CGGCGGCTCTACTGCGCCGTGGGCATCGGCTTC-3'

K198A:     5'-GTGTCGCCCACCATGGCGGTCACCCACTTCCTC-3'

K183A/K1   5'-GCCCTGAGCGCGAATGGGAAGACCGCGAAGGGGAAC-3'
```

```
88A:

R103A:    5'-GCGCTCCCCGACGGCGCCATCGGCGGCGCGCAC-3'

K144A:    5'-ATGAGCAGCAAGGGCGCGCTCTATGGCTCGCCC-3'

N89A/K19  Alanine substitution were introduced into the N-
8A/K1893  terminally trunacted FGF4 N89A/K198A mutant as a
A/K188A:  template by PCR site-directed mutagenesis with
          sense and antisense oligonucleotides containing
          K183A/K188A mutations:
          5'-GCCCTGAGCGCGAATGGGAAGACCGCGAAGGGGAAC-3'

E117A     5'-CGCGACAGCCTGCTGGCGCTCTCGCCCGTGGAG-3'

L162A     5'-TTCAAGGAGATTCTCGCTCCCAACAACTACAA-3'

H201A     5'-ACCATGAAGGTCACCGCCTTCCTCCCAGGCT-3'

P163A     5'-GGAGATTCTCCTTGCCAACAACTACAACGCC-3'

P195A     5'-GGGAACCGAGTGTCGGCCACCATGAAGGTCACC-3'

T196A     5'-GGGAACCGAGTGTCGCCGCCATGAAGGTCACCCACTTCC-3'
```

The presence of the mutations was confirmed by sequencing. Mutant FGF4-pET15b plasmids were transformed into *E. coli* strain BL21 (DE3). Expression of the FGF4 proteins was induced as described above. Following centrifugation, cells expressing wild type and various mutant FGF4 proteins were suspended in a 50 mM HEPES-NaOH buffer (pH 7.4) containing 1 M NaCl and protease inhibitors (100 μg/ml PMSF, and 2 μg/ml Aprotinin) and disrupted by sonication. Lysates were left at 4° C. overnight in order to salt-extract the FGF4 proteins from particulate fractions. Following centrifugation supernatants containing soluble FGF4 proteins were diluted 4 times with 50 mM HEPES-NaOH buffer (pH 7.4), and loaded onto heparin-Sepharose columns. After washing the columns with 50 mM HEPES-NaOH (pH 7.4) buffer containing 250 mM NaCl, the FGF4 proteins were eluted by a 50 mM HEPES buffer (pH 7.4) containing 1.5 M NaCl. Fractions were analyzed by SDS-PAGE (15%) and the purity of the FGF4 proteins was accessed by staining with Coomassie Blue R-250.

DNA synthesis assay. NIH3T3 cells were seeded at a density of $3 \times 10^4$ cells/well in 24-wells plates in Dulbecco's modified Eagle's medium (DMEM) supplemented with 10% calf serum. The following day the medium was replaced with DMEM containing only 0.5% calf serum and the cells were allowed to reach quiescence for 48 hours. Thereafter, serial dilutions of wild-type full length FGF4 ($Ala^{31}$-$Leu^{206}$), N-terminal truncated wild type or mutant FGF4 ($Gly^{79}$-$Leu^{206}$) were added for 18 hours. Cells were then labeled with 1 μCi of $^3$H-thymidine for 6 hours, washed with Tris-HCl buffered saline (pH 7.5), and lysed with 0.5 M NaOH. The lysates were then neutralized with 0.5 HCl and the radioactivity incorporated into the acid-precipitable material was measured using a β-counter (LKB, Pharmacia). Each assay was performed in triplicate.

Receptor bintdinig assay. N-terminal truncated FGF4 ($Gly^{79}$-$Leu^{206}$) was radio-iodinated by the chloramine T method using a previously described protocol (Bellosta et al., *J. Cell Biol.* 1993, 121:705-713). The labeled FGF4 were separated from free iodine over a Sephadex G-25 column, which was previously equiliberated in phosphate buffered saline (PBS) containing 1% bovine serum albumin. CHO cells, over-expressing FGFR2 (Mansukhani et al., *Proc. Natl. Acad. Sci. U.S.A.* 1992, 89:3305-3309), were seeded at $1 \times 10^6$ cells/well in 6 well plates in DMEM containing 10% fetal calf serum. The following day the medium was removed and the cells were allowed to bind labeled FGF4 (specific activity $2.5 \times 10^4$ cpm/ng) in DMEM containing 25 mM HEPES-NaOH (pH 7.4), 15% gelatin, 10 μg/ml heparin, and increasing concentrations of the wild type or mutant FGF4 proteins for 2 hours at 4° C. Cells were then washed several times with ice-cold Tris-HCl buffered saline (pH 7.5) and the receptor-bound radio-labeled FGF4 was released using a 50 mM Sodium Acetate buffer (pH 4.0) containing 2 M NaCl. Radioactivity was measured using a γ-counter (LKB-Pharmacia). Binding assays were done in duplicate.

6.2 Results and Discussion

Structure determination. The mature, secreted form of human FGF4 spans amino acids Ala31 to Leu206 (Bellosta et al., *J. Cell Biol.* 1993, 121:705-713). Based on the crystal structure of FGF2 (Eriksson et al., *Proc. Natl. Acad. Sci. U.S.A.* 1991, 88:3441-3445; Zhang et al., *Proc. Natl. Acad. Sci. U.S.A.* 1991, 88:3446-3450; Zhu et al., *Science* 1991, 251:90-93), the β-trefoil core of FGF4 is expected to start at Leu83 (Pro29 in FGF2). Recent crystal structures of three different FGF-FGFR complexes have revealed that the residues immediately preceeding the β-trefoil core in FGF1 and FGF2 are involved in FGFR binding (Plotnikov et al., *Cell* 1999, 98:641-650; Plotnikov et al., *Cell* 2000, 101:413-424; Springer et al., *J. Biol. Chem.* 1994, 269:26879-26884). These residues correspond to amino acids Gly79 to Arg82 of FGF4 (FIG. 2). Thus, to maximize the likelihood of obtaining diffracting crystals without jeopardizing the biological activity of FGF4, an N-terminal truncated FGF4 polypeptide containing residues Gly79 to Leu206 (Gly$^{79}$-Leu$^{206}$) was crystallized. Truncated FGF4 was expressed in *E. coli* and purified to homogeneity (see, Subsection 6.1, supra). The mitogenic activity of the truncated FGF4 on NIH3T3 cells was only slightly lower than that of the mature FGF4, indicating that the truncated FGF4 contains the majority of receptor binding sites. Crystallization trials with FGF4 produced orthorhombic crystals with one molecule per asymmetric unit. The crystal structure of FGF4 was solved by molecular replacement as described, supra, and refined to 1.8 Å resolution with an R-value of 19.4% (free R-value of 20.7%). The atomic model for FGF4 consists of one FGF4 molecule (residues 79 to 206), 3 sulfate ions and 96 water molecules. The coordinates for the FGF4 crystal structure are given in the accompanying Appendix B, infra, in PDB file format. Data collection and refinement statistics are given below in Table 1.

TABLE 1

Summary of crystallographic analysis

I. Data Collection Statistics:

| Resolution (Å) | Reflections (total/unique) | Completeness (%) | $R_{sym}^a$ (%) | Signal ($<I/\sigma I>$) |
|---|---|---|---|---|
| 25.0-1.8 | 40562/11590 | 99.6 (995)$^b$ | 5.1 (10.9)$^b$ | 16.5 |

II. Refinement Statistics:$^c$

| | | | Root-mean-square Deviations | | |
|---|---|---|---|---|---|
| Resolution (Å) | Reflections | $R_{cryst}/R_{free}^d$ (%) | Bonds (Å) | Angles (°) | B-factors$^e$ (Å$^2$) |
| 25.0-1.8 | 11488 | 19.4/20.7 | 0.005 | 1.31 | 1.00 |

$^a R_{sym} = 100 \times \sum_{hkl}\sum_i |I_i(hkl) - \langle I(hkl)\rangle| / \sum_{hkl}\sum_i I_i(hkl)$.

$^b$Value in parentheses is for the highest resolution shell: 1.86-1.8 Å.
$^c$Atomic model: 994 protein atoms, 3 SO$_4^{2-}$ ions, and 42 water molecules.

$^d R_{cryst/free} = 100 \times \sum_{hkl} ||F_o(hkl)| - |F_c(hkl)|| / \sum_{hkl} |F_o(hkl)|$, where $F_o$ ($>0\sigma$) and $F_c$ are the observed and calculated structure factors. 5% of the reflections were used for calculations of $R^{free}$.
$^e$For bonded protein atoms.

Description of the structure. As expected by sequence similarity (Vainikka et al., *EMBO J.* 1993, 11:4273-4280), FGF4 adopts a β-trefoil fold conformation (FIG. 1). Superimposition of the Cα traces located within the β-trefoil core of FGF4 with those of FGF1 (Zhu et al., *Science* 1991, 251:90-93) and FGF2 (Zhang et al., *Proc. Natl. Acad. Sci. U.S.A.* 1991, 88:3446-3450) gives a root-mean-square (rms) deviation of only 0.86 Å (122 common Cα atoms) and 0.76 Å (123 common Cα atoms), respectively. Within the β-trefoil core, the major differences between the FGF4 structure and the structures of FGF1 and FGF2 are the conformations of the β1-β2, β3-β4 and β9-β10 loops. These loops vary in both length and sequence among the various members of the FGF family (FIG. 2). In FGF4, the β1-β2 loop is one residue longer than the corresponding loops of FGF1 and FGF2 (FIG. 2). In contrast, the β3-β4 loop in FGF4 is shorter by one residue than the corresponding loops in FGF1 and FGF2. Like FGF2, the β9-β10 loop in FGF4 is shorter by two residues than in FGF1 (FIG. 2).

As with the structures of free FGF1 and FGF2 (Zhu et al., *Science* 1991, 251:90-93), a sulfate ion is bound to the predicted high affinity heparin-binding site of FGF4. In addition, two other sulfate ions are coordinated by FGF4 residues, whose corresponding residues in FGF1 and FGF2 have not been observed to bind sulfate ions (see, FIG. 6).

Receptor binding sites and specificity. To identify potential receptor binding sites in FGF4, an FGF4-FGFR1 model was constructed by superimposing the FGF4 structure onto the FGF2 structure bound to the ligand binding portion of FGFR1 consisting of Ig-like domains 2 (D2) and 3 (D3) (FIG. 3). Careful inspection of the FGF4-FGFR1 interface showed that the majority of the interactions between FGF4 and FGFR1 in the FGF4-FGFR1 model could be accommodated with minor adjustments of FGF4 side chain rotamers. Three loop regions, the β1-β2 and β9-β10 loops (within the β-trefoil core) and the N-terminus (outside the β-trefoil core), sterically clash with the receptor. In the present crystal structure these loop regions are involved in crystal lattice contacts, implying that the present conformations of these loops are dictated by the lattice contacts. However, upon FGFR binding these regions are expected to undergo changes in backbone conformation to allow an engagement with FGFR1 to occur.

At the FGF4-D2 interface three highly conserved solvent-exposed FGF4 residues, Tyr87, Tyr166 and Leu203, are predicted to pack against a highly conserved hydrophobic surface consisting of Ala167, Pro169, and Val248 at the bottom of D2 in FGFR1 (data not shown). Significant differences between FGF4 and FGF2 at the FGF-D2 interface are the substitutions of Phe40 and Met151 in FGF2 with His95 and Arg205 in FGF4 (FIG. 2). These substitutions may indicate a weaker hydrophobic FGF4-D2 interface compared to the FGF2-D2 interface. At the FGF4-linker interface, Asn167, also highly conserved among FGFs (FIG. 2), is expected to make hydrogen bonds with the FGFR-invariant arginine (Arg250 in FGFR1) in the D2-D3 linker region.

To provide experimental support for the described interactions between FGF4 and FGFR1 at the FGF4-D2 interface, Tyr87, Tyr166, Leu203 and Arg205 were individually mutated to alanine in the N-terminal truncated FGF4 construct (Gly$^{79}$-Leu$^{206}$). Mutant FGF4 proteins were expressed in *E. coli*, purified to near homogeneity as described, supra, and were assayed for the ability to induce DNA synthesis in NIH 3T3 fibroblasts. As shown in FIG. 4 and in Table 2, below, the Y87A, Y166A and L203A mutant FGF4 proteins were severely compromised in their ability to induce DNA synthesis, while the R205A mutant showed a more modest decrease in the induction of DNA synthesis. Thus, these data confirm the observed interactions between FGF4 and D2 in the FGF4-FGFR1 model, and indeed the corresponding 4 residues in FGF2 had been previously shown to be also important for biological activity (Springer et al., *J. Biol. Chem.* 1994, 269:26879-26884).

TABLE 2

Summary of DNA Synthesis Activity and Receptor Binding Affinity of Mutant FGF4 Polypeptides

| Protein | DNA Synthesis NIH 3T3 cells ($ED_{50}$ mutant/ $ED_{50}$ wild-type)[a] | | DNA synthesis assay 32D-FGFR2 cells ED50mut/ED50wt | | Receptor Binding CHO-FGFR2 cells ($IC_{50}$ mutant/$IC_{50}$ wild-type)[b] |
|---|---|---|---|---|---|
| ($Gly^{79}$-$Leu^{206}$) | −heparin | +heparin | −heparin | +heparin | +heparin |
| wild-type | 1 | 1 | 0 | 1 | 1 |
| Y87A | >500 | 500 | | | >100 |
| F129A | >500 | >500 | | | >100 |
| F151A | 1000 | 4 | 0 | 200 | 2.5 |
| E159A | >1000 | 80 | 0 | >1000 | 5.0 |
| Y166A | 500 | >500 | | | >100 |
| L203A | >500 | >500 | | | >100 |
| R205A | 25 | 2.5 | | | 2.5 |
| N89A/K198A | 10 | 10 | 0 | 65 | ND |
| K183A/K188A | 70 | 13 | 0 | 125 | ND |
| R103A/K144A | 1 | 1 | | | ND |
| N89A/K198A/K 183A/K188A | >1333 | 275 | 0 | >1000 | >1000 |
| E117A | ≈1 | ≈1 | 0 | 7 | 7 |
| L162A | 600 | 158 | 0 | >1000 | >1000 |
| H201A | >666 | 125 | | | >1000 |
| P163A | 10 | 4.6 | | | |
| P195A | 8 | 4.6 | | | |
| T196A | 5.5 | 4 | | | |

[a] $ED_{50}$ (Effective Dose) is the dose of FGF4 necessary to reach 50% of maximum DNA synthesis obtained with the wild type FGF4.
[b] $IC_{50}$ (Inhibitory Concentration) is the concentration of FGF4 required to compete 50% of binding of labeled wild type FGF4 to FGFR2.
[c] ND (Not Determined).
[d] 32D is a murine hematopoietic cell line, which does not express FGF receptors or heparin sulfate proteoglycans. As a consequence, even when transfected to express FGF receptors (as in the example, 32D-FGFR2), they require exogenous heparin to be stimulated to proliferate by FGF (Mansukhani et al, PNAS 89: 3305, 1992). In the absence of heparin, FGFs are not mitogenic in these cells (expressed as 0 activity).

Interactions between FGF4 and D3 occur at the upper part of D3 and involve mainly the βB'-βC, βC'-βE and βF-βG loops in D3. At the interface between FGF4 and the βB'-βC loop of D3, Glu159 of FGF4 (an FGF-invariant residue) (FIG. 2) is expected to make a hydrogen bond with Gln284 (an FGFR-invariant residue). This prediction is supported by a 1,000-fold reduction in the ability of the E159A mutant FGF4 to induce DNA synthesis in living cells (FIG. 5A and Table 2, above).

In contrast to the interface between FGF4 and the βB'-βC loop, interactions between FGF4 and the βC'-βE and βF-βG loops are variable. Significantly, FGF4, like FGF1, has a serine (Ser119) at the position homologous to Gln65 of FGF2 (FIG. 2). It has previously been shown that Gln65 of FGF2 makes two hydrogen bonds with Asp320/Asp321 in the βC'-βE loop of FGFR1/FGFR2, and as a result, the βC'-βE loop is ordered in both FGF2-FGFR1 and FGF2-FGFR2 structures (Plotnikov et al., Cell 1999, 98:641-650; Plotnikov et al., Cell 2000, 101;413-424). In contrast, in the FGF1-FGFR1 structure the βC'-βE loop is disordered because Ser62 of FGF1 cannot interact with Asp320 of FGFR1 in the βC'-βE loop (Plotnikov et al., Cell 2000, 101:413-424). Thus, by analogy a skilled artisan would expect that Ser119 of FGF4 will also not make hydrogen bonds with Asp320 located in the βC'-βE loop. However, based on the present model, the side chain of Glu117 in FGF4 could make hydrogen bonds with Lys321 located in the βC'-βE loop of FGFR1. This interaction may potentially compensate for the inability of FGF4 to engage Asp320 and lead to an ordered βC'-βE loop. Moreover, in the FGF4-FGFR1 model, several solvent-exposed hydrophobic residues in FGF4 (Val121, Phe129, Phe136, Phe151) are in the vicinity of the βC'-βE loop of FGFR1 and could engage in hydrophobic contacts with Val-316 in the βC'-βE loop of FGFR1. These hydrophobic interactions would further contribute to the ordering of the βC'-βE loop in an FGF4-FGFR1 structure. DNA synthesis assays performed using mutant FGF4 molecules support the aforementioned hypothesis. Substitutions of Phe129 and Phe151 with alanine in FGF4 reduced the ability of FGF4 to induce thymidine-incorporation in NIH3T3 cells about a thousand-fold (Table 2, above). Mutation of the residue corresponding to Phe151 in FGF2 was also shown to be important for FGFR binding (Zhu et al., Protein Eng. 1998, 11:937-940).

Thus, the FGF4-FGFR1 model presented shows that FGF4, like FGF2, may engage the βC'-βE loop of FGFR1. Consequently, sequence variations in the βC'-βE loop resulting from alternative splicing should affect FGF4-FGFR binding affinity. A sequence comparison of FGFRs at the βC'-βE loop region demonstrates that Lys321 is conserved only in the IIIc isoforms of FGFR1-FGFR3, providing a potential explanation for reduced affinity of FGF4 towards the IIIb splice variants of FGFR1-FRFR3 and FGFR4.

Binding of the FGF4 mutants to FGFR2. Mutant FGF4 proteins were tested in a receptor binding assay to confirm that the diminished capacity of the mutant FGF4 proteins to induce DNA synthesis is a result of the reduced ability of the mutant FGF4 to interact with FGFR. CHO cells overexpressing FGFR2 (Mansukhani et al., Proc. Natl. Acad. Sci. U.S.A. 1992, 89:3305-3309) were allowed to bind radiolabeled N-terminal truncated FGF4 ($Gly^{79}$-$Leu^{206}$) in the presence of increasing concentrations of unlabeled full length (Ala$^{31}$-Leu$^{206}$), N-terminal truncated wild-type or various N-terminal truncated mutant FGF4 proteins (FIG. 4). The N-terminal truncated wild-type FGF4 bound FGFR2 with only a slightly lower affinity than full length FGF4 (Ala$^{31}$-Leu$^{206}$), indicating that the majority of receptor binding sites is contained within the Gly$^{79}$-Leu$^{206}$ construct (FIG. 4) Substitutions of Tyr87, Tyr166 and Leu203 with alanine severely reduced the affinity of FGF4 towards FGFR2 (FIG. 4 and Table 2, supra), emphasizing the importance of the hydrophobic FGF4-D2 interface in providing FGF4-FGFR affinity. In contrast, the R205A mutant FGF4 showed only a slight reduction in FGFR2 binding affinity. The relative decrease in binding affinity of these mutants towards FGFR2 is consistent with the results of the DNA synthesis assay, thus implying that the impaired ability of these mutants to induce DNA synthesis is a consequence of loss of binding affinity to FGFR2.

Alanine substitutions of FGF4 residues predicted to interact with D3 also reduced the binding affinity of FGF4 for FGFR2. The F129A mutant showed a large decrease (more than 100-fold) in receptor binding affinity, which paralleled the severe impairment of this mutant in induction of DNA synthesis (FIG. 4 and Table 2, supra). In contrast, the F151A and E159A mutants were only slightly affected (2.5- and 5-fold, respectively) in FGFR2 binding (FIG. 4 and Table 2), yet these mutants were severely compromised in induction of DNA synthesis (see, Table 2, above). This was particularly unexpected for the E159A mutant as Glu159 is highly conserved among FGFs (FIG. 2) and the corresponding glutamic acid in FGF2 (Glu96) was shown to be critical for binding of FGF2 to FGFR1 (Zhu et al., *J. Biol. Chem.* 1995, 270:21869-21874).

This discrepancy between receptor binding and DNA synthesis data for the F151A and E159A mutants may be due to a difference between the experimental conditions used for the receptor binding and for DNA synthesis assays. Since NIH 3T3 cells naturally express cell surface HSPG in abundance, they do not require exogenous heparin to respond fully to FGF4. Therefore, exogenous heparin was not included in the DNA synthesis assays. In contrast, receptor binding assays were also performed in the presence of exogenous heparin to exclude binding of FGF to the abundantly expressed cell surface HSPG. In the absence of heparin, binding to these low affinity but very abundant receptors can not easily be distinguished from binding to FGFR.

Since heparin stabilizes FGF-FGFR interactions, it was possible that the presence of exogenous heparin in the receptor binding assay could have partially reversed the reduced ability of the F151A and E159A mutants to interact with FGFR. To test this possibility, the DNA synthesis assays were repeated in the presence of exogenous soluble heparin. While, as expected, heparin had no effect on the mitogenic ability of wild type FGF4, heparin dramatically enhanced the capacity of the F151A and E159A mutants to induce DNA synthesis (FIG. 5A and Table 2, above). In contrast, addition of heparin had no effect on the Y87A, F129A, Y166A and L203A mutants and enhanced the ability of R205A to induce DNA synthesis only by about ten-fold (shown in FIG. 5A, and in Table 2).

Analysis of the location of the various FGF4 mutations in the ternary FGF4-FGFR1-heparin model provides a potential explanation for the differential ability of heparin to rescue only some of the mutants. Both the F115A and E159A mutations, which display the greatest potentiation upon addition of heparin, affect FGF4 interaction with FGFR D3 (FIG. 2). In contrast, with the exception of the F129A mutant, all the mutations that are not rescued by heparin affect FGF4 interaction with FGFR D2. Upon binding of FGF to FGFR, a continuous negatively charged surface is formed by the heparin binding sites of FGF and FGFR D2, to which heparin binds (Plotnikov et al., *Cell* 1999, 98:641-650). Simultaneous binding of the same heparin polymer to both FGF and FGFR will clearly increase apparent FGF-FGFR affinity (Schlessinger et al., *Mol. Cell* 2000, 6:743-750). Mutations affecting the FGF-D2 interface will hamper a productive juxtaposition of the heparin binding sites of FGF and FGFR to form a continuous heparin binding surface, and thus heparin will not reverse the deleterious effects of these mutations. In contrast, mutations affecting the FGF-D3 interface will not interfere with the formation of a productive heparin binding surface by FGF and FGFR D2, and heparin can enhance FGF-FGFR affinity by interacting with both FGF and FGFR D2.

The mutagenesis data suggest that interactions of FGF with FGFR D2 provide the primary FGF-FGFR binding affinity. Indeed, Wang et al. (*Biochemistry* 1999, 38:160-171) have shown that several FGFs can bind to the isolated D2 domain of FGFR1 in vitro in the presence of heparin. Such teaching, coupled with what is taught, supra, in these examples, indicates that FGFR binds FGF first via D2. Heparin then may stabilize the FGF-D2 interaction and facilitates formation of a FGF-D3 interface.

Heparin binding sites. Recent biochemical and structural data demonstrate that FGF in the absence of heparin can form an initial low affinity complex with FGFR (Pantoliano et al., *Biochemistry* 1994, 33:10229-10248). In the presence of heparin, the low affinity complexes become stabilized which then in turn lead to stable 2:2 FGF:FGFR signaling complexes. The recent crystal structure of a dimeric 2:2:2 FGF2:FGFR1:heparin complex provides a molecular basis for how heparin enhances FGF-FGFR affinity and promotes dimerization (Schlessinger et al., *Mol. Cell* 2000, 6:743-750). Within each ternary 1:1:1 FGF:FGFR:heparin complex, heparin makes numerous contacts with the heparin binding residues of FGF and FGFR, thereby increasing the affinity of FGF towards FGFRs. In addition, heparin also interacts with the heparin binding residues in D2 of the adjoining FGFR, thereby augmenting the weak interactions of FGF and FGFR in one ternary complex with the FGFR in the adjoining ternary complex. Since FGFs differ in the primary sequences of heparin binding sites, each FGF may require different heparin motifs (e.g., different sulfation patterns and/or lengths) to exert its optimal biological activities (Faham et al., *Curr. Opin. Struct. Biol.* 1998, 8:578-586; Schlessinger et al., *Mol. Cell* 2000, 6:743-750).

To evaluate the potential heparin binding sites of FGF4, a dimeric FGF4-FGFR-heparin model was generated by superimposing two copies of the FGF4 structure onto the two copies of FGF2 in the dimeric FGF2-FGFR1-heparin ternary complex (FIG. 6). FGF4 residues corresponding to the heparin binding residues of FGF2 along with other FGF4 surface residues that could bind heparin were mapped onto the ribbon diagram of FGF4 (data not shown). With the exception of Lys188 (Lys134 in FGF2) and Lys198 (Lys144 in FGF2) the remainder of the heparin binding residues differs between FGF4 and FGF2 (FIG. 2). These differences are likely to determine the optimal sulfation motifs in heparin that are required to support FGF4 or FGF2 biological activities. Interestingly, Asn36 and Gln143, two critical heparin binding residues in FGF2, are substituted by hydrophobic residues Val90 and Met197 in FGF4 (FIG. 2). Therefore, these residues are unable to make hydrogen bonds with the hydroxyl group and N-sulfate group of ring D of heparin. Moreover, in the model the side chain of Val199 in FGF4 (Ala145 in FGF2) clashes with the N-sulfate of ring D (data not shown). These observations indicate that FGF4 may not require N-sulfate on ring D for heparin binding. Two other significant differences between FGF2 and FGF4 are the substitutions of Lys35 and Lys128 of FGF2 with Asn89 and Ser182, respectively, in FGF4 (FIG. 2). Based on the present model, Asn89 and Ser182 would engage better the 6-O-sulfate of ring B and the 2-O-sulfate group of ring E (data not shown).

A sulfate ion (provided by the crystallization buffer) is coordinated at the predicted high affinity heparin-binding site of FGF4 by Lys183 and Lys188 (data not shown). These two lysines are expected to bind the 2-O-sulfate group of ring E of heparin. In fact the sulfate ion in the FGF4 structure nearly colocalizes with the 2-O-sulfate group of ring E in the FGF4-heparin model (data not shown). To provide experimental support for the modeled FGF4-heparin interactions, mutant FGF4 proteins were generated in which FGF4 residues predicted to coordinate the 2-O-sulfate of ring E (K183 and K188) or the 6-O-sulfate of ring B (N89 and K198) are substituted with alanines. Both the doubly mutated K183A/K188A and N89A/K198A FGF4 proteins showed diminished ability to induce DNA synthesis in NIH3T3 cells (see, FIG. 5B and Table 2). Mutations in all four (4) amino acid residues abolishes all FGF4 activity (Table 2). Thus, as for FGF2, both the 6-O-sulfate of ring B and the 2-O-sulfate group of ring E of heparin may play important roles in promoting heparin-dependent FGF-FGFR interaction and dimerization. These data are consistent with findings that a high content in 6-O-sulfate groups in heparin is required for specific interaction with FGF4 (Ishihara, *Blycolbiology* 1994, 4:817-824).

Another sulfate ion is coordinated by the side chains of Arg103, Lys144 in the crystal structure of FGF4 (data not shown). Since bound sulfate ions in the crystal structures of free FGFs often indicate potential heparin binding sites in FGFs a doubly mutated R103/K144 FGF4 protein was also generated. This mutant FGF4 protein induced DNA synthesis in NIH3T3 cells to a level comparable to wild-type FGF4 (see, Table 2), suggesting that Arg103 and Lys144 most likely do not participate in heparin binding.

Experiments were also performed to determined whether exogenous heparin can compensate for the reduced ability of the K183A/K188A and N89A/K198A mutant FGF4 proteins in the DNA synthesis assay. As shown in FIG. 5B, exogenously added heparin significantly enhanced the ability of the K183A/K188A mutant FGF4 to induce DNA synthesis, but had no effect on the N89A/K198A mutant. A possible explanation for the differential effect of heparin on the activity of these two mutants lies in the heterogenous nature of commercial heparin. It is known that heparin is a mixture of oligosaccharides of different length and sulfate contents, generated by the polymerization of repeating disaccharide units consisting of D-glucoseamine (GlcN) and L-iduronic acid (IdoA). During biosynthesis, heparin is sulfated by the sequential actions of three different sulfotransferases, an N-sulfotransferase, a 2-O-sulfotransferase and a 6-O-sulfotransferase (Lindahl et al., *J. Biol. Chem.* 1998, 273: 24979-24982). In general, these reactions proceed in the order indicated, but often fail to go to completion, resulting in tremendous chemical heterogeneity in sulfation pattern in heparin. The observation that addition of exogenous heparin partially rescues only the K183A/K188A mutant (predicted to coordinate 6-O-sulfate) and not the N89A/K198A mutant (predicted to coordinate 2-O-sulfate), is probably due to the fact that the heparin sub-fraction containing 2-O-sulfate is more abundant than the sub-fraction containing 6-O-sulfate.

The heterogeneity in sulfation pattern is even more profound in heparan sulfate moieties of cell surface HSPG, which are thought to cooperate with FGFs to induce FGFR dimerization and activation. The requirement for a specific sulfation motif in heparan sulfate for optimal FGF4 action may be a mechanism to fine tune FGF4-FGFR interactions and to restrict FGF4 signaling to a specific set of cells in a specific tissue during various stages of embryonic development, where spatial and temporal regulation by FGF is critically required.

Implications for tile general mode of FGF-FGFR binding. Those skilled in the art will note that some of the data presented here is not consistent with the model of FGF1-FGFR2 binding described in the recently published crystal structure of a ternary FGF1-FGFR2-heparin complex (Pellegrini et al., *Nature* 2000, 407:1029-1034). In the novel structure presented in Pellegrini, the FGFR-invariant Pro-253 located in the D2-D3 linker, is found in a cis configuration, while in all previously reported binary FGF-FGFR structures Pro253 is found only in a trans configuration (Plotnikov et al., *Cell* 1999, 98:641-650; Plotnikov et al., *Cell* 2000, 101:413-424; Stauber et al., *Proc. Natl. Acad. Sci. U.S.A.* 2000, 97:49-54). Consequently, relative to its position in all binary FGF-FGFR structures, the receptor D3 in the ternary FGF1-FGFR2-heparin structure is swiveled around the linker region by more than 160°. This creates a completely different set of interactions at the FGF-D3 interface. Pellegrini et al. (*Nature* 2000, 407:1029-1034) propose that this D3 rotation is caused by a heparin-mediated trans to cis isomerization of Pro253 in the D2-D3 linker region. However, the mutagenesis data presented here do not support this hypothesis. Based on this ternary FGF1-FGFR2-heparin structure (Pellegrini et al., supra), neither F129 nor F151 in FGF4 are predicted to make any contacts with D3 (FIG. 6). Thus, the drastically reduced mitogenic capacity of the F129A and F151A mutants is in disagreement with the mode of FGF-FGFR binding described by those authors (i.e., by Pellegrini et al., supra) Surprisingly, the data presented here suggested that the cis isomerization of Pro253 observed in the FGF1-FGFR2-heparin structure (Pellegrini et al., supra) is probably the result of partial refolding of FGFR2.

The present invention is therefore based on a different model of FGF-FGFR binding, presented supra, in which interaction of FGF with the FGFR D2 domain provides the primary FGF-FGFR binding surface (FIG. 7A-B), and heparin facilitates the formation of an FGF-D3 interface by stabilizing the FGF-D2 interaction (FIG. 9A-B). This model may explain the exclusively heparin-dependent binding of FGF1 to an in vitro refolded FGFR2 described by Pellegrini et al. (supra). As discussed above, it is likely that the FGFR2 used by these authors was not properly refolded and consequently D3 is in a different position than the one observed in the previously reported FGF-FGFR crystal structures. Despite the lack of sufficient contact between FGF1 and FGFR2 D3, the FGF1-FGFR2 complex could still be captured in the presence of heparin as evident from the crystal structure (Pellegrini et al., supra).

The data presented here show that FGF4 adopts a typical β-trefoil fold similar to that adopted by other FGFs (see, e.g., Osslund et al., *Protein Sci.* 1998, 7:1681-1690; Plotnikov et al., *J. Biol. Chem.* 2001, 276:4322-4329; Zhu et al., *J. Biol. Chem.* 1995, 270:21869-21874). The ternary FGF4-FGFR1-heparin model constructed, above, by superimposing FGF4 onto FGF2 in the FGF2-FGFR1-heparin structure assists identification of several key residues in FGF4 involved in receptor and heparin binding. Substitution of several of these residues with alanine produces FGF4 molecules with reduced receptor binding and mitogenic potential, which may, at least in certain cases, be partially reversed by excess soluble heparin. Significantly, the modeling and mutagenesis data presented here show that FGF4 interacts with the βC'-βE loop in FGFR D3 and provide a molecular basis for why FGF4, like FGF2 but unlike FGF1, can discriminate between the IIIc and IIIb splice variants of FGFRs for binding. Based on these findings, a skilled artisan may readily identify specific FGF-FGFR interactions and, from these, design novel, variant FGF molecules with increased or altered binding specificity.

7. References Cited

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

8. Appendix A: One and Three Letter Designations for Amino Acids

| Alanine | Ala | A | Isoleucine | Ile | I |
|---|---|---|---|---|---|
| Arginine | Arg | R | Leucine | Leu | L |
| Asparagine | Asn | N | Lysine | Lys | K |
| Aspartic acid | Asp | D | Methionine | Met | M |
| Cysteine | Cys | C | Phenylalanine | Phe | F |
| Glutamine | Gln | Q | Proline | Pro | P |
| Glutamic acid | Glu | E | Serine | Ser | S |
| Glycine | Gly | G | Threonine | Thr | T |
| Histidine | His | H | Tryptophan | Trp | W |
| Tyrosine | Tyr | Y | Valine | Val | V |

9. Appendix B: Crystal Structure Coordinates for FGF4 (SEQ ID NO: 20)

```
REMARK coordinates from restrained individual B-factor refinement
REMARK refinement resolution: 30–1.8 A
REMARK starting r = 0.1944 free_r = 0.2070
REMARK final r = 0.1943 free_r = 0.2067
REMARK B rmsd for bonded mainchain atoms = 0.695 target = 1.5
REMARK B rmsd for bonded sidechain atoms = 1.228 target = 2.0
REMARK B rmsd for angle mainchain atoms = 1.094 target = 2.0
REMARK B rmsd for angle sidechain atoms = 1.939 target = 2.5
REMARK wa = 0.911288
REMARK rweight = 0.235168
REMARK target = mlf steps = 30
REMARK sg = P2(1)2(1)2 (1) a = 40.367 b = 53.295 c = 56.231 alpha = 90 beta = 90 gamma = 90
REMARK parameter file 1: CNS_TOPPAR: protein_rep.param
REMARK parameter file 2: CNS_TOPPAR: dna-rna.param
REMARK parameter file 3: CNS_TOPPAR: water_rep.param
REMARK parameter file 4: CNS_TOPPAR: ion.param
REMARK molecular structure file: fgf4_9.mtf
REMARK input coordinates: fgf4_9X.pdb
REMARK reflection file = fgf4.hklt
REMARK ncs = none
REMARK B-correction resolution: 6.0–1.8
REMARK initial B-factor correction applied to fobs:
REMARK B11 = -3.650 B22 = 0.683 B33 = 2.967
REMARK B12 = 0.000 B13 = 0.000 B23 = 0.000
REMARK B-factor correction applied to coordinate array B: 0.028
REMARK bulk solvent: density level = 0.570684 e/A^3, B-factor = 74.852 A^2
REMARK reflections with |Fobs|/sigma_F > 0.0 rejected
REMARK reflections with |Fobs| > 10000 * rms(Fobs) rejected
REMARK theoretical total number of refl. in resol. range:   11739 (100.0%)
REMARK number of unobserved reflections (no entry or |F| = 0):   251 (2.1%)
REMARK number of reflections rejected:                            0 (0.0%)
REMARK total number of reflections used:                     11488 (97.9%)
REMARK number of reflections in working set:                 10894 (92.8%)
REMARK number of reflections in test set:                      594 (5.1%)
CRYST1 40.367 53.295 56.231 90.00 90.00 90.00 P 21 21 21
REMARK FILENAME = "fgf4_9XB.pdb"
REMARK DATE: 25-Jan-00 22:33:40 created by user: mohammad
REMARK VERSION: 0.5
```

| ATOM | 1 | C   | GLY | 79 | 15.981 | 20.788 | 35.818 | 1.00 | 14.10 |
|------|---|-----|-----|----|--------|--------|--------|------|-------|
| ATOM | 2 | O   | GLY | 79 | 15.510 | 20.619 | 34.693 | 1.00 | 15.42 |
| ATOM | 3 | N   | GLY | 79 | 13.808 | 21.802 | 36.441 | 1.00 | 15.71 |
| ATOM | 4 | CA  | GLY | 79 | 15.211 | 21.566 | 36.865 | 1.00 | 14.54 |
| ATOM | 5 | N   | ILE | 80 | 17.165 | 20.308 | 36.178 | 1.00 | 12.57 |
| ATOM | 6 | CA  | ILE | 80 | 17.971 | 19.552 | 35.234 | 1.00 | 11.35 |
| ATOM | 7 | CB  | ILE | 80 | 19.443 | 19.416 | 35.728 | 1.00 | 11.22 |
| ATOM | 8 | CG2 | ILE | 80 | 20.089 | 20.790 | 35.818 | 1.00 | 10.86 |

-continued

| | | | | | | | | | |
|---|---|---|---|---|---|---|---|---|---|
| ATOM | 9 | CG1 | ILE | 80 | 19.497 | 18.729 | 37.096 | 1.00 | 11.55 |
| ATOM | 10 | CD1 | ILE | 80 | 19.441 | 17.210 | 37.040 | 1.00 | 12.63 |
| ATOM | 11 | C | ILE | 80 | 17.393 | 18.163 | 35.008 | 1.00 | 10.56 |
| ATOM | 12 | O | ILE | 80 | 16.667 | 17.637 | 35.852 | 1.00 | 9.79 |
| ATOM | 13 | N | LYS | 81 | 17.700 | 17.589 | 33.849 | 1.00 | 9.65 |
| ATOM | 14 | CA | LYS | 81 | 17.268 | 16.239 | 33.506 | 1.00 | 9.81 |
| ATOM | 15 | CB | LYS | 81 | 16.448 | 16.227 | 32.216 | 1.00 | 10.72 |
| ATOM | 16 | CG | LYS | 81 | 14.969 | 16.523 | 32.406 | 1.00 | 12.85 |
| ATOM | 17 | CD | LYS | 81 | 14.737 | 17.940 | 32.867 | 1.00 | 14.94 |
| ATOM | 18 | CE | LYS | 81 | 13.254 | 18.227 | 33.041 | 1.00 | 15.71 |
| ATOM | 19 | NZ | LYS | 81 | 13.025 | 19.662 | 33.354 | 1.00 | 17.00 |
| ATOM | 20 | C | LYS | 81 | 18.548 | 15.446 | 33.304 | 1.00 | 9.37 |
| ATOM | 21 | O | LYS | 81 | 19.457 | 15.896 | 32.613 | 1.00 | 9.66 |
| ATOM | 22 | N | ARG | 82 | 18.631 | 14.271 | 33.913 | 1.00 | 9.22 |
| ATOM | 23 | CA | ARG | 82 | 19.829 | 13.462 | 33.785 | 1.00 | 9.59 |
| ATOM | 24 | CB | ARG | 82 | 19.895 | 12.453 | 34.932 | 1.00 | 11.59 |
| ATOM | 25 | CG | ARG | 82 | 19.818 | 13.111 | 36.302 | 1.00 | 14.57 |
| ATOM | 26 | CD | ARG | 82 | 20.077 | 12.130 | 37.423 | 1.00 | 17.30 |
| ATOM | 27 | NE | ARG | 82 | 21.465 | 11.682 | 37.440 | 1.00 | 18.57 |
| ATOM | 28 | CZ | ARG | 82 | 21.982 | 10.905 | 38.384 | 1.00 | 20.23 |
| ATOM | 29 | NH1 | ARG | 82 | 21.222 | 10.491 | 39.392 | 1.00 | 21.72 |
| ATOM | 30 | NH2 | ARG | 82 | 23.258 | 10.545 | 38.325 | 1.00 | 20.18 |
| ATOM | 31 | C | ARG | 82 | 19.904 | 12.741 | 32.447 | 1.00 | 9.37 |
| ATOM | 32 | O | ARG | 82 | 18.891 | 12.279 | 31.920 | 1.00 | 8.91 |
| ATOM | 33 | N | LEU | 83 | 21.112 | 12.674 | 31.895 | 1.00 | 8.33 |
| ATOM | 34 | CA | LEU | 83 | 21.367 | 11.987 | 30.634 | 1.00 | 9.07 |
| ATOM | 35 | CB | LEU | 83 | 22.237 | 12.843 | 29.708 | 1.00 | 9.05 |
| ATOM | 36 | CG | LEU | 83 | 21.697 | 14.220 | 29.331 | 1.00 | 9.81 |
| ATOM | 37 | CD1 | LEU | 83 | 22.633 | 14.866 | 28.318 | 1.00 | 9.99 |
| ATOM | 38 | CD2 | LEU | 83 | 20.301 | 14.088 | 28.750 | 1.00 | 9.81 |
| ATOM | 39 | C | LEU | 83 | 22.133 | 10.747 | 31.055 | 1.00 | 10.07 |
| ATOM | 40 | O | LEU | 83 | 23.229 | 10.847 | 31.607 | 1.00 | 9.78 |
| ATOM | 41 | N | ARG | 84 | 21.561 | 9.576 | 30.812 | 1.00 | 9.78 |
| ATOM | 42 | CA | ARG | 84 | 22.220 | 8.354 | 31.234 | 1.00 | 11.27 |
| ATOM | 43 | CB | ARG | 84 | 21.635 | 7.907 | 32.573 | 1.00 | 13.30 |
| ATOM | 44 | CG | ARG | 84 | 21.624 | 9.002 | 33.617 | 1.00 | 16.93 |
| ATOM | 45 | CD | ARG | 84 | 22.305 | 8.543 | 34.881 | 1.00 | 18.68 |
| ATOM | 46 | NE | ARG | 84 | 21.347 | 8.127 | 35.893 | 1.00 | 21.27 |
| ATOM | 47 | CZ | ARG | 84 | 21.689 | 7.665 | 37.088 | 1.00 | 21.80 |
| ATOM | 48 | NH1 | ARG | 84 | 22.971 | 7.558 | 37.415 | 1.00 | 23.39 |
| ATOM | 49 | NH2 | ARG | 84 | 20.752 | 7.322 | 37.959 | 1.00 | 23.50 |
| ATOM | 50 | C | ARG | 84 | 22.098 | 7.212 | 30.253 | 1.00 | 9.55 |
| ATOM | 51 | O | ARG | 84 | 21.488 | 7.335 | 29.199 | 1.00 | 8.79 |
| ATOM | 52 | N | ARG | 85 | 22.712 | 6.095 | 30.617 | 1.00 | 9.72 |
| ATOM | 53 | CA | ARG | 85 | 22.632 | 4.886 | 29.823 | 1.00 | 9.53 |
| ATOM | 54 | CB | ARG | 85 | 24.026 | 4.410 | 29.393 | 1.00 | 11.00 |
| ATOM | 55 | CG | ARG | 85 | 24.690 | 5.336 | 28.390 | 1.00 | 13.65 |
| ATOM | 56 | CD | ARG | 85 | 25.824 | 4.654 | 27.640 | 1.00 | 15.37 |
| ATOM | 57 | NE | ARG | 85 | 26.269 | 5.472 | 26.517 | 1.00 | 18.74 |
| ATOM | 58 | CZ | ARG | 85 | 26.907 | 6.630 | 26.638 | 1.00 | 19.28 |
| ATOM | 59 | NH1 | ARG | 85 | 27.193 | 7.113 | 27.837 | 1.00 | 20.48 |
| ATOM | 60 | NH2 | ARG | 85 | 27.236 | 7.313 | 25.552 | 1.00 | 21.17 |
| ATOM | 61 | C | ARG | 85 | 21.981 | 3.873 | 30.751 | 1.00 | 9.35 |
| ATOM | 62 | O | ARG | 85 | 22.216 | 3.891 | 31.962 | 1.00 | 9.90 |
| ATOM | 63 | N | LEU | 86 | 21.128 | 3.024 | 30.194 | 1.00 | 8.17 |
| ATOM | 64 | CA | LEU | 86 | 20.452 | 2.000 | 30.978 | 1.00 | 7.93 |
| ATOM | 65 | CB | LEU | 86 | 18.945 | 2.045 | 30.711 | 1.00 | 7.25 |
| ATOM | 66 | CG | LEU | 86 | 18.309 | 3.365 | 31.168 | 1.00 | 7.91 |
| ATOM | 67 | CD1 | LEU | 86 | 16.839 | 3.414 | 30.769 | 1.00 | 7.67 |
| ATOM | 68 | CD2 | LEU | 86 | 18.448 | 3.496 | 32.681 | 1.00 | 7.54 |
| ATOM | 69 | C | LEU | 86 | 21.061 | 0.673 | 30.552 | 1.00 | 8.05 |
| ATOM | 70 | O | LEU | 86 | 20.845 | 0.199 | 29.437 | 1.00 | 7.14 |
| ATOM | 71 | N | TYR | 87 | 21.839 | 0.093 | 31.461 | 1.00 | 8.27 |
| ATOM | 72 | CA | TYR | 87 | 22.559 | −1.150 | 31.218 | 1.00 | 9.30 |
| ATOM | 73 | CB | TYR | 87 | 23.936 | −1.046 | 31.877 | 1.00 | 10.81 |
| ATOM | 74 | CG | TYR | 87 | 24.805 | −2.278 | 31.762 | 1.00 | 13.81 |
| ATOM | 75 | CD1 | TYR | 87 | 24.886 | −3.200 | 32.808 | 1.00 | 14.83 |
| ATOM | 76 | CE1 | TYR | 87 | 25.721 | −4.317 | 32.720 | 1.00 | 16.91 |
| ATOM | 77 | CD2 | TYR | 87 | 25.576 | −2.503 | 30.621 | 1.00 | 15.00 |
| ATOM | 78 | CE2 | TYR | 87 | 26.412 | −3.615 | 30.522 | 1.00 | 16.14 |
| ATOM | 79 | CZ | TYR | 87 | 26.481 | −4.514 | 31.575 | 1.00 | 16.64 |
| ATOM | 80 | OH | TYR | 87 | 27.319 | −5.601 | 31.483 | 1.00 | 19.14 |
| ATOM | 81 | C | TYR | 87 | 21.850 | −2.412 | 31.689 | 1.00 | 8.55 |
| ATOM | 82 | O | TYR | 87 | 21.529 | −2.552 | 32.865 | 1.00 | 7.71 |
| ATOM | 83 | N | CYS | 88 | 21.613 | −3.327 | 30.754 | 1.00 | 8.66 |
| ATOM | 84 | CA | CYS | 88 | 20.969 | −4.598 | 31.058 | 1.00 | 8.99 |
| ATOM | 85 | CB | CYS | 88 | 19.961 | −4.956 | 29.964 | 1.00 | 9.37 |
| ATOM | 86 | SG | CYS | 88 | 18.868 | −6.332 | 30.382 | 1.00 | 10.25 |
| ATOM | 87 | C | CYS | 88 | 22.094 | −5.630 | 31.102 | 1.00 | 9.81 |

-continued

| | | | | | | | | | |
|---|---|---|---|---|---|---|---|---|---|
| ATOM | 88 | O | CYS | 88 | 22.782 | −5.850 | 30.105 | 1.00 | 9.57 |
| ATOM | 89 | N | ASN | 89 | 22.278 | −6.262 | 32.256 | 1.00 | 10.42 |
| ATOM | 90 | CA | ASN | 89 | 23.353 | −7.228 | 32.416 | 1.00 | 11.44 |
| ATOM | 91 | CB | ASN | 89 | 23.800 | −7.259 | 33.882 | 1.00 | 12.56 |
| ATOM | 92 | CG | ASN | 89 | 25.097 | −8.023 | 34.078 | 1.00 | 14.22 |
| ATOM | 93 | OD1 | ASN | 89 | 25.975 | −7.997 | 33.217 | 1.00 | 14.10 |
| ATOM | 94 | ND2 | ASN | 89 | 25.229 | −8.693 | 35.219 | 1.00 | 14.82 |
| ATOM | 95 | C | ASN | 89 | 23.021 | −8.639 | 31.935 | 1.00 | 11.60 |
| ATOM | 96 | O | ASN | 89 | 23.029 | −9.589 | 32.717 | 1.00 | 12.87 |
| ATOM | 97 | N | VAL | 90 | 22.724 | −8.762 | 30.644 | 1.00 | 11.13 |
| ATOM | 98 | CA | VAL | 90 | 22.414 | −10.052 | 30.030 | 1.00 | 11.34 |
| ATOM | 99 | CB | VAL | 90 | 20.936 | −10.130 | 29.553 | 1.00 | 11.83 |
| ATOM | 100 | CG1 | VAL | 90 | 19.998 | −10.058 | 30.752 | 1.00 | 12.67 |
| ATOM | 101 | CG2 | VAL | 90 | 20.636 | −9.008 | 28.566 | 1.00 | 11.70 |
| ATOM | 102 | C | VAL | 90 | 23.344 | −10.214 | 28.830 | 1.00 | 10.91 |
| ATOM | 103 | O | VAL | 90 | 23.743 | −9.227 | 28.214 | 1.00 | 10.94 |
| ATOM | 104 | N | GLY | 91 | 23.689 | −11.451 | 28.490 | 1.00 | 11.30 |
| ATOM | 105 | CA | GLY | 91 | 24.596 | −11.655 | 27.377 | 1.00 | 11.22 |
| ATOM | 106 | C | GLY | 91 | 25.905 | −10.960 | 27.710 | 1.00 | 11.54 |
| ATOM | 107 | O | GLY | 91 | 26.358 | −11.021 | 28.851 | 1.00 | 11.96 |
| ATOM | 108 | N | ILE | 92 | 26.515 | −10.295 | 26.735 | 1.00 | 11.95 |
| ATOM | 109 | CA | ILE | 92 | 27.770 | −9.590 | 26.983 | 1.00 | 12.07 |
| ATOM | 110 | CB | ILE | 92 | 28.553 | −9.333 | 25.673 | 1.00 | 12.90 |
| ATOM | 111 | CG2 | ILE | 92 | 29.022 | −10.653 | 25.075 | 1.00 | 13.76 |
| ATOM | 112 | CG1 | ILE | 92 | 27.679 | −8.557 | 24.684 | 1.00 | 12.69 |
| ATOM | 113 | CD1 | ILE | 92 | 28.396 | −8.175 | 23.403 | 1.00 | 13.90 |
| ATOM | 114 | C | ILE | 92 | 27.526 | −8.241 | 27.661 | 1.00 | 11.76 |
| ATOM | 115 | O | ILE | 92 | 28.470 | −7.516 | 27.974 | 1.00 | 12.10 |
| ATOM | 116 | N | GLY | 93 | 26.258 | −7.912 | 27.888 | 1.00 | 11.33 |
| ATOM | 117 | CA | GLY | 93 | 25.921 | −6.643 | 28.513 | 1.00 | 10.40 |
| ATOM | 118 | C | GLY | 93 | 25.518 | −5.634 | 27.454 | 1.00 | 10.14 |
| ATOM | 119 | O | GLY | 93 | 26.279 | −5.386 | 26.514 | 1.00 | 9.39 |
| ATOM | 120 | N | PHE | 94 | 24.330 | −5.048 | 27.587 | 1.00 | 9.60 |
| ATOM | 121 | CA | PHE | 94 | 23.868 | −4.081 | 26.591 | 1.00 | 9.48 |
| ATOM | 122 | CB | PHE | 94 | 22.881 | −4.738 | 25.620 | 1.00 | 10.07 |
| ATOM | 123 | CG | PHE | 94 | 23.416 | −5.959 | 24.932 | 1.00 | 11.72 |
| ATOM | 124 | CD1 | PHE | 94 | 23.281 | −7.215 | 25.512 | 1.00 | 11.80 |
| ATOM | 125 | CD2 | PHE | 94 | 24.052 | −5.851 | 23.699 | 1.00 | 12.37 |
| ATOM | 126 | CE1 | PHE | 94 | 23.768 | −8.350 | 24.872 | 1.00 | 12.80 |
| ATOM | 127 | CE2 | PHE | 94 | 24.544 | −6.977 | 23.052 | 1.00 | 13.09 |
| ATOM | 128 | CZ | PHE | 94 | 24.402 | −8.229 | 23.637 | 1.00 | 13.50 |
| ATOM | 129 | C | PHE | 94 | 23.196 | −2.837 | 27.162 | 1.00 | 9.07 |
| ATOM | 130 | O | PHE | 94 | 22.530 | −2.898 | 28.194 | 1.00 | 9.31 |
| ATOM | 131 | N | HIS | 95 | 23.372 | −1.712 | 26.473 | 1.00 | 9.61 |
| ATOM | 132 | CA | HIS | 95 | 22.739 | −0.454 | 26.868 | 1.00 | 8.83 |
| ATOM | 133 | CB | HIS | 95 | 23.667 | 0.755 | 26.670 | 1.00 | 9.80 |
| ATOM | 134 | CG | HIS | 95 | 24.991 | 0.636 | 27.356 | 1.00 | 11.64 |
| ATOM | 135 | CD2 | HIS | 95 | 25.374 | 0.950 | 28.614 | 1.00 | 11.84 |
| ATOM | 136 | ND1 | HIS | 95 | 26.112 | 0.151 | 26.722 | 1.00 | 12.48 |
| ATOM | 137 | CE1 | HIS | 95 | 27.133 | 0.170 | 27.559 | 1.00 | 12.86 |
| ATOM | 138 | NE2 | HIS | 95 | 26.712 | 0.650 | 28.717 | 1.00 | 13.05 |
| ATOM | 139 | C | HIS | 95 | 21.544 | −0.270 | 25.940 | 1.00 | 8.68 |
| ATOM | 140 | O | HIS | 95 | 21.663 | −0.449 | 24.728 | 1.00 | 8.37 |
| ATOM | 141 | N | LEU | 96 | 20.397 | 0.086 | 26.505 | 1.00 | 7.77 |
| ATOM | 142 | CA | LEU | 96 | 19.198 | 0.312 | 25.711 | 1.00 | 7.43 |
| ATOM | 143 | CB | LEU | 96 | 18.028 | 0.661 | 26.634 | 1.00 | 7.74 |
| ATOM | 144 | CG | LEU | 96 | 16.658 | 0.911 | 26.000 | 1.00 | 7.64 |
| ATOM | 145 | CD1 | LEU | 96 | 16.145 | −0.363 | 25.333 | 1.00 | 8.64 |
| ATOM | 146 | CD2 | LEU | 96 | 15.689 | 1.369 | 27.083 | 1.00 | 7.70 |
| ATOM | 147 | C | LEU | 96 | 19.485 | 1.479 | 24.763 | 1.00 | 7.66 |
| ATOM | 148 | O | LEU | 96 | 20.047 | 2.492 | 25.177 | 1.00 | 6.82 |
| ATOM | 149 | N | GLN | 97 | 19.120 | 1.341 | 23.493 | 1.00 | 7.35 |
| ATOM | 150 | CA | GLN | 97 | 19.369 | 2.430 | 22.556 | 1.00 | 8.13 |
| ATOM | 151 | CB | GLN | 97 | 20.675 | 2.190 | 21.787 | 1.00 | 9.41 |
| ATOM | 152 | CG | GLN | 97 | 20.610 | 1.130 | 20.698 | 1.00 | 11.56 |
| ATOM | 153 | CD | GLN | 97 | 21.901 | 1.049 | 19.892 | 1.00 | 13.36 |
| ATOM | 154 | OE1 | GLN | 97 | 22.723 | 1.967 | 19.919 | 1.00 | 14.09 |
| ATOM | 155 | NE2 | GLN | 97 | 22.076 | −0.045 | 19.159 | 1.00 | 13.35 |
| ATOM | 156 | C | GLN | 97 | 18.231 | 2.650 | 21.571 | 1.00 | 7.87 |
| ATOM | 157 | O | GLN | 97 | 17.467 | 1.735 | 21.265 | 1.00 | 6.47 |
| ATOM | 158 | N | ALA | 98 | 18.119 | 3.884 | 21.091 | 1.00 | 7.19 |
| ATOM | 159 | CA | ALA | 98 | 17.094 | 4.242 | 20.122 | 1.00 | 7.41 |
| ATOM | 160 | CB | ALA | 98 | 16.259 | 5.399 | 20.650 | 1.00 | 6.51 |
| ATOM | 161 | C | ALA | 98 | 17.817 | 4.642 | 18.839 | 1.00 | 7.88 |
| ATOM | 162 | O | ALA | 98 | 18.651 | 5.549 | 18.846 | 1.00 | 7.94 |
| ATOM | 163 | N | LEU | 99 | 17.504 | 3.960 | 17.743 | 1.00 | 8.72 |
| ATOM | 164 | CA | LEU | 99 | 18.149 | 4.237 | 16.465 | 1.00 | 9.77 |
| ATOM | 165 | CB | LEU | 99 | 18.245 | 2.946 | 15.651 | 1.00 | 10.44 |
| ATOM | 166 | CG | LEU | 99 | 19.040 | 1.816 | 16.318 | 1.00 | 11.58 |

-continued

| | | | | | | | | |
|---|---|---|---|---|---|---|---|---|
| ATOM | 167 | CD1 | LEU | 99 | 19.132 | 0.639 | 15.367 | 1.00 | 13.27 |
| ATOM | 168 | CD2 | LEU | 99 | 20.433 | 2.299 | 16.678 | 1.00 | 11.97 |
| ATOM | 169 | C | LEU | 99 | 17.441 | 5.321 | 15.657 | 1.00 | 9.49 |
| ATOM | 170 | O | LEU | 99 | 16.262 | 5.599 | 15.871 | 1.00 | 10.13 |
| ATOM | 171 | N | PRO | 100 | 18.159 | 5.943 | 14.709 | 1.00 | 9.88 |
| ATOM | 172 | CD | PRO | 100 | 19.583 | 5.707 | 14.403 | 1.00 | 10.62 |
| ATOM | 173 | CA | PRO | 100 | 17.615 | 7.006 | 13.858 | 1.00 | 10.16 |
| ATOM | 174 | CB | PRO | 100 | 18.847 | 7.512 | 13.105 | 1.00 | 10.38 |
| ATOM | 175 | CG | PRO | 100 | 19.707 | 6.290 | 13.012 | 1.00 | 11.95 |
| ATOM | 176 | C | PRO | 100 | 16.482 | 6.603 | 12.921 | 1.00 | 9.96 |
| ATOM | 177 | O | PRO | 100 | 15.811 | 7.471 | 12.358 | 1.00 | 9.98 |
| ATOM | 178 | N | ASP | 101 | 16.261 | 5.301 | 12.743 | 1.00 | 9.35 |
| ATOM | 179 | CA | ASP | 101 | 15.175 | 4.862 | 11.874 | 1.00 | 8.93 |
| ATOM | 180 | CB | ASP | 101 | 15.613 | 3.683 | 10.988 | 1.00 | 8.94 |
| ATOM | 181 | CG | ASP | 101 | 16.058 | 2.464 | 11.779 | 1.00 | 9.32 |
| ATOM | 182 | OD1 | ASP | 101 | 16.005 | 2.478 | 13.028 | 1.00 | 7.56 |
| ATOM | 183 | OD2 | ASP | 101 | 16.467 | 1.474 | 11.132 | 1.00 | 9.79 |
| ATOM | 184 | C | ASP | 101 | 13.923 | 4.499 | 12.668 | 1.00 | 8.49 |
| ATOM | 185 | O | ASP | 101 | 12.914 | 4.074 | 12.098 | 1.00 | 7.97 |
| ATOM | 186 | N | GLY | 102 | 13.992 | 4.681 | 13.985 | 1.00 | 7.41 |
| ATOM | 187 | CA | GLY | 102 | 12.851 | 4.386 | 14.835 | 1.00 | 6.68 |
| ATOM | 188 | C | GLY | 102 | 12.906 | 3.057 | 15.562 | 1.00 | 6.54 |
| ATOM | 189 | O | GLY | 102 | 12.011 | 2.740 | 16.344 | 1.00 | 6.36 |
| ATOM | 190 | N | ARG | 103 | 13.946 | 2.268 | 15.316 | 1.00 | 5.93 |
| ATOM | 191 | CA | ARG | 103 | 14.068 | 0.982 | 15.987 | 1.00 | 6.49 |
| ATOM | 192 | CB | ARG | 103 | 14.961 | 0.034 | 15.174 | 1.00 | 7.14 |
| ATOM | 193 | CG | ARG | 103 | 14.338 | −0.417 | 13.854 | 1.00 | 8.91 |
| ATOM | 194 | CD | ARG | 103 | 15.206 | −1.444 | 13.124 | 1.00 | 11.34 |
| ATOM | 195 | NE | ARG | 103 | 15.547 | −2.579 | 13.979 | 1.00 | 13.84 |
| ATOM | 196 | CZ | ARG | 103 | 16.740 | −2.764 | 14.540 | 1.00 | 15.57 |
| ATOM | 197 | NH1 | ARG | 103 | 16.956 | −3.823 | 15.309 | 1.00 | 16.83 |
| ATOM | 198 | NH2 | ARG | 103 | 17.725 | −1.901 | 14.317 | 1.00 | 15.44 |
| ATOM | 199 | C | ARG | 103 | 14.632 | 1.154 | 17.394 | 1.00 | 6.57 |
| ATOM | 200 | O | ARG | 103 | 15.241 | 2.175 | 17.713 | 1.00 | 7.34 |
| ATOM | 201 | N | ILE | 104 | 14.404 | 0.149 | 18.230 | 1.00 | 5.76 |
| ATOM | 202 | CA | ILE | 104 | 14.883 | 0.138 | 19.606 | 1.00 | 6.17 |
| ATOM | 203 | CB | ILE | 104 | 13.705 | 0.097 | 20.621 | 1.00 | 5.44 |
| ATOM | 204 | CG2 | ILE | 104 | 14.243 | 0.072 | 22.047 | 1.00 | 5.86 |
| ATOM | 205 | CG1 | ILE | 104 | 12.780 | 1.306 | 20.427 | 1.00 | 5.60 |
| ATOM | 206 | CD1 | ILE | 104 | 13.424 | 2.652 | 20.740 | 1.00 | 6.40 |
| ATOM | 207 | C | ILE | 104 | 15.704 | −1.146 | 19.752 | 1.00 | 6.60 |
| ATOM | 208 | O | ILE | 104 | 15.334 | −2.190 | 19.208 | 1.00 | 6.24 |
| ATOM | 209 | N | GLY | 105 | 16.820 | −1.071 | 20.468 | 1.00 | 6.98 |
| ATOM | 210 | CA | GLY | 105 | 17.641 | −2.255 | 20.645 | 1.00 | 8.04 |
| ATOM | 211 | C | GLY | 105 | 18.680 | −2.100 | 21.737 | 1.00 | 8.60 |
| ATOM | 212 | O | GLY | 105 | 18.540 | −1.255 | 22.620 | 1.00 | 8.84 |
| ATOM | 213 | N | GLY | 106 | 19.723 | −2.923 | 21.674 | 1.00 | 8.72 |
| ATOM | 214 | CA | GLY | 106 | 20.779 | −2.861 | 22.667 | 1.00 | 9.01 |
| ATOM | 215 | C | GLY | 106 | 22.146 | −2.743 | 22.021 | 1.00 | 8.89 |
| ATOM | 216 | O | GLY | 106 | 22.356 | −3.219 | 20.905 | 1.00 | 8.84 |
| ATOM | 217 | N | ALA | 107 | 23.072 | −2.092 | 22.715 | 1.00 | 8.61 |
| ATOM | 218 | CA | ALA | 107 | 24.432 | −1.920 | 22.213 | 1.00 | 9.67 |
| ATOM | 219 | CB | ALA | 107 | 24.604 | −0.528 | 21.620 | 1.00 | 10.06 |
| ATOM | 220 | C | ALA | 107 | 25.409 | −2.124 | 23.364 | 1.00 | 10.28 |
| ATOM | 221 | O | ALA | 107 | 25.273 | −1.508 | 24.418 | 1.00 | 9.28 |
| ATOM | 222 | N | HIS | 108 | 26.391 | −2.995 | 23.161 | 1.00 | 11.70 |
| ATOM | 223 | CA | HIS | 108 | 27.374 | −3.270 | 24.198 | 1.00 | 12.04 |
| ATOM | 224 | CB | HIS | 108 | 28.253 | −4.455 | 23.786 | 1.00 | 13.11 |
| ATOM | 225 | CG | HIS | 108 | 29.307 | −4.801 | 24.792 | 1.00 | 14.15 |
| ATOM | 226 | CD2 | HIS | 108 | 30.657 | −4.798 | 24.702 | 1.00 | 14.78 |
| ATOM | 227 | ND1 | HIS | 108 | 29.008 | −5.191 | 26.079 | 1.00 | 14.21 |
| ATOM | 228 | CE1 | HIS | 108 | 30.129 | −5.412 | 26.741 | 1.00 | 15.02 |
| ATOM | 229 | NE2 | HIS | 108 | 31.146 | −5.181 | 25.927 | 1.00 | 16.19 |
| ATOM | 230 | C | HIS | 108 | 28.244 | −2.048 | 24.480 | 1.00 | 12.52 |
| ATOM | 231 | O | HIS | 108 | 28.554 | −1.752 | 25.633 | 1.00 | 12.77 |
| ATOM | 232 | N | ALA | 109 | 28.631 | −1.334 | 23.429 | 1.00 | 13.09 |
| ATOM | 233 | CA | ALA | 109 | 29.470 | −0.150 | 23.587 | 1.00 | 13.18 |
| ATOM | 234 | CB | ALA | 109 | 30.199 | 0.147 | 22.280 | 1.00 | 14.30 |
| ATOM | 235 | C | ALA | 109 | 28.654 | 1.067 | 24.016 | 1.00 | 13.45 |
| ATOM | 236 | O | ALA | 109 | 27.423 | 1.040 | 23.985 | 1.00 | 12.92 |
| ATOM | 237 | N | ASP | 110 | 29.344 | 2.127 | 24.427 | 1.00 | 13.54 |
| ATOM | 238 | CA | ASP | 110 | 28.674 | 3.355 | 24.841 | 1.00 | 14.78 |
| ATOM | 239 | CB | ASP | 110 | 29.548 | 4.164 | 25.807 | 1.00 | 16.93 |
| ATOM | 240 | CG | ASP | 110 | 29.747 | 3.470 | 27.143 | 1.00 | 19.56 |
| ATOM | 241 | OD1 | ASP | 110 | 28.758 | 2.968 | 27.715 | 1.00 | 20.96 |
| ATOM | 242 | OD2 | ASP | 110 | 30.897 | 3.442 | 27.631 | 1.00 | 21.98 |
| ATOM | 243 | C | ASP | 110 | 28.375 | 4.190 | 23.599 | 1.00 | 13.85 |
| ATOM | 244 | O | ASP | 110 | 28.956 | 5.257 | 23.399 | 1.00 | 13.85 |
| ATOM | 245 | N | THR | 111 | 27.465 | 3.687 | 22.773 | 1.00 | 12.59 |

-continued

| | | | | | | | | |
|---|---|---|---|---|---|---|---|---|
| ATOM | 246 | CA | THR | 111 | 27.066 | 4.351 | 21.532 | 1.00 | 11.75 |
| ATOM | 247 | CB | THR | 111 | 26.120 | 3.456 | 20.709 | 1.00 | 11.78 |
| ATOM | 248 | OG1 | THR | 111 | 24.926 | 3.205 | 21.464 | 1.00 | 11.42 |
| ATOM | 249 | CG2 | THR | 111 | 26.783 | 2.133 | 20.378 | 1.00 | 11.72 |
| ATOM | 250 | C | THR | 111 | 26.340 | 5.666 | 21.779 | 1.00 | 11.02 |
| ATOM | 251 | O | THR | 111 | 25.736 | 5.864 | 22.831 | 1.00 | 10.14 |
| ATOM | 252 | N | ARG | 112 | 26.397 | 6.565 | 20.799 | 1.00 | 10.53 |
| ATOM | 253 | CA | ARG | 112 | 25.715 | 7.845 | 20.918 | 1.00 | 10.82 |
| ATOM | 254 | CB | ARG | 112 | 25.941 | 8.701 | 19.669 | 1.00 | 12.11 |
| ATOM | 255 | CG | ARG | 112 | 27.380 | 9.110 | 19.432 | 1.00 | 14.73 |
| ATOM | 256 | CD | ARG | 112 | 27.470 | 9.990 | 18.198 | 1.00 | 17.34 |
| ATOM | 257 | NE | ARG | 112 | 28.842 | 10.372 | 17.886 | 1.00 | 19.56 |
| ATOM | 258 | CZ | ARG | 112 | 29.169 | 11.260 | 16.955 | 1.00 | 20.19 |
| ATOM | 259 | NH1 | ARG | 112 | 28.218 | 11.857 | 16.248 | 1.00 | 21.18 |
| ATOM | 260 | NH2 | ARG | 112 | 30.443 | 11.552 | 16.729 | 1.00 | 21.74 |
| ATOM | 261 | C | ARG | 112 | 24.220 | 7.604 | 21.083 | 1.00 | 10.26 |
| ATOM | 262 | O | ARG | 112 | 23.562 | 8.275 | 21.874 | 1.00 | 10.16 |
| ATOM | 263 | N | ASP | 113 | 23.694 | 6.635 | 20.335 | 1.00 | 9.55 |
| ATOM | 264 | CA | ASP | 113 | 22.270 | 6.319 | 20.385 | 1.00 | 9.39 |
| ATOM | 265 | CB | ASP | 113 | 21.875 | 5.410 | 19.214 | 1.00 | 9.84 |
| ATOM | 266 | CG | ASP | 113 | 21.993 | 6.103 | 17.867 | 1.00 | 11.80 |
| ATOM | 267 | OD1 | ASP | 113 | 22.074 | 7.351 | 17.838 | 1.00 | 12.79 |
| ATOM | 268 | OD2 | ASP | 113 | 21.991 | 5.402 | 16.833 | 1.00 | 11.25 |
| ATOM | 269 | C | ASP | 113 | 21.802 | 5.686 | 21.690 | 1.00 | 8.59 |
| ATOM | 270 | O | ASP | 113 | 20.604 | 5.473 | 21.876 | 1.00 | 7.24 |
| ATOM | 271 | N | SER | 114 | 22.730 | 5.386 | 22.595 | 1.00 | 8.92 |
| ATOM | 272 | CA | SER | 114 | 22.343 | 4.794 | 23.871 | 1.00 | 8.63 |
| ATOM | 273 | CB | SER | 114 | 23.294 | 3.650 | 24.256 | 1.00 | 9.68 |
| ATOM | 274 | OG | SER | 114 | 24.625 | 4.100 | 24.427 | 1.00 | 10.49 |
| ATOM | 275 | C | SER | 114 | 22.286 | 5.836 | 24.989 | 1.00 | 8.56 |
| ATOM | 276 | O | SER | 114 | 22.042 | 5.495 | 26.145 | 1.00 | 8.23 |
| ATOM | 277 | N | LEU | 115 | 22.520 | 7.103 | 24.651 | 1.00 | 7.61 |
| ATOM | 278 | CA | LEU | 115 | 22.445 | 8.164 | 25.652 | 1.00 | 7.24 |
| ATOM | 279 | CB | LEU | 115 | 23.260 | 9.386 | 25.230 | 1.00 | 8.19 |
| ATOM | 280 | CG | LEU | 115 | 23.344 | 10.488 | 26.292 | 1.00 | 8.61 |
| ATOM | 281 | CD1 | LEU | 115 | 24.133 | 9.981 | 27.504 | 1.00 | 9.28 |
| ATOM | 282 | CD2 | LEU | 115 | 24.015 | 11.717 | 25.703 | 1.00 | 9.34 |
| ATOM | 283 | C | LEU | 115 | 20.972 | 8.534 | 25.745 | 1.00 | 6.88 |
| ATOM | 284 | O | LEU | 115 | 20.374 | 8.976 | 24.762 | 1.00 | 7.36 |
| ATOM | 285 | N | LEU | 116 | 20.389 | 8.353 | 26.923 | 1.00 | 6.00 |
| ATOM | 286 | CA | LEU | 116 | 18.968 | 8.621 | 27.108 | 1.00 | 6.40 |
| ATOM | 287 | CB | LEU | 116 | 18.266 | 7.325 | 27.528 | 1.00 | 6.05 |
| ATOM | 288 | CG | LEU | 116 | 18.557 | 6.068 | 26.702 | 1.00 | 5.86 |
| ATOM | 289 | CD1 | LEU | 116 | 17.940 | 4.851 | 27.392 | 1.00 | 6.33 |
| ATOM | 290 | CD2 | LEU | 116 | 17.991 | 6.231 | 25.304 | 1.00 | 6.19 |
| ATOM | 291 | C | LEU | 116 | 18.663 | 9.703 | 28.137 | 1.00 | 7.23 |
| ATOM | 292 | O | LEU | 116 | 19.225 | 9.710 | 29.230 | 1.00 | 8.16 |
| ATOM | 293 | N | GLU | 117 | 17.771 | 10.621 | 27.785 | 1.00 | 7.97 |
| ATOM | 294 | CA | GLU | 117 | 17.384 | 11.669 | 28.723 | 1.00 | 8.82 |
| ATOM | 295 | CB | GLU | 117 | 17.043 | 12.971 | 27.990 | 1.00 | 10.69 |
| ATOM | 296 | CG | GLU | 117 | 16.520 | 14.065 | 28.914 | 1.00 | 12.86 |
| ATOM | 297 | CD | GLU | 117 | 16.478 | 15.433 | 28.258 | 1.00 | 16.05 |
| ATOM | 298 | OE1 | GLU | 117 | 15.991 | 16.386 | 28.903 | 1.00 | 17.79 |
| ATOM | 299 | OE2 | GLU | 117 | 16.937 | 15.562 | 27.105 | 1.00 | 17.80 |
| ATOM | 300 | C | GLU | 117 | 16.164 | 11.174 | 29.490 | 1.00 | 9.20 |
| ATOM | 301 | O | GLU | 117 | 15.122 | 10.891 | 28.899 | 1.00 | 8.75 |
| ATOM | 302 | N | LEU | 118 | 16.305 | 11.045 | 30.804 | 1.00 | 8.92 |
| ATOM | 303 | CA | LEU | 118 | 15.204 | 10.592 | 31.642 | 1.00 | 9.72 |
| ATOM | 304 | CB | LEU | 118 | 15.728 | 9.722 | 32.786 | 1.00 | 11.39 |
| ATOM | 305 | CG | LEU | 118 | 16.532 | 8.480 | 32.394 | 1.00 | 12.95 |
| ATOM | 306 | CD1 | LEU | 118 | 16.853 | 7.667 | 33.643 | 1.00 | 14.11 |
| ATOM | 307 | CD2 | LEU | 118 | 15.743 | 7.643 | 31.409 | 1.00 | 14.39 |
| ATOM | 308 | C | LEU | 118 | 14.508 | 11.826 | 32.200 | 1.00 | 10.39 |
| ATOM | 309 | O | LEU | 118 | 15.103 | 12.596 | 32.955 | 1.00 | 9.73 |
| ATOM | 310 | N | SER | 119 | 13.251 | 12.024 | 31.819 | 1.00 | 10.03 |
| ATOM | 311 | CA | SER | 119 | 12.510 | 13.187 | 32.284 | 1.00 | 10.69 |
| ATOM | 312 | CB | SER | 119 | 12.014 | 14.005 | 31.091 | 1.00 | 11.30 |
| ATOM | 313 | OG | SER | 119 | 13.080 | 14.335 | 30.217 | 1.00 | 11.39 |
| ATOM | 314 | C | SER | 119 | 11.321 | 12.770 | 33.132 | 1.00 | 10.86 |
| ATOM | 315 | O | SER | 119 | 10.503 | 11.959 | 32.706 | 1.00 | 10.01 |
| ATOM | 316 | N | PRO | 120 | 11.213 | 13.315 | 34.350 | 1.00 | 11.88 |
| ATOM | 317 | CD | PRO | 120 | 12.109 | 14.265 | 35.038 | 1.00 | 12.61 |
| ATOM | 318 | CA | PRO | 120 | 10.081 | 12.950 | 35.202 | 1.00 | 12.25 |
| ATOM | 319 | CB | PRO | 120 | 10.441 | 13.581 | 36.547 | 1.00 | 13.23 |
| ATOM | 320 | CG | PRO | 120 | 11.220 | 14.799 | 36.145 | 1.00 | 14.45 |
| ATOM | 321 | C | PRO | 120 | 8.782 | 13.505 | 34.623 | 1.00 | 12.69 |
| ATOM | 322 | O | PRO | 120 | 8.730 | 14.648 | 34.166 | 1.00 | 12.96 |
| ATOM | 323 | N | VAL | 121 | 7.742 | 12.682 | 34.627 | 1.00 | 12.46 |
| ATOM | 324 | CA | VAL | 121 | 6.440 | 13.088 | 34.118 | 1.00 | 12.87 |

-continued

| | | | | | | | | | |
|---|---|---|---|---|---|---|---|---|---|
| ATOM | 325 | CB | VAL | 121 | 5.797 | 11.948 | 33.306 | 1.00 | 12.58 |
| ATOM | 326 | CG1 | VAL | 121 | 4.378 | 12.318 | 32.902 | 1.00 | 11.86 |
| ATOM | 327 | CG2 | VAL | 121 | 6.642 | 11.666 | 32.074 | 1.00 | 13.10 |
| ATOM | 328 | C | VAL | 121 | 5.586 | 13.418 | 35.332 | 1.00 | 12.84 |
| ATOM | 329 | O | VAL | 121 | 4.902 | 14.440 | 35.378 | 1.00 | 13.81 |
| ATOM | 330 | N | GLU | 122 | 5.654 | 12.532 | 36.316 | 1.00 | 12.83 |
| ATOM | 331 | CA | GLU | 122 | 4.949 | 12.667 | 37.583 | 1.00 | 12.89 |
| ATOM | 332 | CB | GLU | 122 | 3.488 | 12.222 | 37.457 | 1.00 | 13.88 |
| ATOM | 333 | CG | GLU | 122 | 3.266 | 10.931 | 36.691 | 1.00 | 15.79 |
| ATOM | 334 | CD | GLU | 122 | 1.805 | 10.506 | 36.688 | 1.00 | 17.76 |
| ATOM | 335 | OE1 | GLU | 122 | 1.385 | 9.812 | 35.741 | 1.00 | 18.31 |
| ATOM | 336 | OE2 | GLU | 122 | 1.078 | 10.856 | 37.642 | 1.00 | 19.25 |
| ATOM | 337 | C | GLU | 122 | 5.705 | 11.759 | 38.538 | 1.00 | 12.49 |
| ATOM | 338 | O | GLU | 122 | 6.672 | 11.114 | 38.135 | 1.00 | 12.27 |
| ATOM | 339 | N | ARG | 123 | 5.288 | 11.701 | 39.795 | 1.00 | 11.54 |
| ATOM | 340 | CA | ARG | 123 | 5.998 | 10.854 | 40.739 | 1.00 | 10.92 |
| ATOM | 341 | CB | ARG | 123 | 5.344 | 10.896 | 42.120 | 1.00 | 11.82 |
| ATOM | 342 | CG | ARG | 123 | 5.972 | 9.885 | 43.059 | 1.00 | 12.96 |
| ATOM | 343 | CD | ARG | 123 | 5.602 | 10.112 | 44.501 | 1.00 | 14.90 |
| ATOM | 344 | NE | ARG | 123 | 6.104 | 9.014 | 45.318 | 1.00 | 14.69 |
| ATOM | 345 | CZ | ARG | 123 | 6.118 | 9.015 | 46.644 | 1.00 | 14.66 |
| ATOM | 346 | NH1 | ARG | 123 | 5.658 | 10.067 | 47.309 | 1.00 | 15.83 |
| ATOM | 347 | NH2 | ARG | 123 | 6.579 | 7.963 | 47.302 | 1.00 | 13.18 |
| ATOM | 348 | C | ARG | 123 | 6.109 | 9.399 | 40.288 | 1.00 | 9.45 |
| ATOM | 349 | O | ARG | 123 | 5.101 | 8.744 | 40.018 | 1.00 | 9.21 |
| ATOM | 350 | N | GLY | 124 | 7.345 | 8.909 | 40.217 | 1.00 | 8.93 |
| ATOM | 351 | CA | GLY | 124 | 7.601 | 7.530 | 39.828 | 1.00 | 8.60 |
| ATOM | 352 | C | GLY | 124 | 7.471 | 7.208 | 38.349 | 1.00 | 7.77 |
| ATOM | 353 | O | GLY | 124 | 7.656 | 6.060 | 37.947 | 1.00 | 7.28 |
| ATOM | 354 | N | VAL | 125 | 7.169 | 8.215 | 37.537 | 1.00 | 7.41 |
| ATOM | 355 | CA | VAL | 125 | 6.989 | 8.018 | 36.101 | 1.00 | 7.25 |
| ATOM | 356 | CB | VAL | 125 | 5.546 | 8.377 | 35.687 | 1.00 | 6.87 |
| ATOM | 357 | CG1 | VAL | 125 | 5.339 | 8.101 | 34.212 | 1.00 | 7.15 |
| ATOM | 358 | CG2 | VAL | 125 | 4.552 | 7.585 | 36.530 | 1.00 | 7.51 |
| ATOM | 359 | C | VAL | 125 | 7.955 | 8.874 | 35.291 | 1.00 | 7.01 |
| ATOM | 360 | O | VAL | 125 | 8.153 | 10.052 | 35.593 | 1.00 | 7.46 |
| ATOM | 361 | N | VAL | 126 | 8.539 | 8.286 | 34.249 | 1.00 | 6.88 |
| ATOM | 362 | CA | VAL | 126 | 9.493 | 8.999 | 33.403 | 1.00 | 6.56 |
| ATOM | 363 | CB | VAL | 126 | 10.942 | 8.553 | 33.703 | 1.00 | 6.83 |
| ATOM | 364 | CG1 | VAL | 126 | 11.302 | 8.836 | 35.148 | 1.00 | 6.87 |
| ATOM | 365 | CG2 | VAL | 126 | 11.087 | 7.064 | 33.401 | 1.00 | 7.21 |
| ATOM | 366 | C | VAL | 126 | 9.290 | 8.760 | 31.911 | 1.00 | 6.87 |
| ATOM | 367 | O | VAL | 126 | 8.579 | 7.842 | 31.505 | 1.00 | 7.11 |
| ATOM | 368 | N | SER | 127 | 9.911 | 9.612 | 31.099 | 1.00 | 5.95 |
| ATOM | 369 | CA | SER | 127 | 9.895 | 9.432 | 29.655 | 1.00 | 6.02 |
| ATOM | 370 | CB | SER | 127 | 9.447 | 10.696 | 28.908 | 1.00 | 6.80 |
| ATOM | 371 | OG | SER | 127 | 10.344 | 11.774 | 29.083 | 1.00 | 7.48 |
| ATOM | 372 | C | SER | 127 | 11.366 | 9.130 | 29.384 | 1.00 | 6.01 |
| ATOM | 373 | O | SER | 127 | 12.243 | 9.559 | 30.143 | 1.00 | 6.11 |
| ATOM | 374 | N | ILE | 128 | 11.636 | 8.375 | 28.330 | 1.00 | 5.10 |
| ATOM | 375 | CA | ILE | 128 | 13.003 | 7.997 | 27.999 | 1.00 | 5.69 |
| ATOM | 376 | CB | ILE | 128 | 13.170 | 6.472 | 28.121 | 1.00 | 5.40 |
| ATOM | 377 | CG2 | ILE | 128 | 14.626 | 6.088 | 27.897 | 1.00 | 6.23 |
| ATOM | 378 | CG1 | ILE | 128 | 12.698 | 6.014 | 29.511 | 1.00 | 5.86 |
| ATOM | 379 | CD1 | ILE | 128 | 12.683 | 4.497 | 29.713 | 1.00 | 5.16 |
| ATOM | 380 | C | ILE | 128 | 13.268 | 8.455 | 26.572 | 1.00 | 5.76 |
| ATOM | 381 | O | ILE | 128 | 12.789 | 7.849 | 25.615 | 1.00 | 6.10 |
| ATOM | 382 | N | PHE | 129 | 14.041 | 9.530 | 26.442 | 1.00 | 5.77 |
| ATOM | 383 | CA | PHE | 129 | 14.324 | 10.126 | 25.141 | 1.00 | 6.64 |
| ATOM | 384 | CB | PHE | 129 | 14.092 | 11.638 | 25.237 | 1.00 | 7.28 |
| ATOM | 385 | CG | PHE | 129 | 14.167 | 12.355 | 23.920 | 1.00 | 7.76 |
| ATOM | 386 | CD1 | PHE | 129 | 13.172 | 12.186 | 22.965 | 1.00 | 8.17 |
| ATOM | 387 | CD2 | PHE | 129 | 15.227 | 13.214 | 23.643 | 1.00 | 8.14 |
| ATOM | 388 | CE1 | PHE | 129 | 13.227 | 12.867 | 21.752 | 1.00 | 8.24 |
| ATOM | 389 | CE2 | PHE | 129 | 15.293 | 13.897 | 22.435 | 1.00 | 8.09 |
| ATOM | 390 | CZ | PHE | 129 | 14.291 | 13.725 | 21.488 | 1.00 | 8.83 |
| ATOM | 391 | C | PHE | 129 | 15.722 | 9.859 | 24.588 | 1.00 | 7.07 |
| ATOM | 392 | O | PHE | 129 | 16.726 | 10.118 | 25.253 | 1.00 | 6.90 |
| ATOM | 393 | N | GLY | 130 | 15.773 | 9.344 | 23.363 | 1.00 | 7.82 |
| ATOM | 394 | CA | GLY | 130 | 17.048 | 9.073 | 22.720 | 1.00 | 7.44 |
| ATOM | 395 | C | GLY | 130 | 17.588 | 10.389 | 22.195 | 1.00 | 8.24 |
| ATOM | 396 | O | GLY | 130 | 17.134 | 10.892 | 21.170 | 1.00 | 7.64 |
| ATOM | 397 | N | VAL | 131 | 18.562 | 10.944 | 22.908 | 1.00 | 8.47 |
| ATOM | 398 | CA | VAL | 131 | 19.164 | 12.226 | 22.561 | 1.00 | 8.95 |
| ATOM | 399 | CB | VAL | 131 | 20.371 | 12.512 | 23.489 | 1.00 | 10.08 |
| ATOM | 400 | CG1 | VAL | 131 | 20.979 | 13.857 | 23.157 | 1.00 | 12.10 |
| ATOM | 401 | CG2 | VAL | 131 | 19.917 | 12.487 | 24.948 | 1.00 | 11.84 |
| ATOM | 402 | C | VAL | 131 | 19.606 | 12.383 | 21.107 | 1.00 | 8.99 |
| ATOM | 403 | O | VAL | 131 | 19.258 | 13.364 | 20.447 | 1.00 | 8.93 |

-continued

| | | | | | | | | |
|---|---|---|---|---|---|---|---|---|
| ATOM | 404 | N | ALA | 132 | 20.367 | 11.416 | 20.606 | 1.00 | 7.92 |
| ATOM | 405 | CA | ALA | 132 | 20.880 | 11.473 | 19.241 | 1.00 | 8.44 |
| ATOM | 406 | CB | ALA | 132 | 22.082 | 10.529 | 19.103 | 1.00 | 8.07 |
| ATOM | 407 | C | ALA | 132 | 19.864 | 11.170 | 18.142 | 1.00 | 8.83 |
| ATOM | 408 | O | ALA | 132 | 19.806 | 11.876 | 17.132 | 1.00 | 9.23 |
| ATOM | 409 | N | SER | 133 | 19.066 | 10.123 | 18.337 | 1.00 | 8.54 |
| ATOM | 410 | CA | SER | 133 | 18.076 | 9.721 | 17.341 | 1.00 | 9.10 |
| ATOM | 411 | CB | SER | 133 | 17.626 | 8.279 | 17.592 | 1.00 | 9.66 |
| ATOM | 412 | OG | SER | 133 | 16.807 | 8.212 | 18.748 | 1.00 | 12.46 |
| ATOM | 413 | C | SER | 133 | 16.850 | 10.627 | 17.356 | 1.00 | 9.35 |
| ATOM | 414 | O | SER | 133 | 16.158 | 10.761 | 16.348 | 1.00 | 8.28 |
| ATOM | 415 | N | ARG | 134 | 16.585 | 11.234 | 18.510 | 1.00 | 9.32 |
| ATOM | 416 | CA | ARG | 134 | 15.436 | 12.113 | 18.696 | 1.00 | 10.27 |
| ATOM | 417 | CB | ARG | 134 | 15.380 | 13.170 | 17.588 | 1.00 | 12.72 |
| ATOM | 418 | CG | ARG | 134 | 16.623 | 14.046 | 17.501 | 1.00 | 16.89 |
| ATOM | 419 | CD | ARG | 134 | 16.855 | 14.803 | 18.799 | 1.00 | 19.81 |
| ATOM | 420 | NE | ARG | 134 | 18.015 | 15.691 | 18.743 | 1.00 | 23.62 |
| ATOM | 421 | CZ | ARG | 134 | 18.138 | 16.699 | 17.886 | 1.00 | 24.68 |
| ATOM | 422 | NH1 | ARG | 134 | 17.172 | 16.945 | 17.012 | 1.00 | 25.92 |
| ATOM | 423 | NH2 | ARG | 134 | 19.218 | 17.471 | 17.911 | 1.00 | 25.37 |
| ATOM | 424 | C | ARG | 134 | 14.121 | 11.331 | 18.745 | 1.00 | 9.51 |
| ATOM | 425 | O | ARG | 134 | 13.077 | 11.837 | 18.339 | 1.00 | 10.33 |
| ATOM | 426 | N | PHE | 135 | 14.178 | 10.097 | 19.237 | 1.00 | 8.65 |
| ATOM | 427 | CA | PHE | 135 | 12.980 | 9.269 | 19.374 | 1.00 | 8.38 |
| ATOM | 428 | CB | PHE | 135 | 13.106 | 7.940 | 18.621 | 1.00 | 8.83 |
| ATOM | 429 | CG | PHE | 135 | 12.898 | 8.035 | 17.139 | 1.00 | 8.66 |
| ATOM | 430 | CD1 | PHE | 135 | 13.953 | 8.356 | 16.291 | 1.00 | 10.75 |
| ATOM | 431 | CD2 | PHE | 135 | 11.649 | 7.765 | 16.584 | 1.00 | 8.52 |
| ATOM | 432 | CE1 | PHE | 135 | 13.768 | 8.404 | 14.909 | 1.00 | 10.30 |
| ATOM | 433 | CE2 | PHE | 135 | 11.450 | 7.811 | 15.205 | 1.00 | 8.67 |
| ATOM | 434 | CZ | PHE | 135 | 12.512 | 8.131 | 14.366 | 1.00 | 10.46 |
| ATOM | 435 | C | PHE | 135 | 12.768 | 8.924 | 20.842 | 1.00 | 7.92 |
| ATOM | 436 | O | PHE | 135 | 13.730 | 8.669 | 21.564 | 1.00 | 7.39 |
| ATOM | 437 | N | PHE | 136 | 11.512 | 8.920 | 21.279 | 1.00 | 7.93 |
| ATOM | 438 | CA | PHE | 136 | 11.184 | 8.529 | 22.642 | 1.00 | 7.08 |
| ATOM | 439 | CB | PHE | 136 | 9.824 | 9.077 | 23.091 | 1.00 | 7.49 |
| ATOM | 440 | CG | PHE | 136 | 9.838 | 10.515 | 23.482 | 1.00 | 6.98 |
| ATOM | 441 | CD1 | PHE | 136 | 9.518 | 11.501 | 22.560 | 1.00 | 7.11 |
| ATOM | 442 | CD2 | PHE | 136 | 10.155 | 10.884 | 24.785 | 1.00 | 7.49 |
| ATOM | 443 | CE1 | PHE | 136 | 9.508 | 12.839 | 22.928 | 1.00 | 8.41 |
| ATOM | 444 | CE2 | PHE | 136 | 10.150 | 12.218 | 25.166 | 1.00 | 8.09 |
| ATOM | 445 | CZ | PHE | 136 | 9.825 | 13.200 | 24.233 | 1.00 | 7.87 |
| ATOM | 446 | C | PHE | 136 | 11.033 | 7.019 | 22.576 | 1.00 | 7.61 |
| ATOM | 447 | O | PHE | 136 | 10.617 | 6.483 | 21.548 | 1.00 | 7.88 |
| ATOM | 448 | N | VAL | 137 | 11.378 | 6.331 | 23.654 | 1.00 | 6.58 |
| ATOM | 449 | CA | VAL | 137 | 11.189 | 4.890 | 23.691 | 1.00 | 6.26 |
| ATOM | 450 | CB | VAL | 137 | 12.017 | 4.231 | 24.805 | 1.00 | 6.19 |
| ATOM | 451 | CG1 | VAL | 137 | 11.626 | 2.759 | 24.937 | 1.00 | 6.00 |
| ATOM | 452 | CG2 | VAL | 137 | 13.503 | 4.351 | 24.488 | 1.00 | 6.61 |
| ATOM | 453 | C | VAL | 137 | 9.708 | 4.749 | 24.027 | 1.00 | 6.37 |
| ATOM | 454 | O | VAL | 137 | 9.213 | 5.417 | 24.937 | 1.00 | 6.96 |
| ATOM | 455 | N | ALA | 138 | 8.997 | 3.907 | 23.286 | 1.00 | 6.10 |
| ATOM | 456 | CA | ALA | 138 | 7.568 | 3.707 | 23.522 | 1.00 | 6.34 |
| ATOM | 457 | CB | ALA | 138 | 6.750 | 4.478 | 22.479 | 1.00 | 6.40 |
| ATOM | 458 | C | ALA | 138 | 7.220 | 2.226 | 23.461 | 1.00 | 6.19 |
| ATOM | 459 | O | ALA | 138 | 7.998 | 1.418 | 22.959 | 1.00 | 5.65 |
| ATOM | 460 | N | MET | 139 | 6.053 | 1.866 | 23.984 | 1.00 | 6.77 |
| ATOM | 461 | CA | MET | 139 | 5.622 | 0.472 | 23.949 | 1.00 | 6.76 |
| ATOM | 462 | CB | MET | 139 | 5.802 | −0.193 | 25.316 | 1.00 | 7.13 |
| ATOM | 463 | CG | MET | 139 | 5.454 | −1.675 | 25.304 | 1.00 | 8.40 |
| ATOM | 464 | SD | MET | 139 | 5.687 | −2.479 | 26.897 | 1.00 | 9.30 |
| ATOM | 465 | CE | MET | 139 | 7.482 | −2.496 | 27.008 | 1.00 | 8.92 |
| ATOM | 466 | C | MET | 139 | 4.161 | 0.391 | 23.529 | 1.00 | 7.49 |
| ATOM | 467 | O | MET | 139 | 3.318 | 1.120 | 24.055 | 1.00 | 6.81 |
| ATOM | 468 | N | SER | 140 | 3.873 | −0.493 | 22.576 | 1.00 | 7.52 |
| ATOM | 469 | CA | SER | 140 | 2.515 | −0.679 | 22.068 | 1.00 | 8.67 |
| ATOM | 470 | CB | SER | 140 | 2.557 | −1.319 | 20.678 | 1.00 | 8.60 |
| ATOM | 471 | OG | SER | 140 | 2.937 | −2.684 | 20.771 | 1.00 | 7.74 |
| ATOM | 472 | C | SER | 140 | 1.696 | −1.573 | 22.996 | 1.00 | 9.77 |
| ATOM | 473 | O | SER | 140 | 2.226 | −2.148 | 23.948 | 1.00 | 9.80 |
| ATOM | 474 | N | SER | 141 | 0.407 | −1.702 | 22.701 | 1.00 | 9.71 |
| ATOM | 475 | CA | SER | 141 | −0.483 | −2.530 | 23.510 | 1.00 | 11.35 |
| ATOM | 476 | CB | SER | 141 | −1.939 | −2.307 | 23.091 | 1.00 | 11.04 |
| ATOM | 477 | OG | SER | 141 | −2.161 | −2.753 | 21.763 | 1.00 | 12.07 |
| ATOM | 478 | C | SER | 141 | −0.130 | −4.010 | 23.375 | 1.00 | 11.94 |
| ATOM | 479 | O | SER | 141 | −0.628 | −4.848 | 24.131 | 1.00 | 12.36 |
| ATOM | 480 | N | LYS | 142 | 0.724 | −4.327 | 22.406 | 1.00 | 12.31 |
| ATOM | 481 | CA | LYS | 142 | 1.150 | −5.705 | 22.186 | 1.00 | 13.17 |
| ATOM | 482 | CB | LYS | 142 | 1.258 | −6.005 | 20.690 | 1.00 | 15.47 |

-continued

| | | | | | | | | |
|---|---|---|---|---|---|---|---|---|
| ATOM | 483 | CG | LYS | 142 | −0.063 | −5.947 | 19.946 | 1.00 | 18.63 |
| ATOM | 484 | CD | LYS | 142 | 0.144 | −6.189 | 18.463 | 1.00 | 21.02 |
| ATOM | 485 | CE | LYS | 142 | −1.155 | −6.052 | 17.690 | 1.00 | 23.01 |
| ATOM | 486 | NZ | LYS | 142 | −0.927 | −6.222 | 16.228 | 1.00 | 24.37 |
| ATOM | 487 | C | LYS | 142 | 2.498 | −5.950 | 22.849 | 1.00 | 12.17 |
| ATOM | 488 | O | LYS | 142 | 3.071 | −7.027 | 22.717 | 1.00 | 12.32 |
| ATOM | 489 | N | GLY | 143 | 3.000 | −4.936 | 23.550 | 1.00 | 10.43 |
| ATOM | 490 | CA | GLY | 143 | 4.270 | −5.061 | 24.245 | 1.00 | 9.42 |
| ATOM | 491 | C | GLY | 143 | 5.506 | −4.804 | 23.404 | 1.00 | 8.75 |
| ATOM | 492 | O | GLY | 143 | 6.626 | −5.029 | 23.862 | 1.00 | 8.31 |
| ATOM | 493 | N | LYS | 144 | 5.314 | −4.321 | 22.181 | 1.00 | 7.56 |
| ATOM | 494 | CA | LYS | 144 | 6.437 | −4.054 | 21.293 | 1.00 | 6.96 |
| ATOM | 495 | CB | LYS | 144 | 5.988 | −4.152 | 19.833 | 1.00 | 7.62 |
| ATOM | 496 | CG | LYS | 144 | 7.102 | −3.928 | 18.815 | 1.00 | 8.80 |
| ATOM | 497 | CD | LYS | 144 | 8.145 | −5.037 | 18.867 | 1.00 | 8.64 |
| ATOM | 498 | CE | LYS | 144 | 9.230 | −4.827 | 17.819 | 1.00 | 9.66 |
| ATOM | 499 | NZ | LYS | 144 | 10.256 | −5.911 | 17.843 | 1.00 | 11.27 |
| ATOM | 500 | C | LYS | 144 | 7.067 | −2.687 | 21.527 | 1.00 | 6.78 |
| ATOM | 501 | O | LYS | 144 | 6.392 | −1.657 | 21.454 | 1.00 | 6.18 |
| ATOM | 502 | N | LEU | 145 | 8.365 | −2.680 | 21.813 | 1.00 | 6.40 |
| ATOM | 503 | CA | LEU | 145 | 9.088 | −1.428 | 22.014 | 1.00 | 6.12 |
| ATOM | 504 | CB | LEU | 145 | 10.437 | −1.687 | 22.689 | 1.00 | 5.82 |
| ATOM | 505 | CG | LEU | 145 | 10.411 | −1.994 | 24.186 | 1.00 | 6.37 |
| ATOM | 506 | CD1 | LEU | 145 | 11.800 | −2.423 | 24.650 | 1.00 | 7.01 |
| ATOM | 507 | CD2 | LEU | 145 | 9.949 | −0.756 | 24.944 | 1.00 | 7.23 |
| ATOM | 508 | C | LEU | 145 | 9.323 | −0.795 | 20.646 | 1.00 | 6.17 |
| ATOM | 509 | O | LEU | 145 | 9.697 | −1.483 | 19.695 | 1.00 | 6.13 |
| ATOM | 510 | N | TYR | 146 | 9.095 | 0.509 | 20.544 | 1.00 | 5.68 |
| ATOM | 511 | CA | TYR | 146 | 9.300 | 1.206 | 19.282 | 1.00 | 6.42 |
| ATOM | 512 | CB | TYR | 146 | 8.049 | 1.078 | 18.395 | 1.00 | 6.42 |
| ATOM | 513 | CG | TYR | 146 | 6.860 | 1.917 | 18.824 | 1.00 | 6.55 |
| ATOM | 514 | CD1 | TYR | 146 | 6.665 | 3.197 | 18.304 | 1.00 | 6.78 |
| ATOM | 515 | CE1 | TYR | 146 | 5.585 | 3.982 | 18.707 | 1.00 | 7.64 |
| ATOM | 516 | CD2 | TYR | 146 | 5.943 | 1.438 | 19.758 | 1.00 | 7.13 |
| ATOM | 517 | CE2 | TYR | 146 | 4.857 | 2.218 | 20.169 | 1.00 | 7.09 |
| ATOM | 518 | CZ | TYR | 146 | 4.687 | 3.487 | 19.640 | 1.00 | 7.80 |
| ATOM | 519 | OH | TYR | 146 | 3.627 | 4.269 | 20.044 | 1.00 | 7.00 |
| ATOM | 520 | C | TYR | 146 | 9.643 | 2.672 | 19.536 | 1.00 | 6.69 |
| ATOM | 521 | O | TYR | 146 | 9.400 | 3.201 | 20.625 | 1.00 | 6.62 |
| ATOM | 522 | N | GLY | 147 | 10.232 | 3.320 | 18.538 | 1.00 | 5.95 |
| ATOM | 523 | CA | GLY | 147 | 10.593 | 4.715 | 18.692 | 1.00 | 5.63 |
| ATOM | 524 | C | GLY | 147 | 9.469 | 5.638 | 18.268 | 1.00 | 5.37 |
| ATOM | 525 | O | GLY | 147 | 8.886 | 5.458 | 17.194 | 1.00 | 5.41 |
| ATOM | 526 | N | SER | 148 | 9.159 | 6.621 | 19.108 | 1.00 | 5.18 |
| ATOM | 527 | CA | SER | 148 | 8.104 | 7.588 | 18.810 | 1.00 | 5.87 |
| ATOM | 528 | CB | SER | 148 | 7.063 | 7.610 | 19.934 | 1.00 | 6.82 |
| ATOM | 529 | OG | SER | 148 | 5.963 | 8.438 | 19.586 | 1.00 | 5.87 |
| ATOM | 530 | C | SER | 148 | 8.744 | 8.965 | 18.662 | 1.00 | 6.42 |
| ATOM | 531 | O | SER | 148 | 9.319 | 9.496 | 19.612 | 1.00 | 7.70 |
| ATOM | 532 | N | PRO | 149 | 8.652 | 9.561 | 17.462 | 1.00 | 7.74 |
| ATOM | 533 | CD | PRO | 149 | 7.983 | 9.012 | 16.268 | 1.00 | 7.72 |
| ATOM | 534 | CA | PRO | 149 | 9.228 | 10.880 | 17.182 | 1.00 | 8.21 |
| ATOM | 535 | CB | PRO | 149 | 9.112 | 10.988 | 15.662 | 1.00 | 8.68 |
| ATOM | 536 | CG | PRO | 149 | 7.866 | 10.227 | 15.368 | 1.00 | 9.11 |
| ATOM | 537 | C | PRO | 149 | 8.561 | 12.038 | 17.924 | 1.00 | 8.51 |
| ATOM | 538 | O | PRO | 149 | 9.101 | 13.147 | 17.965 | 1.00 | 8.97 |
| ATOM | 539 | N | PHE | 150 | 7.385 | 11.782 | 18.493 | 1.00 | 8.22 |
| ATOM | 540 | CA | PHE | 150 | 6.674 | 12.791 | 19.274 | 1.00 | 8.18 |
| ATOM | 541 | CB | PHE | 150 | 5.525 | 13.429 | 18.466 | 1.00 | 9.01 |
| ATOM | 542 | CG | PHE | 150 | 4.593 | 12.444 | 17.820 | 1.00 | 10.81 |
| ATOM | 543 | CD1 | PHE | 150 | 3.496 | 11.943 | 18.513 | 1.00 | 11.41 |
| ATOM | 544 | CD2 | PHE | 150 | 4.798 | 12.037 | 16.506 | 1.00 | 11.41 |
| ATOM | 545 | CE1 | PHE | 150 | 2.610 | 11.049 | 17.903 | 1.00 | 12.19 |
| ATOM | 546 | CE2 | PHE | 150 | 3.922 | 11.144 | 15.886 | 1.00 | 12.69 |
| ATOM | 547 | CZ | PHE | 150 | 2.824 | 10.650 | 16.588 | 1.00 | 12.71 |
| ATOM | 548 | C | PHE | 150 | 6.173 | 12.145 | 20.567 | 1.00 | 7.43 |
| ATOM | 549 | O | PHE | 150 | 5.993 | 10.928 | 20.636 | 1.00 | 6.84 |
| ATOM | 550 | N | PHE | 151 | 5.967 | 12.965 | 21.593 | 1.00 | 6.95 |
| ATOM | 551 | CA | PHE | 151 | 5.550 | 12.482 | 22.908 | 1.00 | 7.33 |
| ATOM | 552 | CB | PHE | 151 | 5.862 | 13.567 | 23.945 | 1.00 | 8.43 |
| ATOM | 553 | CG | PHE | 151 | 5.952 | 13.062 | 25.355 | 1.00 | 8.59 |
| ATOM | 554 | CD1 | PHE | 151 | 6.480 | 11.802 | 25.631 | 1.00 | 8.15 |
| ATOM | 555 | CD2 | PHE | 151 | 5.558 | 13.870 | 26.418 | 1.00 | 10.06 |
| ATOM | 556 | CE1 | PHE | 151 | 6.614 | 11.356 | 26.943 | 1.00 | 8.82 |
| ATOM | 557 | CE2 | PHE | 151 | 5.690 | 13.433 | 27.738 | 1.00 | 9.79 |
| ATOM | 558 | CZ | PHE | 151 | 6.219 | 12.174 | 28.000 | 1.00 | 10.29 |
| ATOM | 559 | C | PHE | 151 | 4.086 | 12.059 | 22.994 | 1.00 | 7.03 |
| ATOM | 560 | O | PHE | 151 | 3.192 | 12.832 | 22.657 | 1.00 | 6.91 |
| ATOM | 561 | N | THR | 152 | 3.852 | 10.827 | 23.450 | 1.00 | 7.20 |

-continued

| | | | | | | | | |
|---|---|---|---|---|---|---|---|---|
| ATOM | 562 | CA | THR | 152 | 2.495 | 10.286 | 23.581 | 1.00 | 6.32 |
| ATOM | 563 | CB | THR | 152 | 2.152 | 9.316 | 22.443 | 1.00 | 6.44 |
| ATOM | 564 | OG1 | THR | 152 | 2.906 | 8.110 | 22.615 | 1.00 | 5.93 |
| ATOM | 565 | CG2 | THR | 152 | 2.470 | 9.933 | 21.090 | 1.00 | 7.16 |
| ATOM | 566 | C | THR | 152 | 2.321 | 9.499 | 24.872 | 1.00 | 6.73 |
| ATOM | 567 | O | THR | 152 | 3.273 | 9.306 | 25.629 | 1.00 | 6.29 |
| ATOM | 568 | N | ASP | 153 | 1.102 | 9.013 | 25.097 | 1.00 | 7.13 |
| ATOM | 569 | CA | ASP | 153 | 0.801 | 8.240 | 26.292 | 1.00 | 7.68 |
| ATOM | 570 | CB | ASP | 153 | −0.720 | 8.176 | 26.521 | 1.00 | 8.99 |
| ATOM | 571 | CG | ASP | 153 | −1.477 | 7.518 | 25.379 | 1.00 | 9.77 |
| ATOM | 572 | OD1 | ASP | 153 | −0.949 | 7.437 | 24.252 | 1.00 | 9.30 |
| ATOM | 573 | OD2 | ASP | 153 | −2.631 | 7.095 | 25.614 | 1.00 | 10.99 |
| ATOM | 574 | C | ASP | 153 | 1.424 | 6.837 | 26.297 | 1.00 | 7.99 |
| ATOM | 575 | O | ASP | 153 | 1.304 | 6.110 | 27.282 | 1.00 | 8.34 |
| ATOM | 576 | N | GLU | 154 | 2.092 | 6.458 | 25.208 | 1.00 | 7.55 |
| ATOM | 577 | CA | GLU | 154 | 2.763 | 5.157 | 25.157 | 1.00 | 6.93 |
| ATOM | 578 | CB | GLU | 154 | 2.537 | 4.456 | 23.806 | 1.00 | 7.67 |
| ATOM | 579 | CG | GLU | 154 | 1.090 | 4.029 | 23.552 | 1.00 | 7.08 |
| ATOM | 580 | CD | GLU | 154 | 0.944 | 3.048 | 22.395 | 1.00 | 7.82 |
| ATOM | 581 | OE1 | GLU | 154 | 1.765 | 3.091 | 21.456 | 1.00 | 6.93 |
| ATOM | 582 | OE2 | GLU | 154 | −0.010 | 2.237 | 22.417 | 1.00 | 7.76 |
| ATOM | 583 | C | GLU | 154 | 4.265 | 5.353 | 25.395 | 1.00 | 6.91 |
| ATOM | 584 | O | GLU | 154 | 5.048 | 4.409 | 25.276 | 1.00 | 6.34 |
| ATOM | 585 | N | CYS | 155 | 4.653 | 6.579 | 25.746 | 1.00 | 6.29 |
| ATOM | 586 | CA | CYS | 155 | 6.055 | 6.918 | 26.003 | 1.00 | 6.66 |
| ATOM | 587 | CB | CYS | 155 | 6.426 | 8.221 | 25.292 | 1.00 | 6.30 |
| ATOM | 588 | SG | CYS | 155 | 6.252 | 8.217 | 23.510 | 1.00 | 7.00 |
| ATOM | 589 | C | CYS | 155 | 6.352 | 7.099 | 27.492 | 1.00 | 7.01 |
| ATOM | 590 | O | CYS | 155 | 7.441 | 7.538 | 27.863 | 1.00 | 8.21 |
| ATOM | 591 | N | THR | 156 | 5.386 | 6.775 | 28.340 | 1.00 | 6.69 |
| ATOM | 592 | CA | THR | 156 | 5.560 | 6.931 | 29.780 | 1.00 | 5.87 |
| ATOM | 593 | CB | THR | 156 | 4.348 | 7.646 | 30.391 | 1.00 | 5.85 |
| ATOM | 594 | OG1 | THR | 156 | 3.146 | 7.045 | 29.903 | 1.00 | 6.18 |
| ATOM | 595 | CG2 | THR | 156 | 4.360 | 9.118 | 30.010 | 1.00 | 6.61 |
| ATOM | 596 | C | THR | 156 | 5.763 | 5.589 | 30.467 | 1.00 | 5.83 |
| ATOM | 597 | O | THR | 156 | 5.073 | 4.615 | 30.167 | 1.00 | 5.54 |
| ATOM | 598 | N | PHE | 157 | 6.710 | 5.553 | 31.401 | 1.00 | 5.70 |
| ATOM | 599 | CA | PHE | 157 | 7.043 | 4.327 | 32.113 | 1.00 | 5.65 |
| ATOM | 600 | CB | PHE | 157 | 8.341 | 3.739 | 31.545 | 1.00 | 6.27 |
| ATOM | 601 | CG | PHE | 157 | 8.240 | 3.314 | 30.111 | 1.00 | 5.92 |
| ATOM | 602 | CD1 | PHE | 157 | 7.775 | 2.046 | 29.779 | 1.00 | 6.03 |
| ATOM | 603 | CD2 | PHE | 157 | 8.582 | 4.192 | 29.089 | 1.00 | 5.50 |
| ATOM | 604 | CE1 | PHE | 157 | 7.650 | 1.658 | 28.445 | 1.00 | 6.23 |
| ATOM | 605 | CE2 | PHE | 157 | 8.459 | 3.814 | 27.758 | 1.00 | 5.35 |
| ATOM | 606 | CZ | PHE | 157 | 7.992 | 2.543 | 27.437 | 1.00 | 5.57 |
| ATOM | 607 | C | PHE | 157 | 7.244 | 4.545 | 33.604 | 1.00 | 6.10 |
| ATOM | 608 | O | PHE | 157 | 7.811 | 5.553 | 34.021 | 1.00 | 5.75 |
| ATOM | 609 | N | LYS | 158 | 6.784 | 3.590 | 34.403 | 1.00 | 6.36 |
| ATOM | 610 | CA | LYS | 158 | 6.976 | 3.661 | 35.843 | 1.00 | 6.76 |
| ATOM | 611 | CB | LYS | 158 | 5.964 | 2.772 | 36.567 | 1.00 | 7.54 |
| ATOM | 612 | CG | LYS | 158 | 4.531 | 3.239 | 36.431 | 1.00 | 8.41 |
| ATOM | 613 | CD | LYS | 158 | 3.599 | 2.436 | 37.322 | 1.00 | 10.05 |
| ATOM | 614 | CE | LYS | 158 | 2.186 | 2.986 | 37.247 | 1.00 | 11.40 |
| ATOM | 615 | NZ | LYS | 158 | 1.286 | 2.332 | 38.237 | 1.00 | 12.48 |
| ATOM | 616 | C | LYS | 158 | 8.389 | 3.153 | 36.111 | 1.00 | 6.88 |
| ATOM | 617 | O | LYS | 158 | 8.743 | 2.048 | 35.698 | 1.00 | 7.51 |
| ATOM | 618 | N | GLU | 159 | 9.195 | 3.966 | 36.785 | 1.00 | 6.50 |
| ATOM | 619 | CA | GLU | 159 | 10.568 | 3.598 | 37.117 | 1.00 | 7.08 |
| ATOM | 620 | CB | GLU | 159 | 11.446 | 4.847 | 37.124 | 1.00 | 8.45 |
| ATOM | 621 | CG | GLU | 159 | 12.930 | 4.578 | 37.312 | 1.00 | 10.72 |
| ATOM | 622 | CD | GLU | 159 | 13.754 | 5.830 | 37.101 | 1.00 | 12.99 |
| ATOM | 623 | OE1 | GLU | 159 | 13.516 | 6.820 | 37.823 | 1.00 | 14.61 |
| ATOM | 624 | OE2 | GLU | 159 | 14.632 | 5.829 | 36.212 | 1.00 | 14.45 |
| ATOM | 625 | C | GLU | 159 | 10.535 | 2.954 | 38.498 | 1.00 | 7.00 |
| ATOM | 626 | O | GLU | 159 | 10.389 | 3.639 | 39.515 | 1.00 | 6.45 |
| ATOM | 627 | N | ILE | 160 | 10.679 | 1.632 | 38.521 | 1.00 | 6.44 |
| ATOM | 628 | CA | ILE | 160 | 10.602 | 0.850 | 39.749 | 1.00 | 6.73 |
| ATOM | 629 | CB | ILE | 160 | 9.649 | −0.348 | 39.534 | 1.00 | 7.25 |
| ATOM | 630 | CG2 | ILE | 160 | 9.493 | −1.142 | 40.827 | 1.00 | 8.05 |
| ATOM | 631 | CG1 | ILE | 160 | 8.292 | 0.169 | 39.047 | 1.00 | 7.90 |
| ATOM | 632 | CD1 | ILE | 160 | 7.370 | −0.906 | 38.490 | 1.00 | 8.51 |
| ATOM | 633 | C | ILE | 160 | 11.946 | 0.336 | 40.245 | 1.00 | 7.21 |
| ATOM | 634 | O | ILE | 160 | 12.623 | −0.426 | 39.553 | 1.00 | 6.33 |
| ATOM | 635 | N | LEU | 161 | 12.307 | 0.742 | 41.461 | 1.00 | 6.48 |
| ATOM | 636 | CA | LEU | 161 | 13.570 | 0.337 | 42.065 | 1.00 | 6.42 |
| ATOM | 637 | CB | LEU | 161 | 13.820 | 1.115 | 43.362 | 1.00 | 6.84 |
| ATOM | 638 | CG | LEU | 161 | 15.159 | 0.811 | 44.047 | 1.00 | 6.63 |
| ATOM | 639 | CD1 | LEU | 161 | 16.301 | 1.238 | 43.135 | 1.00 | 7.13 |
| ATOM | 640 | CD2 | LEU | 161 | 15.247 | 1.538 | 45.382 | 1.00 | 7.21 |

-continued

| | | | | | | | | | |
|---|---|---|---|---|---|---|---|---|---|
| ATOM | 641 | C | LEU | 161 | 13.618 | −1.154 | 42.363 | 1.00 | 7.01 |
| ATOM | 642 | O | LEU | 161 | 12.632 | −1.745 | 42.816 | 1.00 | 5.88 |
| ATOM | 643 | N | LEU | 162 | 14.785 | −1.741 | 42.110 | 1.00 | 6.67 |
| ATOM | 644 | CA | LEU | 162 | 15.044 | −3.160 | 42.333 | 1.00 | 7.48 |
| ATOM | 645 | CB | LEU | 162 | 15.362 | −3.843 | 41.000 | 1.00 | 7.02 |
| ATOM | 646 | CG | LEU | 162 | 14.313 | −3.734 | 39.893 | 1.00 | 7.49 |
| ATOM | 647 | CD1 | LEU | 162 | 14.921 | −4.162 | 38.563 | 1.00 | 7.87 |
| ATOM | 648 | CD2 | LEU | 162 | 13.112 | −4.591 | 40.254 | 1.00 | 8.37 |
| ATOM | 649 | C | LEU | 162 | 16.264 | −3.270 | 43.243 | 1.00 | 7.49 |
| ATOM | 650 | O | LEU | 162 | 16.890 | −2.264 | 43.570 | 1.00 | 7.10 |
| ATOM | 651 | N | PRO | 163 | 16.610 | −4.493 | 43.677 | 1.00 | 8.02 |
| ATOM | 652 | CD | PRO | 163 | 15.853 | −5.756 | 43.606 | 1.00 | 8.20 |
| ATOM | 653 | CA | PRO | 163 | 17.785 | −4.635 | 44.542 | 1.00 | 8.81 |
| ATOM | 654 | CB | PRO | 163 | 17.822 | −6.135 | 44.827 | 1.00 | 9.08 |
| ATOM | 655 | CG | PRO | 163 | 16.371 | −6.514 | 44.808 | 1.00 | 8.96 |
| ATOM | 656 | C | PRO | 163 | 19.032 | −4.175 | 43.784 | 1.00 | 9.09 |
| ATOM | 657 | O | PRO | 163 | 19.061 | −4.205 | 42.554 | 1.00 | 8.86 |
| ATOM | 658 | N | ASN | 164 | 20.049 | −3.743 | 44.522 | 1.00 | 9.58 |
| ATOM | 659 | CA | ASN | 164 | 21.314 | −3.303 | 43.936 | 1.00 | 10.43 |
| ATOM | 660 | CB | ASN | 164 | 22.031 | −4.499 | 43.304 | 1.00 | 11.05 |
| ATOM | 661 | CG | ASN | 164 | 22.486 | −5.518 | 44.338 | 1.00 | 12.27 |
| ATOM | 662 | OD1 | ASN | 164 | 22.849 | −6.647 | 43.999 | 1.00 | 13.69 |
| ATOM | 663 | ND2 | ASN | 164 | 22.478 | −5.119 | 45.605 | 1.00 | 10.90 |
| ATOM | 664 | C | ASN | 164 | 21.246 | −2.144 | 42.935 | 1.00 | 10.78 |
| ATOM | 665 | O | ASN | 164 | 22.006 | −2.098 | 41.965 | 1.00 | 11.04 |
| ATOM | 666 | N | ASN | 165 | 20.332 | −1.215 | 43.193 | 1.00 | 10.80 |
| ATOM | 667 | CA | ASN | 165 | 20.148 | −0.009 | 42.390 | 1.00 | 11.74 |
| ATOM | 668 | CB | ASN | 165 | 21.426 | 0.836 | 42.423 | 1.00 | 14.07 |
| ATOM | 669 | CG | ASN | 165 | 21.142 | 2.328 | 42.341 | 1.00 | 17.00 |
| ATOM | 670 | OD1 | ASN | 165 | 20.431 | 2.884 | 43.187 | 1.00 | 17.76 |
| ATOM | 671 | ND2 | ASN | 165 | 21.691 | 2.983 | 41.322 | 1.00 | 18.46 |
| ATOM | 672 | C | ASN | 165 | 19.686 | −0.178 | 40.944 | 1.00 | 10.73 |
| ATOM | 673 | O | ASN | 165 | 19.738 | 0.769 | 40.162 | 1.00 | 11.09 |
| ATOM | 674 | N | TYR | 166 | 19.245 | −1.375 | 40.575 | 1.00 | 9.88 |
| ATOM | 675 | CA | TYR | 166 | 18.737 | −1.586 | 39.221 | 1.00 | 9.07 |
| ATOM | 676 | CB | TYR | 166 | 18.721 | −3.073 | 38.862 | 1.00 | 9.58 |
| ATOM | 677 | CG | TYR | 166 | 20.043 | −3.623 | 38.390 | 1.00 | 11.15 |
| ATOM | 678 | CD1 | TYR | 166 | 20.312 | −3.767 | 37.028 | 1.00 | 11.97 |
| ATOM | 679 | CE1 | TYR | 166 | 21.533 | −4.271 | 36.582 | 1.00 | 13.55 |
| ATOM | 680 | CD2 | TYR | 166 | 21.032 | −3.991 | 39.300 | 1.00 | 13.15 |
| ATOM | 681 | CE2 | TYR | 166 | 22.257 | −4.493 | 38.866 | 1.00 | 14.56 |
| ATOM | 682 | CZ | TYR | 166 | 22.499 | −4.630 | 37.506 | 1.00 | 14.88 |
| ATOM | 683 | OH | TYR | 166 | 23.707 | −5.134 | 37.068 | 1.00 | 16.64 |
| ATOM | 684 | C | TYR | 166 | 17.302 | −1.076 | 39.218 | 1.00 | 8.86 |
| ATOM | 685 | O | TYR | 166 | 16.690 | −0.947 | 40.277 | 1.00 | 9.39 |
| ATOM | 686 | N | ASN | 167 | 16.772 | −0.790 | 38.032 | 1.00 | 7.93 |
| ATOM | 687 | CA | ASN | 167 | 15.396 | −0.332 | 37.895 | 1.00 | 8.47 |
| ATOM | 688 | CB | ASN | 167 | 15.332 | 1.143 | 37.480 | 1.00 | 9.78 |
| ATOM | 689 | CG | ASN | 167 | 15.806 | 2.084 | 38.561 | 1.00 | 11.84 |
| ATOM | 690 | OD1 | ASN | 167 | 15.313 | 2.055 | 39.687 | 1.00 | 13.23 |
| ATOM | 691 | ND2 | ASN | 167 | 16.760 | 2.939 | 38.218 | 1.00 | 13.91 |
| ATOM | 692 | C | ASN | 167 | 14.688 | −1.136 | 36.818 | 1.00 | 7.74 |
| ATOM | 693 | O | ASN | 167 | 15.313 | −1.607 | 35.863 | 1.00 | 8.53 |
| ATOM | 694 | N | ALA | 168 | 13.381 | −1.302 | 36.989 | 1.00 | 7.42 |
| ATOM | 695 | CA | ALA | 168 | 12.559 | −1.972 | 35.995 | 1.00 | 5.36 |
| ATOM | 696 | CB | ALA | 168 | 11.664 | −3.014 | 36.640 | 1.00 | 5.62 |
| ATOM | 697 | C | ALA | 168 | 11.720 | −0.827 | 35.451 | 1.00 | 5.33 |
| ATOM | 698 | O | ALA | 168 | 11.470 | 0.155 | 36.158 | 1.00 | 5.24 |
| ATOM | 699 | N | TYR | 169 | 11.299 | −0.939 | 34.199 | 1.00 | 4.83 |
| ATOM | 700 | CA | TYR | 169 | 10.485 | 0.100 | 33.583 | 1.00 | 5.05 |
| ATOM | 701 | CB | TYR | 169 | 11.270 | 0.770 | 32.453 | 1.00 | 5.13 |
| ATOM | 702 | CG | TYR | 169 | 12.432 | 1.583 | 32.983 | 1.00 | 5.77 |
| ATOM | 703 | CD1 | TYR | 169 | 12.254 | 2.900 | 33.403 | 1.00 | 6.00 |
| ATOM | 704 | CE1 | TYR | 169 | 13.295 | 3.617 | 33.994 | 1.00 | 6.57 |
| ATOM | 705 | CD2 | TYR | 169 | 13.686 | 1.001 | 33.157 | 1.00 | 5.97 |
| ATOM | 706 | CE2 | TYR | 169 | 14.733 | 1.706 | 33.745 | 1.00 | 6.85 |
| ATOM | 707 | CZ | TYR | 169 | 14.533 | 3.009 | 34.164 | 1.00 | 7.84 |
| ATOM | 708 | OH | TYR | 169 | 15.568 | 3.690 | 34.774 | 1.00 | 8.35 |
| ATOM | 709 | C | TYR | 169 | 9.200 | −0.524 | 33.071 | 1.00 | 5.40 |
| ATOM | 710 | O | TYR | 169 | 9.207 | −1.297 | 32.114 | 1.00 | 5.61 |
| ATOM | 711 | N | GLU | 170 | 8.095 | −0.185 | 33.723 | 1.00 | 5.44 |
| ATOM | 712 | CA | GLU | 170 | 6.794 | −0.733 | 33.362 | 1.00 | 6.45 |
| ATOM | 713 | CB | GLU | 170 | 6.052 | −1.154 | 34.635 | 1.00 | 7.61 |
| ATOM | 714 | CG | GLU | 170 | 4.608 | −1.600 | 34.426 | 1.00 | 7.81 |
| ATOM | 715 | CD | GLU | 170 | 3.905 | −1.897 | 35.740 | 1.00 | 8.83 |
| ATOM | 716 | OE1 | GLU | 170 | 4.305 | −1.316 | 36.772 | 1.00 | 9.65 |
| ATOM | 717 | OE2 | GLU | 170 | 2.947 | −2.698 | 35.742 | 1.00 | 9.00 |
| ATOM | 718 | C | GLU | 170 | 5.947 | 0.255 | 32.574 | 1.00 | 6.80 |
| ATOM | 719 | O | GLU | 170 | 5.883 | 1.441 | 32.906 | 1.00 | 6.00 |

-continued

| | | | | | | | | |
|---|---|---|---|---|---|---|---|---|
| ATOM | 720 | N | SER | 171 | 5.304 | −0.235 | 31.521 | 1.00 | 6.67 |
| ATOM | 721 | CA | SER | 171 | 4.445 | 0.615 | 30.709 | 1.00 | 7.04 |
| ATOM | 722 | CB | SER | 171 | 3.755 | −0.201 | 29.615 | 1.00 | 6.44 |
| ATOM | 723 | CG | SER | 171 | 2.748 | 0.577 | 28.982 | 1.00 | 8.08 |
| ATOM | 724 | C | SER | 171 | 3.380 | 1.241 | 31.593 | 1.00 | 7.11 |
| ATOM | 725 | O | SER | 171 | 2.683 | 0.541 | 32.330 | 1.00 | 7.84 |
| ATOM | 726 | N | TYR | 172 | 3.247 | 2.560 | 31.516 | 1.00 | 7.12 |
| ATOM | 727 | CA | TYR | 172 | 2.246 | 3.243 | 32.314 | 1.00 | 8.72 |
| ATOM | 728 | CB | TYR | 172 | 2.507 | 4.748 | 32.327 | 1.00 | 9.00 |
| ATOM | 729 | CG | TYR | 172 | 1.543 | 5.499 | 33.207 | 1.00 | 11.05 |
| ATOM | 730 | CD1 | TYR | 172 | 1.765 | 5.613 | 34.578 | 1.00 | 11.87 |
| ATOM | 731 | CE1 | TYR | 172 | 0.849 | 6.260 | 35.403 | 1.00 | 13.42 |
| ATOM | 732 | CD2 | TYR | 172 | 0.378 | 6.050 | 32.678 | 1.00 | 12.30 |
| ATOM | 733 | CE2 | TYR | 172 | −0.543 | 6.695 | 33.492 | 1.00 | 14.29 |
| ATOM | 734 | CZ | TYR | 172 | −0.303 | 6.797 | 34.850 | 1.00 | 14.57 |
| ATOM | 735 | OH | TYR | 172 | −1.220 | 7.438 | 35.652 | 1.00 | 17.42 |
| ATOM | 736 | C | TYR | 172 | 0.855 | 2.969 | 31.738 | 1.00 | 8.33 |
| ATOM | 737 | O | TYR | 172 | −0.103 | 2.751 | 32.477 | 1.00 | 8.14 |
| ATOM | 738 | N | LYS | 173 | 0.748 | 2.975 | 30.414 | 1.00 | 8.55 |
| ATOM | 739 | CA | LYS | 173 | −0.536 | 2.734 | 29.764 | 1.00 | 8.99 |
| ATOM | 740 | CB | LYS | 173 | −0.496 | 3.209 | 28.306 | 1.00 | 9.71 |
| ATOM | 741 | CG | LYS | 173 | −1.848 | 3.137 | 27.605 | 1.00 | 10.52 |
| ATOM | 742 | CD | LYS | 173 | −1.861 | 3.932 | 26.300 | 1.00 | 10.91 |
| ATOM | 743 | CE | LYS | 173 | −3.273 | 4.008 | 25.727 | 1.00 | 11.42 |
| ATOM | 744 | NZ | LYS | 173 | −3.348 | 4.800 | 24.469 | 1.00 | 11.20 |
| ATOM | 745 | C | LYS | 173 | −0.977 | 1.273 | 29.808 | 1.00 | 8.99 |
| ATOM | 746 | O | LYS | 173 | −2.177 | 0.985 | 29.849 | 1.00 | 7.88 |
| ATOM | 747 | N | TYR | 174 | −0.012 | 0.355 | 29.797 | 1.00 | 8.58 |
| ATOM | 748 | CA | TYR | 174 | −0.302 | −1.080 | 29.818 | 1.00 | 9.01 |
| ATOM | 749 | CB | TYR | 174 | 0.170 | −1.724 | 28.510 | 1.00 | 8.57 |
| ATOM | 750 | CG | TYR | 174 | −0.329 | −0.998 | 27.285 | 1.00 | 8.58 |
| ATOM | 751 | CD1 | TYR | 174 | −1.691 | −0.947 | 26.988 | 1.00 | 7.77 |
| ATOM | 752 | CE1 | TYR | 174 | −2.162 | −0.224 | 25.894 | 1.00 | 7.99 |
| ATOM | 753 | CD2 | TYR | 174 | 0.555 | −0.314 | 26.450 | 1.00 | 7.31 |
| ATOM | 754 | CE2 | TYR | 174 | 0.095 | 0.411 | 25.354 | 1.00 | 7.84 |
| ATOM | 755 | CZ | TYR | 174 | −1.263 | 0.454 | 25.083 | 1.00 | 7.62 |
| ATOM | 756 | OH | TYR | 174 | −1.721 | 1.185 | 24.014 | 1.00 | 7.92 |
| ATOM | 757 | C | TYR | 174 | 0.374 | −1.771 | 31.002 | 1.00 | 9.15 |
| ATOM | 758 | O | TYR | 174 | 1.466 | −2.332 | 30.873 | 1.00 | 8.77 |
| ATOM | 759 | N | PRO | 175 | −0.277 | −1.742 | 32.176 | 1.00 | 9.16 |
| ATOM | 760 | CD | PRO | 175 | −1.589 | −1.129 | 32.440 | 1.00 | 9.90 |
| ATOM | 761 | CA | PRO | 175 | 0.256 | −2.361 | 33.391 | 1.00 | 9.10 |
| ATOM | 762 | CB | PRO | 175 | −0.905 | −2.227 | 34.375 | 1.00 | 10.40 |
| ATOM | 763 | CG | PRO | 175 | −1.566 | −0.966 | 33.941 | 1.00 | 10.31 |
| ATOM | 764 | C | PRO | 175 | 0.663 | −3.813 | 33.180 | 1.00 | 9.23 |
| ATOM | 765 | O | PRO | 175 | 0.000 | −4.556 | 32.455 | 1.00 | 9.54 |
| ATOM | 766 | N | GLY | 176 | 1.765 | −4.207 | 33.806 | 1.00 | 9.48 |
| ATOM | 767 | CA | GLY | 176 | 2.226 | −5.577 | 33.690 | 1.00 | 9.58 |
| ATOM | 768 | C | GLY | 176 | 3.192 | −5.838 | 32.554 | 1.00 | 9.81 |
| ATOM | 769 | O | GLY | 176 | 3.677 | −6.958 | 32.409 | 1.00 | 10.30 |
| ATOM | 770 | N | MET | 177 | 3.463 | −4.823 | 31.739 | 1.00 | 8.82 |
| ATOM | 771 | CA | MET | 177 | 4.401 | −4.975 | 30.629 | 1.00 | 8.52 |
| ATOM | 772 | CB | MET | 177 | 3.760 | −4.515 | 29.320 | 1.00 | 10.08 |
| ATOM | 773 | CG | MET | 177 | 2.649 | −5.439 | 28.859 | 1.00 | 11.46 |
| ATOM | 774 | SD | MET | 177 | 2.093 | −5.117 | 27.179 | 1.00 | 12.85 |
| ATOM | 775 | CE | MET | 177 | 0.393 | −5.651 | 27.292 | 1.00 | 13.23 |
| ATOM | 776 | C | MET | 177 | 5.660 | −4.172 | 30.930 | 1.00 | 7.98 |
| ATOM | 777 | O | MET | 177 | 5.579 | −3.010 | 31.326 | 1.00 | 7.40 |
| ATOM | 778 | N | PHE | 178 | 6.820 | −4.797 | 30.739 | 1.00 | 7.68 |
| ATOM | 779 | CA | PHE | 178 | 8.094 | −4.160 | 31.049 | 1.00 | 7.09 |
| ATOM | 780 | CB | PHE | 178 | 8.743 | −4.864 | 32.250 | 1.00 | 8.40 |
| ATOM | 781 | CG | PHE | 178 | 7.874 | −4.908 | 33.477 | 1.00 | 9.38 |
| ATOM | 782 | CD1 | PHE | 178 | 6.767 | −5.754 | 33.536 | 1.00 | 9.55 |
| ATOM | 783 | CD2 | PHE | 178 | 8.150 | −4.090 | 34.569 | 1.00 | 9.47 |
| ATOM | 784 | CE1 | PHE | 178 | 5.947 | −5.783 | 34.664 | 1.00 | 9.89 |
| ATOM | 785 | CE2 | PHE | 178 | 7.336 | −4.112 | 35.699 | 1.00 | 10.43 |
| ATOM | 786 | CZ | PHE | 178 | 6.232 | −4.960 | 35.746 | 1.00 | 9.58 |
| ATOM | 787 | C | PHE | 178 | 9.107 | −4.119 | 29.914 | 1.00 | 7.00 |
| ATOM | 788 | O | PHE | 178 | 9.128 | −4.993 | 29.044 | 1.00 | 6.97 |
| ATOM | 789 | N | ILE | 179 | 9.955 | −3.094 | 29.943 | 1.00 | 6.62 |
| ATOM | 790 | CA | ILE | 179 | 11.010 | −2.925 | 28.949 | 1.00 | 6.43 |
| ATOM | 791 | CB | ILE | 179 | 11.736 | −1.569 | 29.124 | 1.00 | 6.72 |
| ATOM | 792 | CG2 | ILE | 179 | 12.947 | −1.496 | 28.202 | 1.00 | 7.70 |
| ATOM | 793 | CG1 | ILE | 179 | 10.767 | −0.418 | 28.847 | 1.00 | 6.16 |
| ATOM | 794 | CD1 | ILE | 179 | 11.411 | 0.966 | 28.933 | 1.00 | 6.64 |
| ATOM | 795 | C | ILE | 179 | 12.017 | −4.038 | 29.195 | 1.00 | 6.58 |
| ATOM | 796 | O | ILE | 179 | 12.330 | −4.344 | 30.342 | 1.00 | 6.50 |
| ATOM | 797 | N | ALA | 180 | 12.531 | −4.639 | 28.129 | 1.00 | 6.56 |
| ATOM | 798 | CA | ALA | 180 | 13.496 | −5.712 | 28.302 | 1.00 | 6.46 |

-continued

| | | | | | | | | | |
|---|---|---|---|---|---|---|---|---|---|
| ATOM | 799 | CB | ALA | 180 | 12.770 | −7.005 | 28.677 | 1.00 | 6.63 |
| ATOM | 800 | C | ALA | 180 | 14.369 | −5.953 | 27.082 | 1.00 | 6.85 |
| ATOM | 801 | O | ALA | 180 | 13.950 | −5.731 | 25.945 | 1.00 | 6.24 |
| ATOM | 802 | N | LEU | 181 | 15.593 | −6.405 | 27.344 | 1.00 | 6.67 |
| ATOM | 803 | CA | LEU | 181 | 16.561 | −6.745 | 26.305 | 1.00 | 7.47 |
| ATOM | 804 | CB | LEU | 181 | 17.795 | −5.839 | 26.379 | 1.00 | 7.48 |
| ATOM | 805 | CG | LEU | 181 | 17.654 | −4.375 | 25.964 | 1.00 | 7.58 |
| ATOM | 806 | CD1 | LEU | 181 | 18.985 | −3.680 | 26.176 | 1.00 | 7.44 |
| ATOM | 807 | CD2 | LEU | 181 | 17.230 | −4.274 | 24.503 | 1.00 | 8.28 |
| ATOM | 808 | C | LEU | 181 | 16.987 | −8.186 | 26.571 | 1.00 | 8.19 |
| ATOM | 809 | O | LEU | 181 | 17.144 | −8.591 | 27.725 | 1.00 | 8.34 |
| ATOM | 810 | N | ALA | 182 | 17.176 | −8.956 | 25.508 | 1.00 | 9.76 |
| ATOM | 811 | CA | ALA | 182 | 17.583 | −10.346 | 25.648 | 1.00 | 9.78 |
| ATOM | 812 | CB | ALA | 182 | 16.934 | −11.180 | 24.570 | 1.00 | 13.35 |
| ATOM | 813 | C | ALA | 182 | 19.095 | −10.461 | 25.558 | 1.00 | 10.87 |
| ATOM | 814 | O | ALA | 182 | 19.778 | −9.487 | 25.243 | 1.00 | 8.94 |
| ATOM | 815 | N | LYS | 183 | 19.616 | −11.657 | 25.825 | 1.00 | 11.33 |
| ATOM | 816 | CA | LYS | 183 | 21.054 | −11.872 | 25.779 | 1.00 | 12.77 |
| ATOM | 817 | CB | LYS | 183 | 21.402 | −13.275 | 26.299 | 1.00 | 13.33 |
| ATOM | 818 | CG | LYS | 183 | 20.846 | −14.427 | 25.487 | 1.00 | 14.58 |
| ATOM | 819 | CD | LYS | 183 | 21.231 | −15.760 | 26.124 | 1.00 | 15.82 |
| ATOM | 820 | CE | LYS | 183 | 20.900 | −16.937 | 25.222 | 1.00 | 17.00 |
| ATOM | 821 | NZ | LYS | 183 | 19.446 | −17.024 | 24.917 | 1.00 | 18.11 |
| ATOM | 822 | C | LYS | 183 | 21.645 | −11.650 | 24.389 | 1.00 | 13.15 |
| ATOM | 823 | O | LYS | 183 | 22.855 | −11.458 | 24.254 | 1.00 | 14.24 |
| ATOM | 824 | N | ASN | 184 | 20.804 | −11.668 | 23.356 | 1.00 | 13.74 |
| ATOM | 825 | CA | ASN | 184 | 21.291 | −11.440 | 21.998 | 1.00 | 14.34 |
| ATOM | 826 | CB | ASN | 184 | 20.399 | −12.141 | 20.960 | 1.00 | 15.53 |
| ATOM | 827 | CG | ASN | 184 | 18.962 | −11.657 | 20.985 | 1.00 | 16.25 |
| ATOM | 828 | OD1 | ASN | 184 | 18.628 | −10.692 | 21.668 | 1.00 | 16.76 |
| ATOM | 829 | ND2 | ASN | 184 | 18.102 | −12.329 | 20.229 | 1.00 | 17.81 |
| ATOM | 830 | C | ASN | 184 | 21.369 | −9.943 | 21.701 | 1.00 | 14.45 |
| ATOM | 831 | O | ASN | 184 | 21.711 | −9.535 | 20.590 | 1.00 | 14.60 |
| ATOM | 832 | N | GLY | 185 | 21.051 | −9.132 | 22.708 | 1.00 | 13.68 |
| ATOM | 833 | CA | GLY | 185 | 21.109 | −7.688 | 22.557 | 1.00 | 13.05 |
| ATOM | 834 | C | GLY | 185 | 19.904 | −7.049 | 21.894 | 1.00 | 12.79 |
| ATOM | 835 | O | GLY | 185 | 19.911 | −5.848 | 21.631 | 1.00 | 13.80 |
| ATOM | 836 | N | ALA | 186 | 18.873 | −7.841 | 21.619 | 1.00 | 10.99 |
| ATOM | 837 | CA | ALA | 186 | 17.670 | −7.318 | 20.985 | 1.00 | 10.27 |
| ATOM | 838 | CB | ALA | 186 | 17.246 | −8.225 | 19.828 | 1.00 | 10.89 |
| ATOM | 839 | C | ALA | 186 | 16.545 | −7.197 | 22.004 | 1.00 | 8.96 |
| ATOM | 840 | O | ALA | 186 | 16.578 | −7.820 | 23.063 | 1.00 | 8.77 |
| ATOM | 841 | N | THR | 187 | 15.545 | −6.385 | 21.687 | 1.00 | 8.86 |
| ATOM | 842 | CA | THR | 187 | 14.427 | −6.203 | 22.600 | 1.00 | 7.58 |
| ATOM | 843 | CB | THR | 187 | 13.518 | −5.051 | 22.146 | 1.00 | 7.14 |
| ATOM | 844 | OG1 | THR | 187 | 13.033 | −5.325 | 20.825 | 1.00 | 7.19 |
| ATOM | 845 | CG2 | THR | 187 | 14.281 | −3.734 | 22.146 | 1.00 | 6.53 |
| ATOM | 846 | C | THR | 187 | 13.562 | −7.452 | 22.700 | 1.00 | 8.41 |
| ATOM | 847 | O | THR | 187 | 13.527 | −8.279 | 21.788 | 1.00 | 8.64 |
| ATOM | 848 | N | LYS | 188 | 12.876 | −7.585 | 23.829 | 1.00 | 8.14 |
| ATOM | 849 | CA | LYS | 188 | 11.953 | −8.684 | 24.056 | 1.00 | 9.20 |
| ATOM | 850 | CB | LYS | 188 | 12.271 | −9.412 | 25.363 | 1.00 | 10.91 |
| ATOM | 851 | CG | LYS | 188 | 13.456 | −10.356 | 25.287 | 1.00 | 12.37 |
| ATOM | 852 | CD | LYS | 188 | 13.577 | −11.140 | 26.583 | 1.00 | 14.48 |
| ATOM | 853 | CE | LYS | 188 | 14.470 | −12.345 | 26.416 | 1.00 | 16.86 |
| ATOM | 854 | NZ | LYS | 188 | 13.932 | −13.324 | 25.422 | 1.00 | 15.93 |
| ATOM | 855 | C | LYS | 188 | 10.588 | −8.020 | 24.167 | 1.00 | 9.15 |
| ATOM | 856 | O | LYS | 188 | 10.506 | −6.823 | 24.443 | 1.00 | 8.81 |
| ATOM | 857 | N | LYS | 189 | 9.523 | −8.783 | 23.944 | 1.00 | 8.51 |
| ATOM | 858 | CA | LYS | 189 | 8.170 | −8.242 | 24.040 | 1.00 | 9.55 |
| ATOM | 859 | CB | LYS | 189 | 7.164 | −9.237 | 23.452 | 1.00 | 11.24 |
| ATOM | 860 | CG | LYS | 189 | 7.433 | −9.583 | 21.991 | 1.00 | 13.77 |
| ATOM | 861 | CD | LYS | 189 | 7.115 | −8.412 | 21.070 | 1.00 | 15.40 |
| ATOM | 862 | CE | LYS | 189 | 5.666 | −8.448 | 20.601 | 1.00 | 18.07 |
| ATOM | 863 | NZ | LYS | 189 | 4.706 | −8.523 | 21.729 | 1.00 | 20.82 |
| ATOM | 864 | C | LYS | 189 | 7.842 | −7.965 | 25.506 | 1.00 | 8.74 |
| ATOM | 865 | O | LYS | 189 | 8.100 | −8.799 | 26.372 | 1.00 | 8.90 |
| ATOM | 866 | N | GLY | 190 | 7.273 | −6.793 | 25.776 | 1.00 | 7.88 |
| ATOM | 867 | CA | GLY | 190 | 6.940 | −6.421 | 27.140 | 1.00 | 8.10 |
| ATOM | 868 | C | GLY | 190 | 5.938 | −7.314 | 27.851 | 1.00 | 8.54 |
| ATOM | 869 | O | GLY | 190 | 5.894 | −7.339 | 29.086 | 1.00 | 7.39 |
| ATOM | 870 | N | ASN | 191 | 5.130 | −8.045 | 27.090 | 1.00 | 8.98 |
| ATOM | 871 | CA | ASN | 191 | 4.135 | −8.926 | 27.689 | 1.00 | 10.89 |
| ATOM | 872 | CB | ASN | 191 | 2.812 | −8.829 | 26.922 | 1.00 | 12.28 |
| ATOM | 873 | CG | ASN | 191 | 2.937 | −9.274 | 25.483 | 1.00 | 13.78 |
| ATOM | 874 | OD1 | ASN | 191 | 4.035 | −9.334 | 24.931 | 1.00 | 13.27 |
| ATOM | 875 | ND2 | ASN | 191 | 1.803 | −9.575 | 24.858 | 1.00 | 15.88 |
| ATOM | 876 | C | ASN | 191 | 4.607 | −10.377 | 27.756 | 1.00 | 11.62 |
| ATOM | 877 | O | ASN | 191 | 3.802 | −11.295 | 27.916 | 1.00 | 10.96 |

-continued

| | | | | | | | | |
|---|---|---|---|---|---|---|---|---|
| ATOM | 878 | N | ARG | 192 | 5.917 | −10.574 | 27.639 | 1.00 | 12.11 |
| ATOM | 879 | CA | ARG | 192 | 6.503 | −11.910 | 27.715 | 1.00 | 13.33 |
| ATOM | 880 | CB | ARG | 192 | 7.076 | −12.324 | 26.356 | 1.00 | 14.44 |
| ATOM | 881 | CG | ARG | 192 | 6.026 | −12.464 | 25.263 | 1.00 | 16.19 |
| ATOM | 882 | CD | ARG | 192 | 6.663 | −12.877 | 23.948 | 1.00 | 19.13 |
| ATOM | 883 | NE | ARG | 192 | 7.220 | −14.224 | 24.013 | 1.00 | 22.54 |
| ATOM | 884 | CZ | ARG | 192 | 6.499 | −15.337 | 23.905 | 1.00 | 24.09 |
| ATOM | 885 | NH1 | ARG | 192 | 5.188 | −15.266 | 23.725 | 1.00 | 24.60 |
| ATOM | 886 | NH2 | ARG | 192 | 7.091 | −16.521 | 23.977 | 1.00 | 25.22 |
| ATOM | 887 | C | ARG | 192 | 7.597 | −11.957 | 28.780 | 1.00 | 13.36 |
| ATOM | 888 | O | ARG | 192 | 8.358 | −12.919 | 28.861 | 1.00 | 13.48 |
| ATOM | 889 | N | VAL | 193 | 7.663 | −10.908 | 29.596 | 1.00 | 13.03 |
| ATOM | 890 | CA | VAL | 193 | 8.654 | −10.812 | 30.665 | 1.00 | 12.85 |
| ATOM | 891 | CB | VAL | 193 | 9.800 | −9.841 | 30.284 | 1.00 | 11.28 |
| ATOM | 892 | CG1 | VAL | 193 | 10.543 | −10.360 | 29.064 | 1.00 | 11.22 |
| ATOM | 893 | CG2 | VAL | 193 | 9.235 | −8.457 | 30.003 | 1.00 | 11.65 |
| ATOM | 894 | C | VAL | 193 | 8.010 | −10.305 | 31.957 | 1.00 | 13.63 |
| ATOM | 895 | O | VAL | 193 | 6.958 | −9.660 | 31.927 | 1.00 | 14.01 |
| ATOM | 896 | N | SER | 194 | 8.647 | −10.605 | 33.086 | 1.00 | 14.34 |
| ATOM | 897 | CA | SER | 194 | 8.166 | −10.172 | 34.398 | 1.00 | 15.34 |
| ATOM | 898 | CB | SER | 194 | 7.728 | −11.372 | 35.238 | 1.00 | 16.67 |
| ATOM | 899 | OG | SER | 194 | 8.833 | −12.193 | 35.565 | 1.00 | 19.38 |
| ATOM | 900 | C | SER | 194 | 9.315 | −9.453 | 35.095 | 1.00 | 14.47 |
| ATOM | 901 | O | SER | 194 | 10.480 | −9.720 | 34.810 | 1.00 | 13.57 |
| ATOM | 902 | N | PRO | 195 | 9.003 | −8.545 | 36.034 | 1.00 | 14.17 |
| ATOM | 903 | CD | PRO | 195 | 7.669 | −8.211 | 36.562 | 1.00 | 14.38 |
| ATOM | 904 | CA | PRO | 195 | 10.048 | −7.804 | 36.745 | 1.00 | 13.64 |
| ATOM | 905 | CB | PRO | 195 | 9.252 | −6.826 | 37.607 | 1.00 | 14.45 |
| ATOM | 906 | CG | PRO | 195 | 8.002 | −7.588 | 37.900 | 1.00 | 14.65 |
| ATOM | 907 | C | PRO | 195 | 11.033 | −8.638 | 37.557 | 1.00 | 13.10 |
| ATOM | 908 | O | PRO | 195 | 12.046 | −8.118 | 38.007 | 1.00 | 12.82 |
| ATOM | 909 | N | THR | 196 | 10.746 | −9.921 | 37.753 | 1.00 | 12.72 |
| ATOM | 910 | CA | THR | 196 | 11.666 | −10.771 | 38.509 | 1.00 | 12.30 |
| ATOM | 911 | CB | THR | 196 | 10.950 | −11.988 | 39.121 | 1.00 | 12.60 |
| ATOM | 912 | OG1 | THR | 196 | 10.332 | −12.753 | 38.079 | 1.00 | 12.75 |
| ATOM | 913 | CG2 | THR | 196 | 9.898 | −11.540 | 40.121 | 1.00 | 13.99 |
| ATOM | 914 | C | THR | 196 | 12.785 | −11.283 | 37.611 | 1.00 | 12.27 |
| ATOM | 915 | O | THR | 196 | 13.798 | −11.786 | 38.094 | 1.00 | 12.60 |
| ATOM | 916 | N | MET | 197 | 12.593 | −11.138 | 36.303 | 1.00 | 11.81 |
| ATOM | 917 | CA | MET | 197 | 13.561 | −11.596 | 35.309 | 1.00 | 11.06 |
| ATOM | 918 | CB | MET | 197 | 12.832 | −11.920 | 34.005 | 1.00 | 11.47 |
| ATOM | 919 | CG | MET | 197 | 11.814 | −13.042 | 34.142 | 1.00 | 13.03 |
| ATOM | 920 | SD | MET | 197 | 10.747 | −13.178 | 32.697 | 1.00 | 13.94 |
| ATOM | 921 | CE | MET | 197 | 11.878 | −13.884 | 31.521 | 1.00 | 14.56 |
| ATOM | 922 | C | MET | 197 | 14.662 | −10.574 | 35.050 | 1.00 | 10.53 |
| ATOM | 923 | O | MET | 197 | 14.399 | −9.379 | 34.943 | 1.00 | 9.30 |
| ATOM | 924 | N | ALA | 198 | 15.896 | −11.060 | 34.942 | 1.00 | 9.44 |
| ATOM | 925 | CA | ALA | 198 | 17.051 | −10.205 | 34.708 | 1.00 | 8.58 |
| ATOM | 926 | CB | ALA | 198 | 18.327 | −11.049 | 34.690 | 1.00 | 9.44 |
| ATOM | 927 | C | ALA | 198 | 16.958 | −9.378 | 33.429 | 1.00 | 8.75 |
| ATOM | 928 | O | ALA | 198 | 17.544 | −8.296 | 33.349 | 1.00 | 8.37 |
| ATOM | 929 | N | VAL | 199 | 16.234 | −9.877 | 32.431 | 1.00 | 7.63 |
| ATOM | 930 | CA | VAL | 199 | 16.097 | −9.152 | 31.170 | 1.00 | 6.86 |
| ATOM | 931 | CB | VAL | 199 | 15.388 | −10.017 | 30.092 | 1.00 | 7.52 |
| ATOM | 932 | CG1 | VAL | 199 | 16.272 | −11.193 | 29.714 | 1.00 | 8.00 |
| ATOM | 933 | CG2 | VAL | 199 | 14.043 | −10.511 | 30.608 | 1.00 | 7.54 |
| ATOM | 934 | C | VAL | 199 | 15.353 | −7.819 | 31.325 | 1.00 | 6.93 |
| ATOM | 935 | O | VAL | 199 | 15.382 | −6.981 | 30.421 | 1.00 | 5.85 |
| ATOM | 936 | N | THR | 200 | 14.704 | −7.615 | 32.470 | 1.00 | 6.77 |
| ATOM | 937 | CA | THR | 200 | 13.972 | −6.369 | 32.721 | 1.00 | 7.57 |
| ATOM | 938 | CB | THR | 200 | 12.578 | −6.631 | 33.340 | 1.00 | 8.45 |
| ATOM | 939 | OG1 | THR | 200 | 12.736 | −7.158 | 34.664 | 1.00 | 8.56 |
| ATOM | 940 | CG2 | THR | 200 | 11.790 | −7.622 | 32.500 | 1.00 | 8.63 |
| ATOM | 941 | C | THR | 200 | 14.725 | −5.457 | 33.692 | 1.00 | 7.78 |
| ATOM | 942 | O | THR | 200 | 14.247 | −4.370 | 34.028 | 1.00 | 7.71 |
| ATOM | 943 | N | HIS | 201 | 15.899 | −5.896 | 34.137 | 1.00 | 7.34 |
| ATOM | 944 | CA | HIS | 201 | 16.695 | −5.125 | 35.095 | 1.00 | 7.59 |
| ATOM | 945 | CB | HIS | 201 | 17.452 | −6.073 | 36.028 | 1.00 | 8.17 |
| ATOM | 946 | CG | HIS | 201 | 16.568 | −6.922 | 36.887 | 1.00 | 9.32 |
| ATOM | 947 | CD2 | HIS | 201 | 16.861 | −7.736 | 37.930 | 1.00 | 9.55 |
| ATOM | 948 | ND1 | HIS | 201 | 15.205 | −7.007 | 36.709 | 1.00 | 10.97 |
| ATOM | 949 | CE1 | HIS | 201 | 14.695 | −7.834 | 37.604 | 1.00 | 9.67 |
| ATOM | 950 | NE2 | HIS | 201 | 15.681 | −8.290 | 38.358 | 1.00 | 11.80 |
| ATOM | 951 | C | HIS | 201 | 17.704 | −4.199 | 34.426 | 1.00 | 7.38 |
| ATOM | 952 | O | HIS | 201 | 18.618 | −4.663 | 33.742 | 1.00 | 7.78 |
| ATOM | 953 | N | PHE | 202 | 17.553 | −2.894 | 34.640 | 1.00 | 7.48 |
| ATOM | 954 | CA | PHE | 202 | 18.466 | −1.922 | 34.048 | 1.00 | 7.69 |
| ATOM | 955 | CB | PHE | 202 | 17.716 | −0.988 | 33.091 | 1.00 | 7.39 |
| ATOM | 956 | CG | PHE | 202 | 17.187 | −1.673 | 31.866 | 1.00 | 7.17 |

-continued

| | | | | | | | | |
|---|---|---|---|---|---|---|---|---|
| ATOM | 957 | CD1 | PHE | 202 | 15.966 | −2.334 | 31.894 | 1.00 | 7.73 |
| ATOM | 958 | CD2 | PHE | 202 | 17.922 | −1.674 | 30.686 | 1.00 | 6.55 |
| ATOM | 959 | CE1 | PHE | 202 | 15.480 | −2.988 | 30.765 | 1.00 | 6.46 |
| ATOM | 960 | CE2 | PHE | 202 | 17.447 | −2.327 | 29.545 | 1.00 | 6.72 |
| ATOM | 961 | CZ | PHE | 202 | 16.220 | −2.986 | 29.587 | 1.00 | 6.52 |
| ATOM | 962 | C | PHE | 202 | 19.188 | −1.080 | 35.092 | 1.00 | 8.95 |
| ATOM | 963 | O | PHE | 202 | 18.561 | −0.494 | 35.980 | 1.00 | 9.11 |
| ATOM | 964 | N | LEU | 203 | 20.511 | −1.019 | 34.972 | 1.00 | 9.21 |
| ATOM | 965 | CA | LEU | 203 | 21.334 | −0.237 | 35.890 | 1.00 | 10.82 |
| ATOM | 966 | CB | LEU | 203 | 22.627 | −0.989 | 36.224 | 1.00 | 10.86 |
| ATOM | 967 | CG | LEU | 203 | 23.571 | −0.292 | 37.213 | 1.00 | 11.00 |
| ATOM | 968 | CD1 | LEU | 203 | 22.887 | −0.188 | 38.568 | 1.00 | 12.23 |
| ATOM | 969 | CD2 | LEU | 203 | 24.871 | −1.069 | 37.341 | 1.00 | 11.91 |
| ATOM | 970 | C | LEU | 203 | 21.689 | 1.103 | 35.256 | 1.00 | 12.02 |
| ATOM | 971 | O | LEU | 203 | 22.303 | 1.149 | 34.191 | 1.00 | 11.12 |
| ATOM | 972 | N | PRO | 204 | 21.288 | 2.214 | 35.892 | 1.00 | 13.88 |
| ATOM | 973 | CD | PRO | 204 | 20.358 | 2.318 | 37.029 | 1.00 | 14.72 |
| ATOM | 974 | CA | PRO | 204 | 21.596 | 3.540 | 35.351 | 1.00 | 16.16 |
| ATOM | 975 | CB | PRO | 204 | 20.832 | 4.478 | 36.280 | 1.00 | 16.31 |
| ATOM | 976 | CG | PRO | 204 | 19.679 | 3.632 | 36.748 | 1.00 | 15.39 |
| ATOM | 977 | C | PRO | 204 | 23.101 | 3.786 | 35.409 | 1.00 | 18.73 |
| ATOM | 978 | O | PRO | 204 | 23.716 | 3.625 | 36.466 | 1.00 | 18.38 |
| ATOM | 979 | N | ARG | 205 | 23.688 | 4.165 | 34.278 | 1.00 | 21.09 |
| ATOM | 980 | CA | ARG | 205 | 25.123 | 4.432 | 34.213 | 1.00 | 24.19 |
| ATOM | 981 | CB | ARG | 205 | 25.867 | 3.219 | 33.650 | 1.00 | 25.55 |
| ATOM | 982 | CG | ARG | 205 | 25.752 | 1.972 | 34.509 | 1.00 | 28.06 |
| ATOM | 983 | CD | ARG | 205 | 27.109 | 1.329 | 34.774 | 1.00 | 30.17 |
| ATOM | 984 | NE | ARG | 205 | 28.040 | 2.244 | 35.432 | 1.00 | 31.85 |
| ATOM | 985 | CZ | ARG | 205 | 28.888 | 3.045 | 34.792 | 1.00 | 33.10 |
| ATOM | 986 | NH1 | ARG | 205 | 28.933 | 3.050 | 33.464 | 1.00 | 33.73 |
| ATOM | 987 | NH2 | ARG | 205 | 29.690 | 3.849 | 35.480 | 1.00 | 33.12 |
| ATOM | 988 | C | ARG | 205 | 25.442 | 5.659 | 33.366 | 1.00 | 25.09 |
| ATOM | 989 | O | ARG | 205 | 24.577 | 6.174 | 32.659 | 1.00 | 24.94 |
| ATOM | 990 | N | ALA | 206 | 26.690 | 6.117 | 33.459 | 1.00 | 26.79 |
| ATOM | 991 | CA | ALA | 206 | 27.188 | 7.281 | 32.722 | 1.00 | 28.01 |
| ATOM | 992 | CB | ALA | 206 | 28.274 | 6.843 | 31.745 | 1.00 | 28.80 |
| ATOM | 993 | C | ALA | 206 | 26.107 | 8.065 | 31.983 | 1.00 | 28.96 |
| ATOM | 994 | O | ALA | 206 | 26.376 | 8.463 | 30.829 | 1.00 | 29.66 |
| ATOM | 995 | O1 | HOH | 1000 | 12.829 | −2.036 | 17.116 | 1.00 | 7.18 |
| ATOM | 996 | O1 | HOH | 1001 | 20.982 | 8.993 | 22.203 | 1.00 | 7.57 |
| ATOM | 997 | O1 | HOH | 1002 | 12.768 | 12.229 | 28.379 | 1.00 | 10.08 |
| ATOM | 998 | O1 | HOH | 1003 | 21.297 | 3.228 | 27.387 | 1.00 | 6.83 |
| ATOM | 999 | O1 | HOH | 1004 | 2.864 | 4.158 | 28.500 | 1.00 | 7.52 |
| ATOM | 1000 | O1 | HOH | 1005 | 10.142 | −1.516 | 16.908 | 1.00 | 7.61 |
| ATOM | 1001 | O1 | HOH | 1006 | 11.860 | −3.327 | 19.508 | 1.00 | 5.26 |
| ATOM | 1002 | O1 | HOH | 1007 | 9.727 | 7.593 | 26.490 | 1.00 | 7.03 |
| ATOM | 1003 | O1 | HOH | 1008 | 10.236 | −4.757 | 26.340 | 1.00 | 7.00 |
| ATOM | 1004 | O1 | HOH | 1009 | 10.856 | 2.908 | 42.825 | 1.00 | 6.81 |
| ATOM | 1005 | O1 | HOH | 1010 | 6.747 | 4.115 | 39.695 | 1.00 | 8.95 |
| ATOM | 1006 | O1 | HOH | 1011 | 12.036 | −3.230 | 32.828 | 1.00 | 8.27 |
| ATOM | 1007 | O1 | HOH | 1012 | 4.734 | 16.208 | 33.512 | 1.00 | 12.05 |
| ATOM | 1008 | O1 | HOH | 1013 | 10.093 | 0.852 | 15.744 | 1.00 | 8.23 |
| ATOM | 1009 | O1 | HOH | 1014 | 0.631 | 2.544 | 19.025 | 1.00 | 10.23 |
| ATOM | 1010 | O1 | HOH | 1015 | 18.399 | −0.846 | 45.247 | 1.00 | 8.81 |
| ATOM | 1011 | O1 | HOH | 1016 | 3.640 | 7.004 | 20.379 | 1.00 | 5.67 |
| ATOM | 1012 | O1 | HOH | 1017 | 19.978 | −6.895 | 33.952 | 1.00 | 10.33 |
| ATOM | 1013 | O1 | HOH | 1018 | 3.469 | 1.860 | 26.778 | 1.00 | 10.74 |
| ATOM | 1014 | O1 | HOH | 1019 | 19.254 | 1.746 | 45.513 | 1.00 | 11.57 |
| ATOM | 1015 | O1 | HOH | 1020 | 9.787 | −5.206 | 22.223 | 1.00 | 9.48 |
| ATOM | 1016 | O1 | HOH | 1021 | 9.165 | 4.101 | 14.820 | 1.00 | 9.74 |
| ATOM | 1017 | O1 | HOH | 1022 | 19.029 | 7.930 | 20.394 | 1.00 | 7.35 |
| ATOM | 1018 | O1 | HOH | 1023 | 11.450 | −7.648 | 40.765 | 1.00 | 14.67 |
| ATOM | 1019 | O1 | HOH | 1024 | 10.751 | −7.011 | 20.455 | 1.00 | 9.99 |
| ATOM | 1020 | O1 | HOH | 1025 | −0.784 | 0.040 | 20.721 | 1.00 | 11.72 |
| ATOM | 1021 | O1 | HOH | 1026 | −2.374 | 3.652 | 22.178 | 1.00 | 16.42 |
| ATOM | 1022 | O1 | HOH | 1027 | 16.329 | 18.885 | 28.375 | 1.00 | 19.76 |
| ATOM | 1023 | O1 | HOH | 1028 | 18.501 | −6.259 | 40.698 | 1.00 | 14.77 |
| ATOM | 1024 | O1 | HOH | 1029 | 18.291 | −13.454 | 23.318 | 1.00 | 15.78 |
| ATOM | 1025 | O1 | HOH | 1030 | 10.174 | 5.278 | 12.637 | 1.00 | 13.08 |
| ATOM | 1026 | O1 | HOH | 1031 | 1.243 | 0.722 | 34.708 | 1.00 | 17.19 |
| ATOM | 1027 | O1 | HOH | 1032 | 2.523 | −3.821 | 18.445 | 1.00 | 16.48 |
| ATOM | 1028 | O1 | HOH | 1033 | 15.902 | −4.895 | 19.077 | 1.00 | 10.14 |
| ATOM | 1029 | O1 | HOH | 1034 | 16.085 | 18.258 | 38.411 | 1.00 | 20.04 |
| ATOM | 1030 | O1 | HOH | 1035 | 8.277 | 3.225 | 41.854 | 1.00 | 12.99 |
| ATOM | 1031 | O1 | HOH | 1036 | 16.439 | 13.001 | 35.214 | 1.00 | 16.54 |
| ATOM | 1032 | O1 | HOH | 1037 | 28.131 | 5.663 | 18.293 | 1.00 | 20.92 |
| ATOM | 1033 | O1 | HOH | 1038 | 14.371 | −11.433 | 40.776 | 1.00 | 17.19 |
| ATOM | 1034 | O1 | HOH | 1039 | 6.487 | 15.695 | 21.119 | 1.00 | 14.88 |
| ATOM | 1035 | O1 | HOH | 1040 | 2.321 | −12.928 | 26.470 | 1.00 | 11.64 |

-continued

| | | | | | | | | |
|---|---|---|---|---|---|---|---|---|
| ATOM | 1036 | O1 | HOH | 1041 | 10.693 | 5.971 | 40.782 | 1.00 | 17.64 |
| ATOM | 1037 | O1 | HOH | 1042 | 12.532 | 16.814 | 29.258 | 1.00 | 17.91 |
| ATOM | 1038 | O1 | HOH | 1043 | 15.955 | −13.066 | 32.485 | 1.00 | 14.81 |
| ATOM | 1039 | O1 | HOH | 1044 | 18.984 | 3.255 | 12.162 | 1.00 | 21.70 |
| ATOM | 1040 | O1 | HOH | 1045 | 10.025 | 10.429 | 37.944 | 1.00 | 16.17 |
| ATOM | 1041 | O1 | HOH | 1046 | 10.284 | −14.324 | 27.916 | 1.00 | 18.92 |
| ATOM | 1042 | O1 | HOH | 1047 | 14.189 | 5.045 | 17.917 | 1.00 | 14.25 |
| ATOM | 1043 | O1 | HOH | 1048 | 1.288 | −3.987 | 37.554 | 1.00 | 20.26 |
| ATOM | 1044 | O1 | HOH | 1049 | 10.779 | −7.111 | 14.686 | 1.00 | 24.75 |
| ATOM | 1045 | O1 | HOH | 1050 | 11.650 | 13.767 | 17.828 | 1.00 | 19.59 |
| ATOM | 1046 | O1 | HOH | 1051 | 14.534 | 9.188 | 36.954 | 1.00 | 19.75 |
| ATOM | 1047 | O1 | HOH | 1052 | 19.606 | −7.904 | 38.613 | 1.00 | 20.20 |
| ATOM | 1048 | O1 | HOH | 1053 | 9.427 | 9.736 | 48.436 | 1.00 | 15.68 |
| ATOM | 1049 | O1 | HOH | 1054 | −2.792 | −4.538 | 26.019 | 1.00 | 26.55 |
| ATOM | 1050 | O1 | HOH | 1055 | −0.725 | −9.213 | 26.754 | 1.00 | 18.89 |
| ATOM | 1051 | O1 | HOH | 1056 | −0.278 | 6.480 | 29.432 | 1.00 | 23.19 |
| ATOM | 1052 | O1 | HOH | 1057 | 25.587 | −11.455 | 24.178 | 1.00 | 14.80 |
| ATOM | 1053 | O1 | HOH | 1058 | 16.900 | 10.379 | 36.579 | 1.00 | 17.89 |
| ATOM | 1054 | O1 | HOH | 1059 | 3.126 | 15.011 | 20.955 | 1.00 | 13.94 |
| ATOM | 1055 | O1 | HOH | 1060 | 24.968 | 5.423 | 18.006 | 1.00 | 15.86 |
| ATOM | 1056 | O1 | HOH | 1061 | 18.376 | −0.133 | 12.322 | 1.00 | 22.38 |
| ATOM | 1057 | O1 | HOH | 1062 | 15.661 | −10.620 | 22.135 | 1.00 | 20.09 |
| ATOM | 1058 | O1 | HOH | 1063 | 14.444 | −8.692 | 41.510 | 1.00 | 17.78 |
| ATOM | 1059 | O1 | HOH | 1064 | −2.099 | 2.685 | 19.269 | 1.00 | 18.56 |
| ATOM | 1060 | O1 | HOH | 1065 | 15.065 | −14.513 | 30.168 | 1.00 | 20.78 |
| ATOM | 1061 | O1 | HOH | 1066 | −0.478 | −12.428 | 26.525 | 1.00 | 19.85 |
| ATOM | 1062 | O1 | HOH | 1067 | 24.619 | −2.274 | 41.474 | 1.00 | 20.99 |
| ATOM | 1063 | O1 | HOH | 1068 | 14.937 | 4.314 | 41.154 | 1.00 | 23.31 |
| ATOM | 1064 | O1 | HOH | 1069 | 18.536 | 3.179 | 40.506 | 1.00 | 20.39 |
| ATOM | 1065 | O1 | HOH | 1070 | 12.859 | 4.828 | 42.895 | 1.00 | 23.36 |
| ATOM | 1066 | O1 | HOH | 1071 | 21.098 | −7.930 | 36.367 | 1.00 | 22.36 |
| ATOM | 1067 | O1 | HOH | 1072 | −4.171 | −0.822 | 29.589 | 1.00 | 31.08 |
| ATOM | 1068 | O1 | HOH | 1073 | 5.760 | 16.825 | 18.804 | 1.00 | 26.85 |
| ATOM | 1069 | O1 | HOH | 1074 | 14.347 | 16.052 | 36.421 | 1.00 | 26.89 |
| ATOM | 1070 | O1 | HOH | 1075 | 26.493 | −4.497 | 20.667 | 1.00 | 19.77 |
| ATOM | 1071 | O1 | HOH | 1076 | 2.436 | 9.335 | 39.933 | 1.00 | 22.58 |
| ATOM | 1072 | O1 | HOH | 1077 | 28.166 | −2.047 | 20.549 | 1.00 | 17.57 |
| ATOM | 1073 | O1 | HOH | 1078 | 26.366 | −10.689 | 21.612 | 1.00 | 24.57 |
| ATOM | 1074 | O1 | HOH | 1079 | 24.829 | −14.257 | 24.782 | 1.00 | 24.91 |
| ATOM | 1075 | O1 | HOH | 1080 | 13.266 | −13.588 | 42.052 | 1.00 | 24.33 |
| ATOM | 1076 | O1 | HOH | 1081 | 24.443 | 2.764 | 17.515 | 1.00 | 24.61 |
| ATOM | 1077 | O1 | HOH | 1082 | 4.269 | −9.664 | 30.981 | 1.00 | 24.44 |
| ATOM | 1078 | O1 | HOH | 1083 | 4.143 | −10.890 | 22.698 | 1.00 | 22.21 |
| ATOM | 1079 | O1 | HOH | 1084 | 18.040 | 4.749 | 42.785 | 1.00 | 25.14 |
| ATOM | 1080 | O1 | HOH | 1085 | 1.136 | −9.675 | 22.102 | 1.00 | 27.39 |
| ATOM | 1081 | O1 | HOH | 1086 | 9.192 | 14.318 | 28.336 | 1.00 | 22.60 |
| ATOM | 1082 | O1 | HOH | 1087 | 19.935 | −4.720 | 19.071 | 1.00 | 29.60 |
| ATOM | 1083 | O1 | HOH | 1088 | 4.049 | −5.334 | 16.898 | 1.00 | 21.65 |
| ATOM | 1084 | O1 | HOH | 1089 | 27.148 | 9.654 | 24.125 | 1.00 | 24.37 |
| ATOM | 1085 | O1 | HOH | 1090 | 16.984 | 11.029 | 13.815 | 1.00 | 27.26 |
| ATOM | 1086 | O1 | HOH | 1091 | 20.544 | −2.126 | 18.367 | 1.00 | 22.99 |
| ATOM | 1087 | O1 | HOH | 1092 | 23.707 | 3.151 | 39.432 | 1.00 | 28.88 |
| ATOM | 1088 | O1 | HOH | 1093 | −1.920 | −4.147 | 30.571 | 1.00 | 27.39 |
| ATOM | 1089 | O1 | HOH | 1094 | 11.899 | −14.917 | 37.385 | 1.00 | 32.81 |
| ATOM | 1090 | O1 | HOH | 1095 | 20.795 | 14.376 | 16.474 | 1.00 | 29.46 |
| ATOM | 1091 | S | SO4 | 300 | 17.194 | −14.451 | 26.775 | 1.00 | 23.76 |
| ATOM | 1092 | O1 | SO4 | 300 | 17.779 | −15.800 | 26.674 | 1.00 | 25.07 |
| ATOM | 1093 | O2 | SO4 | 300 | 16.796 | −13.993 | 25.435 | 1.00 | 24.21 |
| ATOM | 1094 | O3 | SO4 | 300 | 16.011 | −14.509 | 27.652 | 1.00 | 24.52 |
| ATOM | 1095 | O4 | SO4 | 300 | 18.190 | −13.524 | 27.343 | 1.00 | 23.52 |
| ATOM | 1096 | S | SO4 | 301 | 13.826 | −5.555 | 16.116 | 1.00 | 19.81 |
| ATOM | 1097 | O1 | SO4 | 301 | 13.393 | −6.524 | 15.095 | 1.00 | 21.58 |
| ATOM | 1098 | O2 | SO4 | 301 | 13.720 | −4.187 | 15.584 | 1.00 | 19.29 |
| ATOM | 1099 | O3 | SO4 | 301 | 12.996 | −5.693 | 17.324 | 1.00 | 20.41 |
| ATOM | 1100 | O4 | SO4 | 301 | 15.233 | −5.831 | 16.467 | 1.00 | 22.09 |
| ATOM | 1101 | S | SO4 | 302 | 13.249 | 23.091 | 32.541 | 1.00 | 76.58 |
| ATOM | 1102 | O1 | SO4 | 302 | 13.950 | 22.101 | 31.704 | 1.00 | 76.66 |
| ATOM | 1103 | O2 | SO4 | 302 | 12.256 | 22.409 | 33.391 | 1.00 | 76.74 |
| ATOM | 1104 | O3 | SO4 | 302 | 14.229 | 23.787 | 33.395 | 1.00 | 76.89 |
| ATOM | 1105 | O4 | SO4 | 302 | 12.559 | 24.071 | 31.680 | 1.00 | 76.61 |
| END | | | | | | | | | |

What is claimed is:

1. An isolated Fibroblast Growth Factor 4 (FGF4) antagonist polypeptide having the amino acid sequence set forth for FGF4 in FIG. 2 (top line) (SEQ ID NO: 20) with substitution of an alanine amino acid residue for:

(a) threonine at amino acid residue 196.

2. A mutant Human Fibroblast Growth Factor 4 (FGF4) antagonist polypeptide having the amino acid sequence set forth in SEQ ID NO. 20, wherein at least one amino acid residue in the secondary binding site selected from Leu 162, Pro 195 and Thr 196 is substituted with alanine.

* * * * *

UNITED STATES PATENT AND TRADEMARK OFFICE
CERTIFICATE OF CORRECTION

| | |
|---|---|
| PATENT NO. | : 7,294,706 B2 |
| APPLICATION NO. | : 10/771238 |
| DATED | : November 13, 2007 |
| INVENTOR(S) | : Claudio Basilico et al. |

It is certified that error appears in the above-identified patent and that said Letters Patent is hereby corrected as shown below:

Title Page, Item (63) Related U.S. Application Data:

Please delete "August 1, 2004" and insert --August 1, 2002--.

Signed and Sealed this

Twenty-fifth Day of March, 2008

JON W. DUDAS
*Director of the United States Patent and Trademark Office*